(12) United States Patent
Bradley et al.

(10) Patent No.: US 10,597,466 B2
(45) Date of Patent: Mar. 24, 2020

(54) CIRCULAR TANDEM REPEAT PROTEINS

(71) Applicant: Fred Hutchinson Cancer Research Center, Seattle, WA (US)

(72) Inventors: Philip Bradley, Seattle, WA (US); Barry L. Stoddard, Seattle, WA (US)

(73) Assignee: FRED HUTCHINSON CANCER RESEARCH CENTER, Seattle, WA (US)

(*) Notice: Subject to any disclaimer, the term of this patent is extended or adjusted under 35 U.S.C. 154(b) by 0 days.

(21) Appl. No.: 15/780,397

(22) PCT Filed: Dec. 2, 2016

(86) PCT No.: PCT/US2016/064732
§ 371 (c)(1),
(2) Date: May 31, 2018

(87) PCT Pub. No.: WO2017/096236
PCT Pub. Date: Jun. 8, 2017

(65) Prior Publication Data
US 2019/0002590 A1    Jan. 3, 2019

Related U.S. Application Data

(60) Provisional application No. 62/262,146, filed on Dec. 2, 2015.

(51) Int. Cl.
*C07K 14/00* (2006.01)
*C07K 14/47* (2006.01)
(Continued)

(52) U.S. Cl.
CPC ............... *C07K 19/00* (2013.01); *C07K 7/08* (2013.01); *C07K 14/00* (2013.01); *C07K 14/001* (2013.01);
(Continued)

(58) Field of Classification Search
CPC ......  C07K 14/00; C07K 14/001; C07K 14/47; C07K 14/55; C07K 19/00; C07K 2319/00;
(Continued)

(56) References Cited

U.S. PATENT DOCUMENTS

2011/0294983 A1    12/2011    Desmet et al.
2019/0012428 A1*    1/2019    Parmeggiani .......... C12N 15/79

FOREIGN PATENT DOCUMENTS

WO    WO2002020565    3/2002
WO    WO2009100990    8/2009

OTHER PUBLICATIONS

Doyle et al. Rational design of alpha-helical tandem repeat proteins with closed architectures. Nature. 528(7583):585-588 + Extended Data Figures and Tables, Supplementary Information. Dec. 16, 2015. (Year: 2015).*

(Continued)

*Primary Examiner* — Jeffrey E. Russel
(74) *Attorney, Agent, or Firm* — Lee & Hayes PC; C. Rachal Winger

(57) ABSTRACT

Circular handed alpha-helical repeat proteins are described. The repeat proteins have a number of uses as scaffolds for geometrically precise, arrayed presentation of cell-signaling or immune-related protein and peptide epitopes, as well as numerous other therapeutic, diagnostic, and nanotechnological uses.

20 Claims, 55 Drawing Sheets
Specification includes a Sequence Listing.

(51) Int. Cl.
    *C07K 19/00*      (2006.01)
    *C12N 15/62*      (2006.01)
    *C07K 14/44*      (2006.01)
    *C07K 7/08*      (2006.01)
    *C07K 14/55*      (2006.01)
    *A61K 38/00*      (2006.01)

(52) U.S. Cl.
CPC .............. *C07K 14/44* (2013.01); *C07K 14/47* (2013.01); *C07K 14/55* (2013.01); *C12N 15/62* (2013.01); *A61K 38/00* (2013.01); *C07K 2319/00* (2013.01); *C07K 2319/21* (2013.01); *C07K 2319/50* (2013.01); *C07K 2319/70* (2013.01)

(58) Field of Classification Search
CPC ............ C07K 2319/21; C07K 2319/70; C07K 2319/72; C07K 2319/735
See application file for complete search history.

(56) References Cited

OTHER PUBLICATIONS

Adams, et al., "PHENIX: a comprehensive Python-based system for macromolecular structure solution," Acta Crystallogr. D., vol. 66, Pt. 2, 2010, pp. 213-221.
Afonine et al., "Towards automated crystallographic structure refinement with phenix.refine," Acta Crystallogr, 2012, D68, pp. 352-367.
Andrade, et al., "Protein repeats: structures, functions, and evolution," J. Struct. Biol., vol. 134, 2001, pp. 117-131.
Barkan, et al., "A combinatorial amino acid code for RNA recognition by pentatricopeptide repeat proteins," PLoS Genet., vol. 8, 2010, p. e1002910.
Binz, et al., "High-affinity binders selected from designed ankyrin repeat protein libraries," Nat. Biotechnol., vol. 22, 2004, pp. 575-582.
Boersma & Pluckthun, "DARPins and other repeat protein scaffolds: advances in engineering and applications," Curr. Opin. Biotechnol., vol. 22, No. 6, 2011, pp. 849-857.
Brooks, et al., "CHARMM: A program for macromolecular energy, minimization, and dynamics calculations," J. Comp. Chem., vol. 4, 1983, pp. 187-217.
Brooks, et al., "CHARMM: The Biomolecular Simulation Program," J. Comp. Chem., vol. 30, No. 10, 2009, pp. 1545-1615.
Chen, et al., "Fusion protein linkers: property, design and functionality," Adv. Drug Deliv. Rev., vol. 65, No. 10, 2013, pp. 1357-1369.
Cheng, et al., "ECOD: An Evolutionary Classification of Protein Domains", PLoS Comput. Biol, vol. 10, No. 12, 2014, 18 pages.
Deng, et al., "Structural basis for sequence-specific recognition of DNA by TAL effectors," Science, vol. 335, No. 6069, 2012, pp. 720-723.
Di Domenico, et al., "RepeatsDB: a database of tandem repeat protein structures," Nucleic Acids Res., vol. 42, 2014, pp. D352-D357.
Emsley, et al., "Features and development of Coot," Acta Crystallogr., D66, 2010, pp. 486-501.
Fox, et al., "SCOPe: Structural Classification of Proteins-extended, integrating SCOP and ASTRAL data and classification of new structures," Nucleic Acids Res., vol. 42, 2014, pp. D304-D309.
Grove, et al., "Ligand binding by repeat proteins: natural and designed," Curr. Opin. Stud. Biol., vol. 18, 2008, pp. 507-515.
Holm and Rosenstrom, "Dali server: conservation mapping in 3D," Nucleic Acids Res., vol. 38, 2010, pp. W545-W549.
Kajava, "Tandem repeats in proteins: from sequence to structure," J. Struct. Biol., vol. 179, 2012, pp. 279-288.
Kobe and Kajava, "When protein folding is simplified to protein coiling: the continuum of solenoid protein structures," Trends Biochem. Sci., vol. 25, No. 10, 2000, pp. 509-515.

MacKerell, et al., "All-atom empirical potential for molecular modeling and dynamics studies of proteins," J. Phys. Chem. B., vol. 102, No. 18, 1998, pp. 3586-3616.
MacKerell, et al., "CHARMM: The Energy Function and Its Parameterization with an Overview of the Program", The Encyclopedia of Computational Chemistry, vol. 1, 1998, pp. 271-277.
Main, et al., "Design of Stable a-Helix Arrays from an Idealized TPR Motif," Structure, vol. 11, No. 5, 2003, pp. 497-508.
Mak, et al., "The crystal structure of TAL effector PthXo1 bound to its DNA target," Science, vol. 335, No. 6069, pp. 716-719, Feb. 10, 2012).
Marcotte, et al., "A census of protein repeats," J. Mol. Biol., vol. 293, 1999, pp. 151-160.
McCoy, et al., "Phaser crystallographic software," J. Appl. Crystallogr., vol. 40, 2007, pp. 658-674.
Otwinowski and Minor, "Processing of X-ray diffraction data collected in oscillation mode," Method. Enzymol., vol. 276, 1997, pp. 307-326.
Park, et al., "Control of repeat-protein curvature by computational protein design," Nat. Struct. Mol. Biol., vol. 22, 2015, pp. 167-174.
Parmeggiani, et al., "Designed armadillo repeat proteins as general peptide-binding scaffolds: consensus design and computational optimization of the hydrophobic core," J. Mol. Biol., vol. 376, 2008, pp. 1282-1304.
Ramisch, "Computational design of a leucine-rich repeat protein with a predefined geometry," PNAS, vol. 111, No. 20, 2014, pp. 17875-17880.
Reichen, et al., "Modular peptide binding: from a comparison of natural binders to designed armadillo repeat proteins," J. Struct Biol., vol. 185, No. 2, 2014, pp. 147-162.
Sillitoe, et al., "CATH: comprehensive structural and functional annotations for genome sequences," Nucleic Acid Res., 2015, vol. 43, pp. D376-D381.
Skubak, et al., "Direct incorporation of experimental phase information in model refinement," Acta Cryst., Biological Crystallography, D60, 2004, pp. 2196-2201.
Urvoas, et al., "Design, production and molecular structure of a new family of artificial alpha-helicoidal repeat proteins (alphaRep) based on thermostable HEAT-like repeats," J. Mol. Biol., vol. 404, No. 2, 2010, pp. 307-327.
Voet, et al., "Computational design of a self-assembling symmetrical beta-propeller protein," PNAS, vol. 111, 2014, pp. 15102-15107.
Walden, "Selenium incorporation using recombinant techniques," Acta Crystallogr. D. Biol Crystallogr., vol. 66, Pt. 4, 2010, pp. 352-357.
Wang, et al., "Modular recognition of RNA by a human pumilio-homology domain," Cell, vol. 110, 2002, pp. 501-512.
Wierenga, "The TIM-barrel fold: a versatile framework for efficient enzymes," FEBS Lett., vol. 492, No. 3, 2001, pp. 193-198.
Winn, et al., "Overview of the CCP4 suite and current developments," Acta Crystallogr. D. Biol Crystallogr., vol. 67, Pt. 4, 2011, pp. 235-242.
Wintjens, et al., "Automatic classification and analysis of alpha alpha-turn motifs in proteins," J. Mol. Biol., vol. 255, 1996, pp. 235-253.
Conlan, et al., "Circular proteins and mechanisms of cyclization," Biopolymers, vol. 94, No. 5, 2010, pp. 573-583.
Extended European Search Report dated Mar. 18, 2019, for European Application No. 16871620.7, 8 pages.
O'Meara, et al., "Combined Covalent-Electrostatic Model of Hydrogen Bonding Improves Structure Prediction with Rosetta," J. Chem. Theory Comput., vol. 11, No. 2, 2015, pp. 609-622.
Pascual, et al., "Solution structure of the spectrin repeat: a lefthanded antiparallel triple-helical coiled-coil," J. Mol. Biol., vol. 273, No. 3, 1997, pp. 740-751.
Trabi, et al., "Circular Proteins—no end in sight," TRENDS in Biochemical Sciences, vol. 27, No. 3, 2002, 7 pages.
Doyle, et al., "Rational design of a-helix tandem repeat proteins with closed architectures", Nature, vol. 528, 2015, pp. 585-588.
Forrer, et al., "Consensus Design of Repeat Proteins", ChemBioChem, vol. 5, 2004, pp. 183-189.
Invitation to Pay Additional Fees dated Feb. 8, 2017 for International Application No. PCT/US2016/064732.

(56) References Cited

OTHER PUBLICATIONS

Main, et al., "Design of Stable a-Helix Arrays fomr an Idealized TPR Motif", Strucure, vol. 11, No. 5, 2003, pp. 497-508.
Search Report and Written Opinion dated Apr. 28, 2017 for International Application No. PCT/US216/064732.
Office Action Dated Nov. 28, 2019 for European Patent Application No. 16871620.7, 4 pages.

* cited by examiner

FIG. 1A
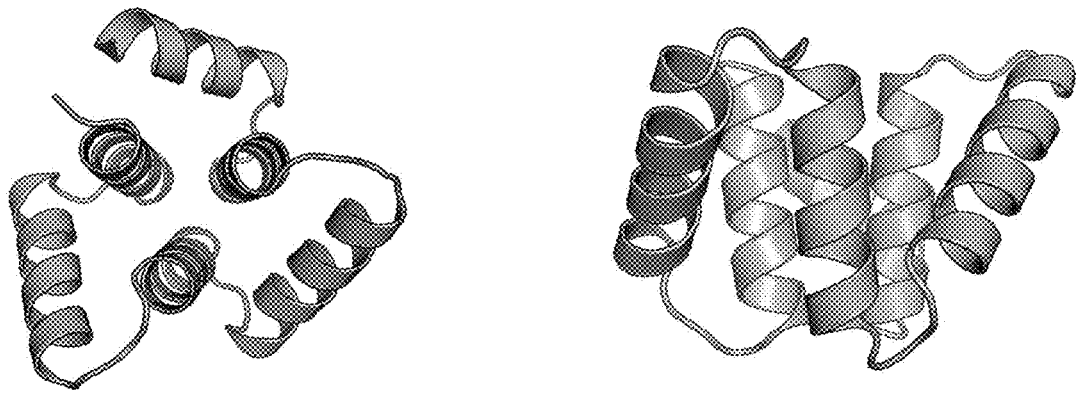
FIG. 1C
FIG. 1B
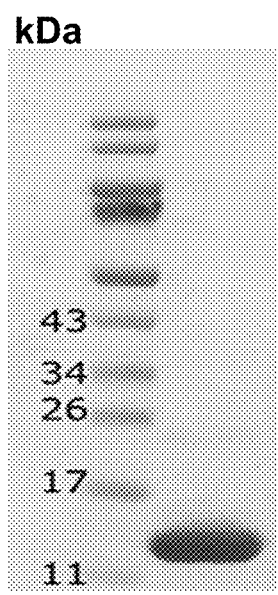
SDS-PAGE
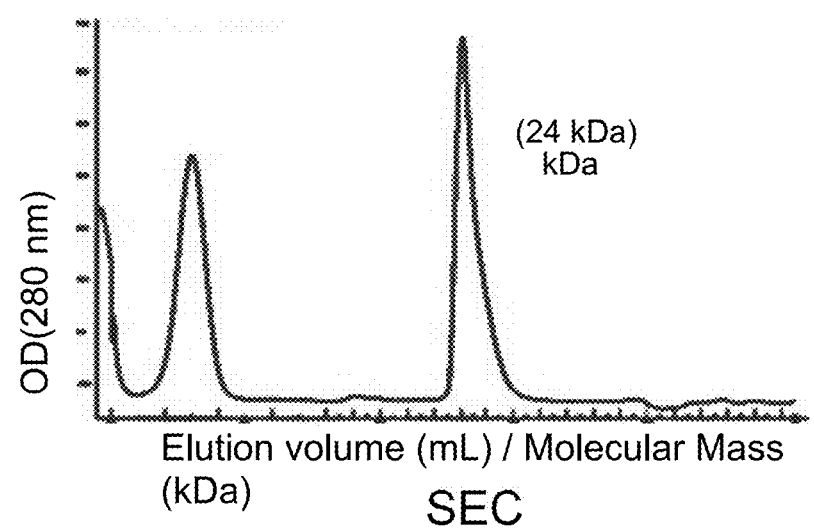
SEC
FIG. 1D
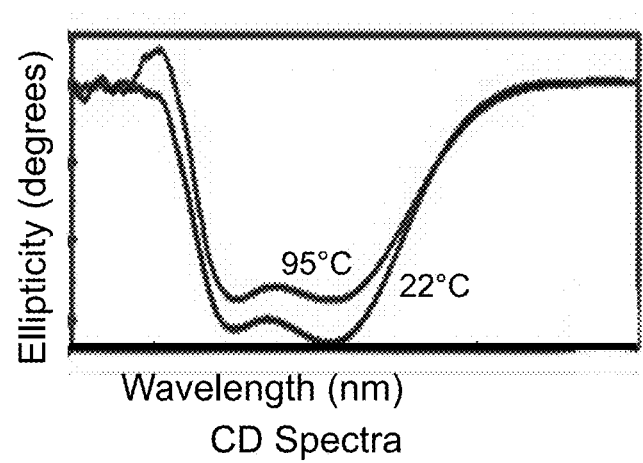
CD Spectra

FIG. 1E

MGKSPTEVLLELIAEASGTTREEVKEKFLKELRKGKSPTEVLLELIAEASGTTKEEVKEK
FLKELSFGKSPTEVLLELIAEASGTTKEEVKKKFWKELSL (SEQ ID NO: 117).

Repetitive Sequences in SEQ ID NO: 117 forming α-helical structures include:

PTEVLLELIAEAS (SEQ ID NO: 9);
REEVKEKFLKELRK (SEQ ID NO: 14);
KEEVKEKFLKELSF (SEQ ID NO: 15); and
KEEVKKKFWKELSL (SEQ ID NO: 16).

Repetitive Sequences forming α-helical structures joined by linkers in SEQ ID NO: 117 include:

GKSPTEVLLELIAEASGTTREEVKEKFLKELRK (SEQ ID NO: 83);
GKSPTEVLLELIAEASGTTKEEVKEKFLKELSF (SEQ ID NO: 84); and
GKSPTEVLLELIAEASGTTKEEVKKKFWKELSL (SEQ ID NO: 85).

FIG. 2A
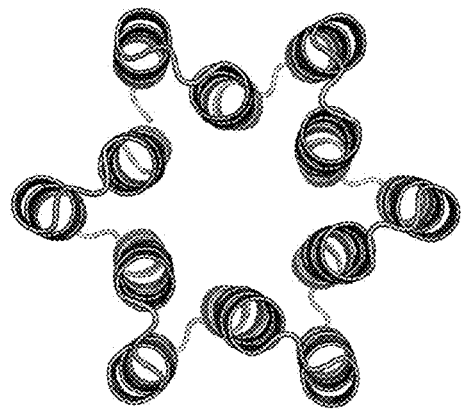 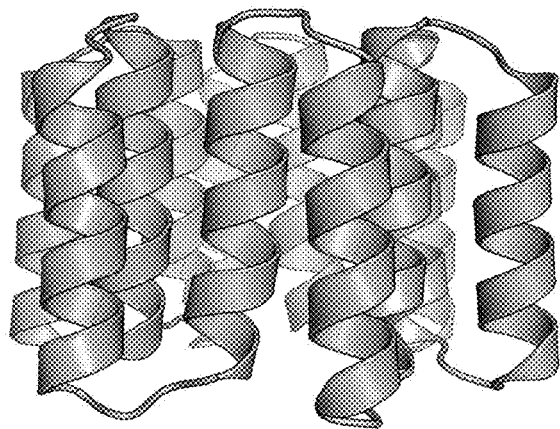
FIG. 2B
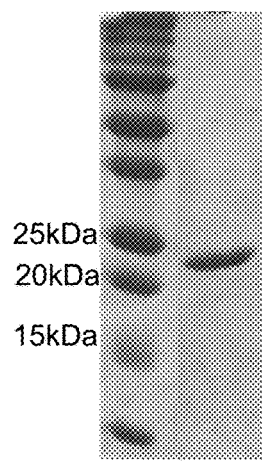
SDS-PAGE
FIG. 2C
(40 Å radius on DLS)

FIG. 2D

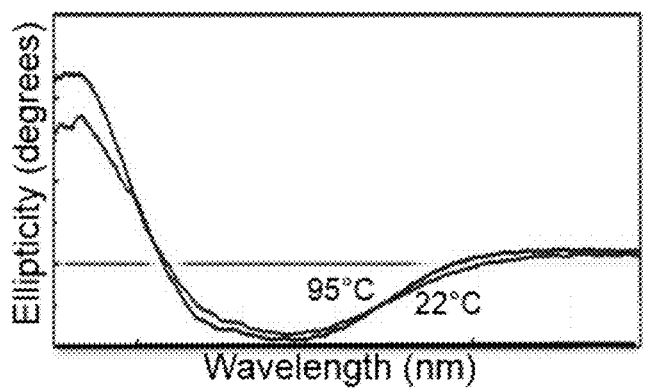

CD Spectra

FIG. 2E

MGDKTAIAQILAIKASAKGDETELERALRYAVKVGDKTAIAQILAIKASAKGDETELEQAL
RYAKFVGDKTAIAQILAIKASAKGDELELTRALAYAKKVGDKTAIAQILAIKASAKGDETE
LERALRYAKLVGDKTAIAQILAIKASAKGDETELERALRYAKYVGDKTAIAQILAIKASAK
GDEPELEYALAYAKKV (SEQ ID NO: 118).

Repetitive Sequences in SEQ ID NO: 118 forming α-helical structures include:

TAIAQILAIKASAK (SEQ ID NO: 22);
TELERALRYAVKV (SEQ ID NO: 24);
TELEQALRYAKFV (SEQ ID NO: 25);
LELTRALAYAKKV (SEQ ID NO: 26);
TELERALRYAKLV (SEQ ID NO: 27);
TELERALRYAKYV (SEQ ID NO: 28); and
PELEYALAYAKKV (SEQ ID NO: 29).

Repetitive Sequences forming α-helical structures joined by linkers in SEQ ID NO: 118 include:

GDKTAIAQILAIKASAKGDETELERALRYAVKV (SEQ ID NO: 91);
GDKTAIAQILAIKASAKGDETELEQALRYAKFV (SEQ ID NO: 92);
GDKTAIAQILAIKASAKGDELELTRALAYAKKV (SEQ ID NO: 93);
GDKTAIAQILAIKASAKGDETELERALRYAKLV (SEQ ID NO: 94);
GDKTAIAQILAIKASAKGDETELERALRYAKYV (SEQ ID NO: 95); and
GDKTAIAQILAIKASAKGDEPELEYALAYAKKV (SEQ ID NO: 96).

SDS-PAGE

Elution volume (mL) / Molecular Mass (kDa)
SEC

Wavelength (nm)
CD Spectra

FIG. 3E

LVSLEQALKILKVAAELGTTVEEAVKRALKLKTKLGVSLEQALKILEVAAELGTTVEEAVK
RALKLKTKLGVSLEQALKILEVAAKLGTTVEEAVKRALKLKTKLGVSLEQALKILKVAAEL
GTTVEEAVKRALKLKTKLGVSLEQALKILEVAAELGTTVEEAVKRAMKLKTKLGVSLEQ
ALKILEVAAKLGTTVEEAVKRALKLKTKLGGWLEHHHHHH (SEQ ID NO: 119).

Repetitive Sequences in SEQ ID NO: 119 forming α–helical structures include:

LEQALKILKVAAEL (SEQ ID NO: 46);
VEEAVKRALKLKTKL (SEQ ID NO: 47);
LEQALKILEVAAEL (SEQ ID NO: 48);
LEQALKILEVAAKL (SEQ ID NO: 49); and
VEEAVKRAMKLKTKL (SEQ ID NO: 50).

Repetitive Sequences forming α–helical structures joined by linkers in SEQ ID NO: 119 include:

LVSLEQALKILKVAAELGTTVEEAVKRALKLKTKL (SEQ ID NO: 172)
GVSLEQALKILKVAAELGTTVEEAVKRALKLKTKL (SEQ ID NO: 111);
GVSLEQALKILEVAAELGTTVEEAVKRALKLKTKL (SEQ ID NO: 112);
GVSLEQALKILEVAAKLGTTVEEAVKRALKLKTKL (SEQ ID NO: 113); and
GVSLEQALKILEVAAELGTTVEEAVKRAMKLKTKL (SEQ ID NO: 114).

kDa 34
26

SDS-PAGE

SEC

CD Spectra

FIG. 4E

GSSMASGISVEELLKLAKAAYYSGTTVEEAYKLALKLGISVEELLKLAEAAYYSGTTVEE
AYKLALKLGISVEELLKLAKAAYYSGTTVEEAYKLALKLGISVEELLKLAKAAYYSGTTVE
EAYKLALKLGISVEELLKLAEAAYYSGTTVEEAYKLALKLGISVEELLKLAKAAYYSGTTV
EEAYKLALKLGISVEELLKLAKAAYYSGTTVEEAYKLALKLGISVEELLKLAEAAYYSGTT
VEEAYKLALKLGISVEELLKLAKAAYYSGTTVEEAYKLALKLG (SEQ ID NO: 120).

Repetitive Sequences in SEQ ID NO: 120 forming α-helical structures include:

VEELLKLAKAAYYS (SEQ ID NO: 1);
VEEAYKLALKL (SEQ ID NO: 2); and
VEELLKLAEAAYYS is SEQ ID NO: 3.

Repetitive Sequences forming α-helical structures joined by linkers in SEQ ID NO: 120 include:

GISVEELLKLAKAAYYSGTTVEEAYKLALKL (SEQ ID NO: 73); and
GISVEELLKLAEAAYYSGTTVEEAYKLALKL (SEQ ID NO: 74).

SDS-PAGE

SEC

CD Spectra

FIG. 5E

GSSMASGISVEELLKLAKAAYYSGTTVEEAYKLALKLGISVEELLKLAEAAYYSGTTVEE
AYKLALKLGISVEELLKLAKAAYYSGTTVEEAYKLALKLGISVEELLKLAKAAYYSGTTVE
EAYKLALKLGISVEELLKLAEAAYYSGTTVEEAYKLALKLGISVEELLKLAKAAYYSGTTV
EEAYKLALKLGISVEELLKLAKAAYYSGTTVEEAYKLALKLGISVEELLKLAEAAYYSGTT
VEEAYKLALKLGISVEELLKLAKAAYYSGTTVEEAYKLALKLGISVEELLKLAKAAYYSGT
TVEEAYKLALKLGISVEELLKLAEAAYYSGTTVEEAYKLALKLGISVEELLKLAKAAYYSG
TTVEEAYKLALKLG
(SEQ ID NO: 121).

Repetitive Sequences in SEQ ID NO: 121 forming α-helical structures include:

VEELLKLAKAAYYS (SEQ ID NO: 1);
VEEAYKLALKL (SEQ ID NO: 2); and
VEELLKLAEAAYYS (SEQ ID NO: 3).

Repetitive Sequences forming α-helical structures joined by linkers in SEQ ID NO: 121 include:

GISVEELLKLAKAAYYSGTTVEEAYKLALKL (SEQ ID NO: 73); and
GISVEELLKLAEAAYYSGTTVEEAYKLALKL (SEQ ID NO: 74).

kDa

10

SDS-PAGE

SEC

CD Spectra

FIG. 6E

GSSMASGISVEELLKLAKAAYYSGTTVEEAYKLALKLGISVEELLKLAEAAYYSGTTVEE
AYKLALKLGISVEELLKLAKAAYYSGTTVEEAYKLALKLG* (SEQ ID NO: 122).

Repetitive Sequences in SEQ ID NO: 122 forming α-helical structures include:

VEELLKLAKAAYYS (SEQ ID NO: 1);
VEEAYKLALKL (SEQ ID NO: 2); and
VEELLKLAEAAYYS (SEQ ID NO: 3.

Repetitive Sequences forming α-helical structures joined by linkers in SEQ ID NO: 122 include:

GISVEELLKLAKAAYYSGTTVEEAYKLALKL (SEQ ID NO: 73); and
GISVEELLKLAEAAYYSGTTVEEAYKLALKL (SEQ ID NO: 74).

SDS-PAGE

SEC

CD Spectra

FIG. 7E

GLGLNPEAIKAAAELGKAGISSEEILELLRAAHELGLNPEAIKAAAELGKAGISSEEILELL
RAAHELGLNPEAIKAAAELGKAGISSEEILELLRAAHALGLNPEAIKAAAELGKAGISSAE
ILELLMAAHELGLNPEAIKAAAELGKAGISSEEILELLRAAHELGLNPEAIKAAAELGKAGI
SSEEILELLRAAHGLGLNPEAIKAAAELGKAGISSEEILELLRAAHELGLNPEAIKAAAEL
GKAGISSEEILELLRAAHELGLNPEAIKAAAELGKAGISSEEILELLRAAHALGLNPEAIKA
AAELGKAGISSAEILELLMAAHELGLNPEAIKAAAELGKAGISSEEILELLRAAHELGLNP
EAIKAAAELGKAGISSEEILELLRAAHGLGLNPEAIKAAAELGKAGISSEEILELLRAAHEL
GLNPEAIKAAAELGKAGISSEEILELLRAAHELGLNPEAIKAAAELGKAGISSEEILELLRA
AHALGLNPEAIKAAAELGKAGISSAEILELLMAAHELGLNPEAIKAAAELGKAGISSEEILE
LLRAAHELGLNPEAIKAAAELGKAGISSEEILELLRAAHGLGLNPEAIKAAAELGKAGISS
EEILELLRAAHELGLNPEAIKAAAELGKAGISSEEILELLRAAHELGLNPEAIKAAAELGKA
GISSEEILELLRAAHALGLNPEAIKAAAELGKAGISSAEILELLMAAHELGLNPEAIKAAAE
LGKAGISSEEILELLRAAHELGLNPEAIKAAAELGKAGISSEEILELLRAAHGGW
(SEQ ID NO: 123).

Repetitive Sequences in SEQ ID NO: 123 forming α-helical structures include:

PEAIKAAAELGKA (SEQ ID NO: 124);
SEEILELLRAAHEL (SEQ ID NO: 125);
SEEILELLRAAHAL (SEQ ID NO: 126);
SAEILELLMAAHEL (SEQ ID NO: 127);
SEEILELLRAAHGL (SEQ ID NO: 128); and
SEEILELLRAAHGG (SEQ ID NO: 129).

Repetitive Sequences forming α-helical structures joined by linkers in SEQ ID NO: 123 include:

GLNPEAIKAAAELGKAGISSEEILELLRAAHEL (SEQ ID NO: 130);
GLNPEAIKAAAELGKAGISSEEILELLRAAHAL (SEQ ID NO: 131);
GLNPEAIKAAAELGKAGISSAEILELLMAAHEL (SEQ ID NO: 132);
GLNPEAIKAAAELGKAGISSEEILELLRAAHGL (SEQ ID NO: 133); and
GLNPEAIKAAAELGKAGISSEEILELLRAAHGG (SEQ ID NO: 134).

SAXS data
Experimental $R_g$ (radius) = 39.55 Å
Theoretical radius = 47 Å dTor_24x33_1.1x (multimeric assemblages)

FIG. 9E

>design_24x_sub8__Protein:
GSSMGLDPEAIKAAAELGKAGISSEEILELLRAAHELGLDPEAIKAAAELGKAGISSEEIL
ELLRAAHELGLDPEAIKAAAELGKAGISSEEILELLRAAHVLGLDPEAIKAAAELGKAGIS
SEEILELLVAAHLLGLDPEAIKAAAELGKAGISSEEILELLRAAHELGLDPEAIKAAAELGK
AGISSEEILELLRAAHELGLDPEAIKAAAELGKAGISSEEILELLRAAHELGLDPEAIKAAA
ELGKAGISSIEILELLRAAHELGGW (SEQ ID NO: 135);

>design_24x_sub6_Protein:
GSSMGLDPEAIKAAAELGKAGISSEEILELLRAAHELGLDPEAIKAAAELGKAGISSEEIL
ELLRAAHELGLDPEAIKAAAELGKAGISSEEILELLRAAHELGLDPEAIKAAAELGKAGIS
SEEILELLRAAHELGLDPEAIKAAAELGKAGISSEEILELLRAAHELGLDPEAIKAAAELGK
AGISSEEILELLRAAHELG (SEQ ID NO: 136);

>design_24x_sub4_Protein:
GSSMGLDPEAIKAAAELGKAGISSEEILELLRAAHELGLDPEAIKAAAELGKAGISSEEIL
ELLRAAHELGLDPEAIKAAAELGKAGISSEEILELLRAAHELGLDPEAIKAAAELGKAGIS
SEEILELLRAAHELG (SEQ ID NO: 137);

>design_24x_sub3_Protein:
GSSMGLDPEAIKAAAELGKAGISSEEILELLRAAHELGLDPEAIKAAAELGKAGISSEEIL
ELLRAAHELGLDPEAIKAAAELGKAGISSEEILELLRAAHELG
(SEQ ID NO: 138).

Repetitive Sequences in SEQ ID NO: 135-138 forming α–helical structures include:

PEAIKAAAELGKA (SEQ ID NO: 124);
SEEILELLRAAHEL (SEQ ID NO: 125);
SEEILELLRAAHVL (SEQ ID NO: 139); and
SIEILELLRAAHEL (SEQ ID NO: 140).

Repetitive Sequences forming α–helical structures joined by linkers in SEQ ID NO: 135-138 include:

GLDPEAIKAAAELGKAGISSEEILELLRAAHEL (SEQ ID NO: 141);
GLDPEAIKAAAELGKAGISSEEILELLRAAHVL (SEQ ID NO: 142);
GLDPEAIKAAAELGKAGISSEEILELLVAAHLL (SEQ ID NO: 143); and
GLDPEAIKAAAELGKAGISSIEILELLRAAHEL (SEQ ID NO: 144).

FIG. 10A
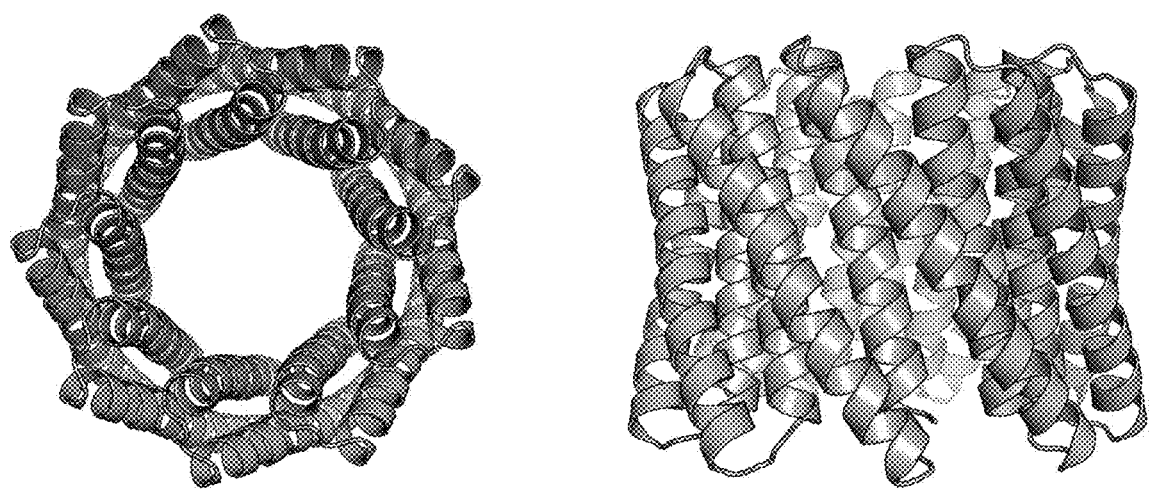
FIG. 10B
FIG. 10C
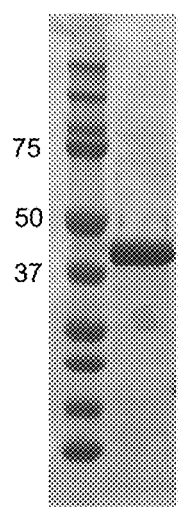
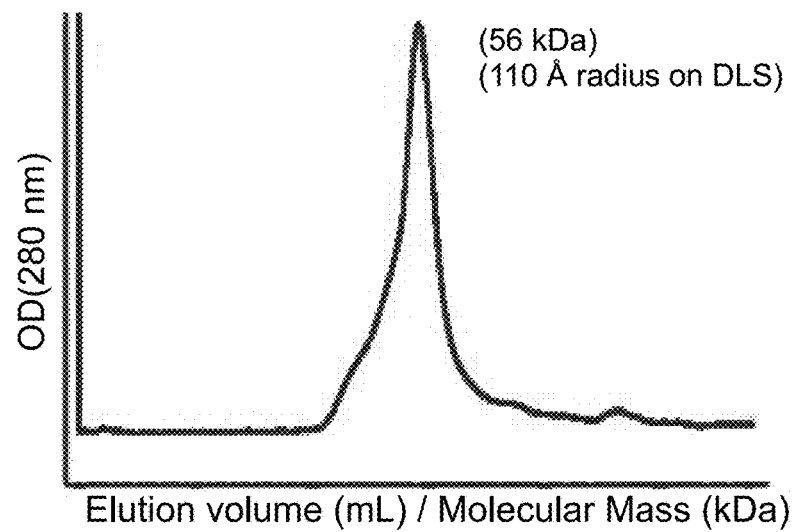
SDS-PAGE
SEC

FIG. 10D

GNLELALKALQILVNAAYVLAEIARDRGNEELLEKAARLAEEAARQAEEIARQARKEGN
LELALKALQILVNAAYVLAEIARDRGNEELLEKAARLAEEAARQAEEIARQARKEGNLEL
ALKALQILVNAAYVLAEIARDRGNEELLEKAARLAEEAARQAEEIARQARKEGNLELALK
ALQILVNAAYVLAEIARDRGNEELLEKAARLAEEAARQAEEIARQARKEGNLELALKALQ
ILVNAAYVLAEIARDRGNEELLEKAARLAEEAARQAEEIARQARKEGNLELALKALQILV
NAAYVLAEIARDRGNEELLEKAARLAEEAARQAEEIARQARKEGNLELALKALQILVNA
AYVLAEIARDRGNEELLEKAARLAEEAARQAEEIARQARKEGNLELALKALQILVNAAYV
LAEIARDRGNEELLEKAARLAEEAARQAEEIARQARKEGNLELALKALQILVNAAYVLAE
IARDRGNEELLEKAARLAEEAARQAEEIARQARKEG (SEQ ID NO: 145).

Repetitive Sequences in SEQ ID NO: 145 forming α-helical structures include:

ELALKALQILVNAAYVLAEIARDR (SEQ ID NO: 146); and
ELLEKAARLAEEAARQAEEIARQARKE (SEQ ID NO: 147).

Repetitive Sequences forming α-helical structures joined by linkers in SEQ ID NO: 145 include:

GNLELALKALQILVNAAYVLAEIARDRGNEELLEKAARLAEEAARQAEEIARQARKE
(SEQ ID NO: 148).

FIG. 11 CONT'D
4. CLUSTER
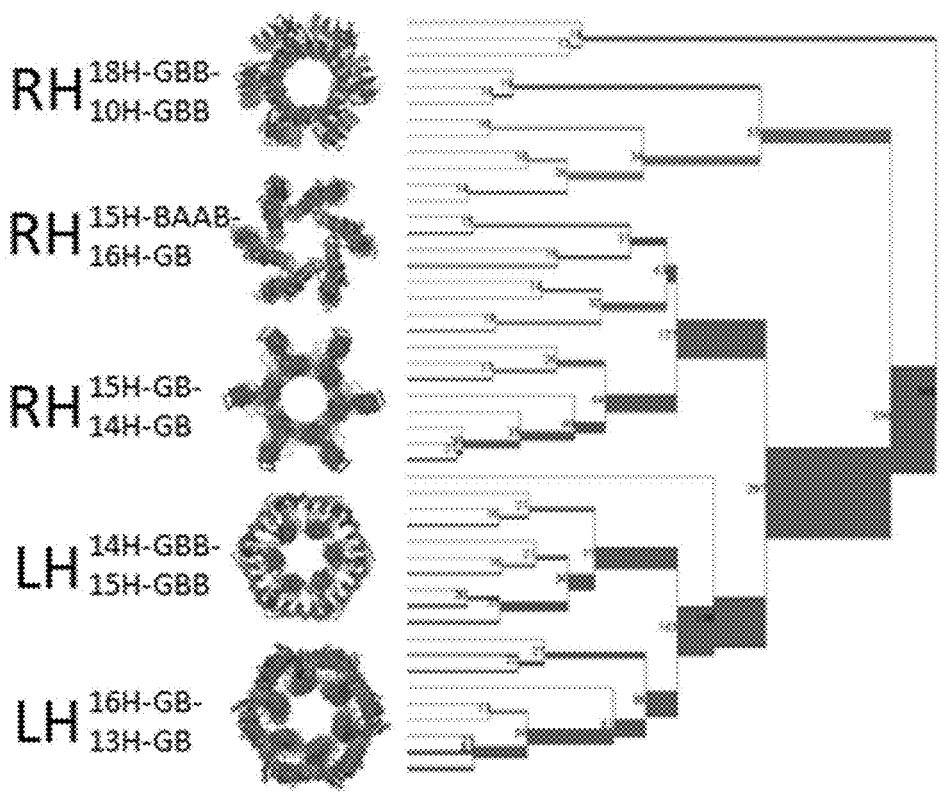
RH$_{10H-GBB}^{18H-GBB}$
RH$_{16H-GB}^{15H-BAAB-}$
RH$_{14H-GB}^{15H-GB-}$
LH$_{15H-GBB}^{14H-GBB-}$
LH$_{13H-GB}^{16H-GB-}$
5. RESAMPLE
*FOLD-DESIGN-FILTER:*
1000× 16H-GB-13H-GB
1000× 14H-GBB-15H-GBB
1000× 15H-GB-14H-GB
6. REFOLD
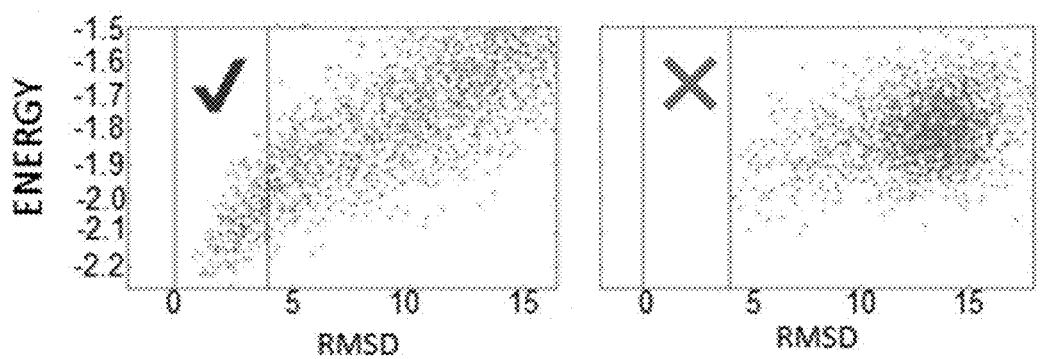

FIG. 12
Left-handed toroid
(dTor_12x31L)
Right-handed toroid
(4ADY A/307-712/)
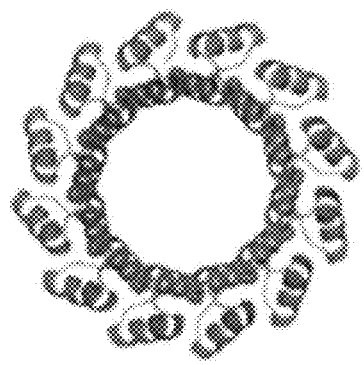
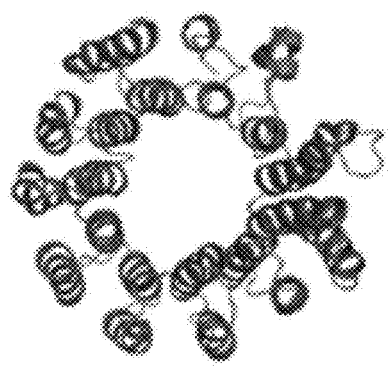
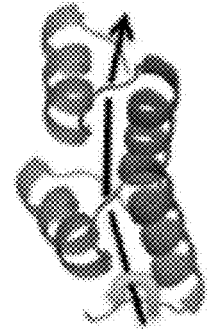
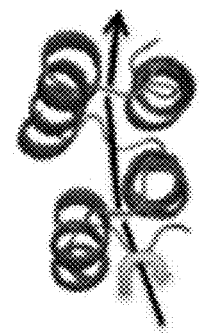
Helical bundle axis ⬆
Peptide chain direction ⤴

FIG. 13

| ID: dTor_ | # of Repeats | Repeat Length | Bundle Handed-ness | Expressed[a] | Purified[b] | Oligomeric state[c] | Crystals[d] | Structure[e] |
|---|---|---|---|---|---|---|---|---|
| 9x31L_sub3[f] | 3 | 31 | Left | Y | Y | M/D[g] | Y | Y |
| 3x33L_1 | 3 | 33 | Left | Y | Y | | Y | N |
| 3x33L_1-1 | 3 | 33 | Left | Y | Y | | N | |
| 3x33L_2 | 3 | 33 | Left | Y | Y | | Y | N |
| 3x33L_2-1 | 3 | 33 | Left | Y | N | | | |
| 3x33L_2-2 | 3 | 33 | Left | Y | Y | D | Y | Y |
| 3x33L_2-3 | 3 | 33 | Left | Y | N | | | |
| 3x33L_2-4 | 3 | 33 | Left | Y | N | | | |
| 3x33L_3 | 3 | 33 | Left | Y | N/A | | | |
| 6x33R_1 | 6 | 33 | Right | Y | Y | | Y | N |
| 6x33R_1-1 | 6 | 33 | Right | Y | N | | | |
| 6x33R_1-2 | 6 | 33 | Right | Y | N | | | |

[a]: Construct was successfully overexpressed

[b]: Construct was successfully purified to homogeneity and concentrated to at least 1 mg/mL.

[c]: Dominant solution species, as assessed by size-exclusion chromatography (SEC) and dynamic light scattering (DLS); M: monomer, D: dimer.

[d]: Construct crystallized

[e]: Crystals diffracted and structure determination was successful

[f]: The 3-repeat subfragment of dTor_9x31L

[g]: Concentration-dependent monomer/dimer equilibrium

FIG. 13 cont'd

| ID: dTor_ | # of Repeats | Repeat Length | Bundle Handedness | Expressed[a] | Purified[b] | Oligomeric state[c] | Crystals[d] | Structure[e] |
|---|---|---|---|---|---|---|---|---|
| 6x33R_1-3 | 6 | 33 | Right | Y | N | | | |
| 6x33R_2 | 6 | 33 | Right | Y | N | | | |
| 6x33R_3 | 6 | 33 | Right | Y | N | | | |
| 6x33R_4 | 6 | 33 | Right | N | | | | |
| 6x35L | 6 | 35 | Left | Y | Y | D | Y | Y |
| 6x35L (SeMet) | 6 | 35 | Left | Y | Y | | Y | Y |
| 9x31L | 9 | 31 | Left | Y | Y | M | Y | Y |
| 12x31L | 12 | 31 | Left | Y | Y | M | Y | Y |
| 24x33 | 24 | 33 | Left | Y | Y | M | N | Y (SAXS)[h] |
| 24x33_sub3 | 3 | 33 | Left | Y | Y | M | N | |
| 24x33_sub4 | 4 | 33 | Left | Y | Y | M | N | |
| 24x33_sub6 | 6 | 33 | Left | Y | Y | M | N | |
| 24x33_sub8 | 8 | 33 | Left | Y | Y | M | N | |

[a]: Construct was successfully overexpressed

[b]: Construct was successfully purified to homogeneity and concentrated to at least 1 mg/mL.

[c]: Dominant solution species, as assessed by size-exclusion chromatography (SEC) and dynamic light scattering (DLS); M: monomer, D: dimer.

[d]: Construct crystallized

[e]: Crystals diffracted and structure determination was successful

[f]: The 3-repeat subfragment of dTor_9x31L

[g]: Concentration-dependent monomer/dimer equilibrium

[h]: Low resolution structure of dTor_24X33L was determined using small angle X-ray scattering (SAXS) as depicted in FIG. 8.

FIG. 15

| Turn Type[a] | Length | Count[b] | Helix Angle[c] | (std dev) | Helix Dihedral[d] | (std dev) | Fraction Left-Handed[e] |
|---|---|---|---|---|---|---|---|
| B | 1 | 1459 | 90.9 | (27.6) | 65.8 | (57.6) | 0.11 |
| E | 1 | 332 | 110.3 | (18.6) | -58.3 | (34.0) | 0.92 |
| G | 1 | 306 | 94.7 | (33.3) | -19.1 | (120.8) | 0.66 |
| BB | 2 | 961 | 104.4 | (32.6) | -10.4 | (59.1) | 0.59 |
| GB | 2 | 769 | 147.1 | (23.9) | 13.8 | (39.2) | 0.16 |
| GBB | 3 | 1154 | 121.2 | (27.8) | -58.8 | (42.4) | 0.95 |
| BAB | 3 | 458 | 136.8 | (26.6) | -6.8 | (47.9) | 0.52 |
| BBB | 3 | 165 | 96.0 | (49.5) | 1.6 | (94.7) | 0.41 |
| GABB | 4 | 251 | 149.2 | (24.5) | 1.6 | (38.8) | 0.50 |
| BBBB | 4 | 230 | 122.2 | (35.0) | 4.8 | (57.0) | 0.48 |
| GBBB | 4 | 179 | 121.2 | (31.5) | 23.5 | (74.4) | 0.35 |
| BAAB | 4 | 133 | 130.2 | (37.8) | 37.5 | (53.4) | 0.17 |
| GBBBB | 5 | 349 | 124.1 | (25.3) | -26.0 | (48.9) | 0.69 |
| BAABB | 5 | 192 | 136.6 | (20.9) | -10.5 | (43.5) | 0.61 |
| GBBBBB | 6 | 150 | 90.1 | (34.4) | -19.1 | (119.9) | 0.59 |

[a]: Backbone phi/psi angles of the turn in a 5-state coarse-grained alphabet
[b]: Number of occurrences in the Richardson Top8000 database
[c]: Average angle between the axes of the helices before and after the turn
[d]: Average dihedral angle formed by the helix axes and the helix end points
[e]: Fraction of turn occurrences with a negative dihedral (which would induce a left-handed helical bundle twist)

FIG. 16A
FIG. 16B
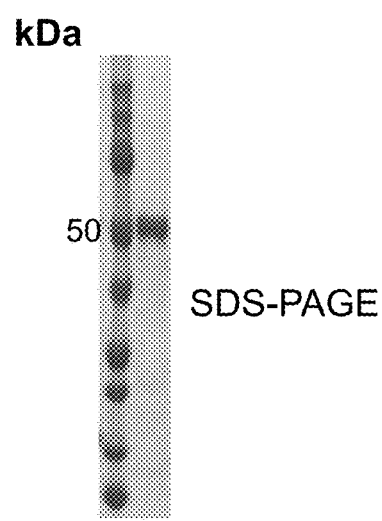

FIG. 16E

MASSHHHHHHSSGLVPRGSSMGISVEELLKLAKAAYYSGTTVEEAYKLALKLGISVEEL
LKLAEAAYYSGTTVEEAYKLALKLGISVEELLKLAKAAYYSGTTVEEAYKLALKLGISVEE
LLKLAKAAYYSGTTVEEAYKLALKLGISVEELLKLAEAAYYSGTTVEEAYKLALKLGISVE
ELLKLAKAAYYSGGSGGGSGGSGSEWYYGNVTRHQAECALNERGVEGDFLIRDSES
SPSDFSVSLKASGKNKHFKVQLVDNVYCIGQRRFHTMDELVEHYKKAPIFTSEHGEKL
YLVRALQGGSGGGSGSGTVEEAYKLALKLGISVEELLKLAKAAYYSGTTVEEAYKLALK
LGISVEELLKLAEAAYYSGTTVEEAYKLALKLGISVEELLKLAKAAYYSGTTVEEAYKLAL
KLGISVEELLKLAKAAYYSGTTVEEAYKLALKLGISVEELLKLAEAAYYSGTTVEEAYKLA
LKLGISVEELLKLAKAAYYSGTTVEEAYKLALKLG* (SEQ ID NO: 149).

Repetitive Sequences in SEQ ID NO: 149 forming α-helical structures include:

VEELLKLAKAAYYS (SEQ ID NO: 1);
VEEAYKLALKL (SEQ ID NO: 2); and
VEELLKLAEAAYYS (SEQ ID NO: 3).

Repetitive Sequences forming α-helical structures joined by linkers in SEQ ID NO: 149 include:

GISVEELLKLAKAAYYSGTTVEEAYKLALKL (SEQ ID NO: 73); and
GISVEELLKLAEAAYYSGTTVEEAYKLALKL (SEQ ID NO: 74).

Additional Linkers in SEQ ID NO: 149 include:

GGSGGGSGGSG (SEQ ID NO: 152); and
GGSGGGSGSG (SEQ ID NO: 153).

Functional Domains in SEQ ID NO: 149 include:

SEWYYGNVTRHQAECALNERGVEGDFLIRDSESSPSDFSVSLKASGKNKHFKVQLVD
NVYCIGQRRFHTMDELVEHYKKAPIFTSEHGEKLYLVRALQ (SEQ ID NO: 154).

FIG. 17A
SDS-PAGE
FIG. 17B
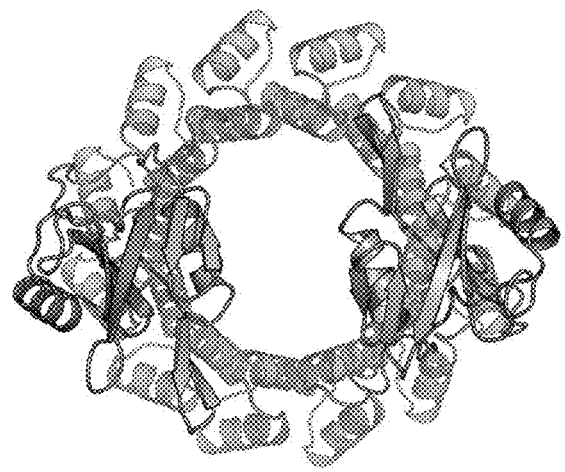
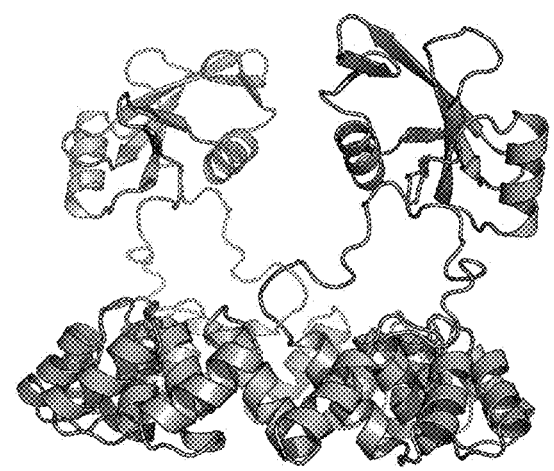

Elution volume (mL) / Molecular Mass (kDa)
SEC

Fluorescence Polarization

FIG. 17E

MASSHHHHHHSSGLVPRGSSMGISVEELLKLAKAAYYSGTTVEEAYKLALKLGISVEEL
LKLAEAAYYSGTTVEEAYKLALKLGISVEELLKLAKAAYYSGTTVEEAYKLALKLGISVEE
LLKLAKAAYYSGGSGGGSGGSGSEWYYGNVTRHQAECALNERGVEGDFLIRDSESS
PSDFSVSLKASGKNKHFKVQLVDNVYCIGQRRFHTMDELVEHYKKAPIFTSEHGEKLY
LVRALQGGSGGGSGSGTVEEAYKLALKLGISVEELLKLAEAAYYSGTTVEEAYKLALKL
GISVEELLKLAKAAYYSGTTVEEAYKLALKLGISVEELLKLAKAAYYSGTTVEEAYKLALK
LGISVEELLKLAEAAYYSGTTVEEAYKLALKLGISVEELLKLAKAAYYSGTTVEEAYKLAL
KLGISVEELLKLAKAAYYSGGSGGGSGGSGSEWYYGNVTRHQAECALNERGVEGDFL
IRDSESSPSDFSVSLKASGKNKHFKVQLVDNVYCIGQRRFHTMDELVEHYKKAPIFTSE
HGEKLYLVRALQGGSGGGSGSGTVEEAYKLALKLGISVEELLKLAEAAYYSGTTVEEA
YKLALKLGISVEELLKLAKAAYYSGTTVEEAYKLALKLG* (SEQ ID NO: 150).

Repetitive Sequences in SEQ ID NO: 150 forming α–helical structures include:

VEELLKLAKAAYYS (SEQ ID NO: 1);
VEEAYKLALKL (SEQ ID NO: 2); and
VEELLKLAEAAYYS (SEQ ID NO: 3.

Repetitive Sequences forming α–helical structures joined by linkers in SEQ ID NO: 150 include:

GISVEELLKLAKAAYYSGTTVEEAYKLALKL (SEQ ID NO: 73); and
GISVEELLKLAEAAYYSGTTVEEAYKLALKL (SEQ ID NO: 74).

Additional Linkers in SEQ ID NO: 150 include:

GGSGGGSGGSG (SEQ ID NO: 152); and
GGSGGGSGSG (SEQ ID NO: 153)

Functional Domains in SEQ ID NO: 150 include:

SEWYYGNVTRHQAECALNERGVEGDFLIRDSESSPSDFSVSLKASGKNKHFKVQLVD
NVYCIGQRRFHTMDELVEHYKKAPIFTSEHGEKLYLVRALQ (SEQ ID NO: 154)

SDS-PAGE

SEC

CD Spectra

FIG. 18F

MASSHHHHHHSSGLVPRGSSMGLDPEAIKAAAELGKAGISSEEILELLRAAHELGLDPE
AIKAAAELGKAGISSEEILELLRAAHELGLDPEAIKAAAELGKAGISSEEILELLRAAHELG
SGGGSGGSGAPTSSSTKKTQLQLEHLLLDLQMILNGINNYKNPKLTRMLTFKFYMPKK
ATELKHLQCLEEELKPLEEVLNLAQSKNFHLRPRDLISNINVIVLELKGSETTFMCEYAD
ETATIVEFLNRWITFCQSIISTLTGGSGGGSGSGGLDPEAIKAAAELGKAGISSEEILELL
RAAHELGLDPEAIKAAAELGKAGISSEEILELLRAAHELGLDPEAIKAAAELGKAGISSEE
ILELLRAAHELG (SEQ ID NO: 151).

Repetitive Sequences in SEQ ID NO: 151 forming α–helical structures include:

PEAIKAAAELGKA (SEQ ID NO: 124); and
SEEILELLRAAHEL (SEQ ID NO: 125).

Repetitive Sequences forming α–helical structures joined by linkers in SEQ ID NO: 151 include:

GLDPEAIKAAAELGKAGISSEEILELLRAAHEL (SEQ ID NO: 141).

Additional Linkers in SEQ ID NO: 150 include:

GGSGGGSGGSG (SEQ ID NO: 152); and
GGSGGGSGSG (SEQ ID NO: 153)

Functional Domains in SEQ ID NO: 150 include:

APTSSSTKKTQLQLEHLLLDLQMILNGINNYKNPKLTRMLTFKFYMPKKATELKHLQCL
EEELKPLEEVLNLAQSKNFHLRPRDLISNINVIVLELKGSETTFMCEYADETATIVEFLNR
WITFCQSIISTLT (SEQ ID NO: 155)

FIG. 19

|  | dTor_6x35L | dTor_6x35L (SeMet) | dTor_3x33L_2-2a | dTor_3x33L_2-2b | dTor_9x31L_2_sub | dTor_9x31L_2 | dTor_12x31L |
|---|---|---|---|---|---|---|---|
| Data collection | | | | | | | |
| Space group | C 2 2 21 | C 2 2 21 | P 21 21 21 | P 43 21 2 | P 43 21 2 | P 21 21 21 | C 2 |
| Cell dimensions | | | | | | | |
| a, b, c (Å) | 63.5, 85.3, 80.5 | 63.5, 85.1, 80.5 | 37.1, 68.6, 152.4 | 40.2, 40.2, 217.7 | 102.8, 102.8, 93.92 | 41.74, 72.02, 86.19 | 95.41, 19.37, 76.34 |
| α, β, γ (°) | 90.0, 90.0, 90.0 | 90.0, 90.0, 90.0 | 90.0, 90.0, 90.0 | 90.0, 90.0, 90.0 | 90.0, 90.0, 90.0 | 90.0, 90.0, 90.0 | 90.0, 110.9, 90.0 |
| Wavelength (Å) | 1.54 | 0.9794 | 1.54 | 1.54 | 1.00 | 1.54 | 1.54 |
| Resolution (Å) | 50.0-2.26 (2.30-2.26) | 50.0-2.18 (2.26-2.18) | 50.00-1.85 (1.90-1.85) | 50-2.78 (2.88-2.78) | 50.0-3.2 (3.3-3.2) | 50.0-2.50 (2.54-2.50) | 50.0-2.50 (2.54-2.50 |
| R-merge | 0.045 (0.159) | 0.059 (0.323) | 0.056 (0.500) | 0.048 (0.136) | 0.056 (0.461) | 0.079 (0.292) | 0.048 (0.298) |
| I/σI | 39.9 (13.8) | 29.7 (8.41) | 20.3 (4.34) | 27.0 (15.0) | 31.3 (6.48) | 30.4 (5.66) | 27.2 (3.7) |
| Chi^2 | 2.909 (2.994) | 1.047 (1.359) | 1.100 (0.906) | 1.184 (1.205) | 0.929 (0.880) | 1.267 (1.047) | 1.080 (1.046) |
| Completeness (%) | 98.1 (97.9) | 99.7 (99.2) | 90.6 (95.9) | 98.9 (98.2) | 100.0 (100.0) | 99.2 (91.2) | 98.9 (87.6) |

FIG. 19 cont'd

| | dTor_6x35L | dTor_6x35L (SeMet) | dTor_3x33L_2-2a | dTor_3x33L_2-2b | dTor_9x31L_2_sub | dTor_9x31L_2 | dTor_12x31L |
|---|---|---|---|---|---|---|---|
| Redundancy | 3.8 (3.6) | 13.7 (11.6) | 6.0 (7.0) | 12.3 (10.6) | 14.8 (15.1) | 10.0 (4.50) | 3.7 (3.0) |
| CC1/2 | - | (0.972) | (0.951) | (0.995) | (0.998) | (0.960) | (0.900) |
| Refinement | | | | | | | |
| Resolution (Å) | | 43.0-2.18 (2.23-2.18) | 76.2-1.85 (1.90-1.85) | 54.42-2.78 (2.85-2.78) | 29.95-3.2 (3.7-3.2) | 29.98-2.5 (2.6-2.5) | 30.6-2.5 (2.59-2.50) |
| No. reflections | | 11137 | 29249 | 4760 | 8662 | 9355 | 27183 |
| R-work | | 23.8 | 22.7 | 19.3 | 29.96 | 22.5 | 21.42 |
| R-free | | 29.6 | 28.2 | 26.7 | 34.5 | 32.8 | 25.4 |
| No. atoms | | | | | | | |
| Protein | | 1476 | 3038 | 1480 | 2292 | 2011 | 5608 |
| Ion | | - | 8 | - | - | - | - |
| Water | | - | 139 | 50 | - | - | 166 |
| B-factors | | | | | | | |
| Protein | | 43.7 | 36.6 | 26 | 108.2 | 35.9 | 42.1 |
| Ion | | - | 61 | - | - | - | - |
| Water | | - | 52.4 | 56 | - | - | 43.8 |
| R.m.s. deviations | | | | | | | |

FIG. 19 cont'd

|  | dTor_6x35L | dTor_6x35L (SeMet) | dTor_3x33L_2-2a | dTor_3x33L_2-2b | dTor_9x31L_2_sub | dTor_9x31L_2 | dTor_12x31L |
|---|---|---|---|---|---|---|---|
| Bond lengths (Å) |  | 0.0142 | 0.017 | 0.017 | 0.002 | 0.008 | 0.002 |
| Bond angles (°) |  | 1.6908 | 1.708 | 1.918 | 0.5 | 1.038 | 0.49 |
| Ramachandran |  |  |  |  |  |  |  |
| Preferred (%) |  | 98.06 | 99.48 | 98.96 | 98.31 | 99.28 | 99 |
| Allowed (%) |  | 1.94 | 0.00 | 0.52 | 1.69 | 0.36 | 0.0 |
| Outliers (%) |  | 0.00 | 0.52 | 0.52 | 0 | 0.36 | 1 |
| PDB ID |  | 4YXX | 4YY2 | 4YY5 | 4YXY | 4YXZ | 5BYO |

FIG. 23 dTor_9x31L_sub repeat_num= 3 repeat_len= 31 protein_len= 93 (SEQ ID NO: 51)

GISVEELLKLAKAAYYSGTTVEEAYKLALKLGISVEELLKLAEAAYYSGTTVEEAYKLA
LKLGISVEELLKLAKAA YYSGTTVEEAYKLALKL dTor_3x33L_1 repeat_num= 3 repeat_len= 33 protein_len= 99 (SEQ ID NO: 52)

GKSPTEALLKLIAEAKGITETEAKEEAEKALKEGKSPTEALLKLIAEAKGITETEAKEE
AEKALKEGKSPTEALLK LIAEAKGITETEAKEEAEKALKE dTor_3x33L_1-1 repeat_num= 3 repeat_len= 33 protein_len= 99 (SEQ ID NO: 53)

GKSPTEALLKLIAEAKGITSTEAKEEAIKALKEGKSPTEALLKLIAEAKGITELEAKVLA
EKALKEGKSPTEALLK LIAEAKGITETEAKLEAEKALKE dTor_3x33L_2 repeat_num= 3 repeat_len= 33 protein_len= 99 (SEQ ID NO: 54)

GKSPTEVLLELIAEASGTTKEEVKEKFLKELSKGKSPTEVLLELIAEASGTTKEEVKE
KFLKELSKGKSPTEVLLE LIAEASGTTKEEVKEKFLKELSK dTor_3x33L_2-1 repeat_num= 3 repeat_len= 33 protein_len= 99 (SEQ ID NO: 55)

GKSPTEVLLELIAEASGTTKEEVKRKFLKELSKGKSPTEVLLELIAEASGTTKAEVKR
EFLWELSLGKSPTEVLLE LIAEASGTTKEEVKEKFLAELEK dTor_3x33L_2-2 repeat_num= 3 repeat_len= 33 protein_len= 99 (SEQ ID NO: 56)

GKSPTEVLLELIAEASGTTREEVKEKFLKELRKGKSPTEVLLELIAEASGTTKEEVKE
KFLKELSFGKSPTEVLLE LIAEASGTTKEEVKKKFWKELSL dTor_3x33L_2-3 repeat_num= 3 repeat_len= 33 protein_len= 99 (SEQ ID NO: 57)

GKSPTEVLLELIAEASGTTKEEVKEKFLKELSKGKSPTEVLLELIAEASGTTKEEVKE
KFLKELSKGKSPTEVLLE LIAEASGTTKREVKRWFLFELRK dTor_3x33L_2-4 repeat_num= 3 repeat_len= 33 protein_len= 99 (SEQ ID NO: 58)

GKSPTEVLLELIAEASGTTKAEVKLKFLFELSFGKSPTEVLLELIAEASGTTKEEVKE
KFLKELFKGKSPTEVLLE LIAEASGTTKEEVKEKFLKELSK

FIG. 23 cont'd dTor_3x33L_3 repeat_num= 3 repeat_len= 33 protein_len= 99 (SEQ ID NO: 59)
G<u>YS</u>TTEALLILIAEAS<u>GTT</u>VEQQKQRFKELVKK<u>GYS</u>TTEALLILIAEAS<u>GTT</u>VEQQKQ
RFKELVKK<u>GYS</u>TTEALLI LIAEAS<u>GTT</u>VEQQKQRFKELVKK dTor_6x33R_1 repeat_num= 6 repeat_len= 33 protein_len= 198 (SEQ ID NO: 60)

<u>GD</u>KTAIAQILAIKASAK<u>GDE</u>TELERALRYAKKV<u>GDK</u>TAIAQILAIKASAK<u>GDE</u>TELERA
LRYAKKV<u>GDK</u>TAIAQILAIKASAK<u>GDE</u>TELERALRYAKKV<u>GDK</u>TAIAQILAIKASAK<u>GD</u>
ETELERALRYAKKV<u>GDK</u>TAIAQILAIKASAK<u>GDE</u>TELERALRYAKKV<u>GDK</u>TAIAQILAI
KASAK<u>GDE</u>TELERALRYAKKV dTor_6x33R_1-1 repeat_num= 6 repeat_len= 33 protein_len= 198 (SEQ ID NO: 61)

<u>GD</u>KTAIAQILAIKASAK<u>GDE</u>TELERALRYAVKV<u>GDK</u>TAIAQILAIKASAK<u>GDE</u>TELEQA
LRYAKFV<u>GDK</u>TAIAQILAIKASAK<u>GDE</u>LELTRALAYAKKV<u>GDK</u>TAIAQILAIKASAK<u>GD</u>
ETELERALRYAKLV<u>GDK</u>TAIAQILAIKASAK<u>GDE</u>TELERALRYAKYV<u>GDK</u>TAIAQILAI
KASAK<u>GDE</u>PELEYALAYAKKV dTor_6x33R_1-2 repeat_num= 6 repeat_len= 33 protein_len= 198 (SEQ ID NO: 62)

<u>GD</u>KTAIAQILAIKASAK<u>GDE</u>TELERALRYAKKV<u>GDK</u>TAIAQILAIKASAK<u>GDE</u>TELERA
LIFAEAV<u>GDK</u>TAIAQILAIKASAK<u>GDE</u>TELERALRYAKKV<u>NDK</u>TAIAQILAIKASAK<u>GDE</u>
TELDRALWYAKKV<u>GDK</u>TAIAQILAIKASAK<u>GDE</u>TELERALRYAKKV<u>GDK</u>TAIAQILAIK
ASAK<u>GDE</u>TELERALLYAKKV dTor_6x33R_1-3 repeat_num= 6 repeat_len= 33 protein_len= 198 (SEQ ID NO: 63)

<u>GD</u>KTAIAQILAIKASAK<u>GDE</u>TELERALRYAKKV<u>GDK</u>TAIAQILAIKASAK<u>GDE</u>TELERA
LAYARLV<u>GDK</u>TAIAQILAIKASAK<u>GDE</u>TELERALRYAEKV<u>GDK</u>TAIAQILAIKASAK<u>GD</u>
EQELEAALIYAKKV<u>GDK</u>TAIAQILAIKASAK<u>GDE</u>TELERALRYAKKV<u>GDK</u>TAIAQILAIK
ASAK<u>GDE</u>TELERALWYAKKV dTor_6x33R_2 repeat_num= 6 repeat_len= 33 protein_len= 198 (SEQ ID NO: 64)

<u>GD</u>RSAIATAYIALAEYL<u>GDK</u>EALLKAIEIAIKL<u>GDR</u>SAIAEAYIALARYL<u>GDK</u>EALLKAIE
IAIKL<u>GDR</u>SAIATAYIALAEYL<u>GDK</u>EALLKAIEIAIKL<u>GDR</u>SAIAEAYIALARYL<u>GDK</u>EAL
LKAIEIAIKL<u>GDR</u>SAIATAYIALAEYL<u>GDK</u>EALLKAIEIAIKL<u>GDR</u>SAIAEAYIALARYL<u>GD</u>
KEALLKAIEIAIKL

FIG. 23 cont'd dTor_6x33R_3 repeat_num= 6 repeat_len= 33 protein_len= 198 (SEQ ID NO: 65)

GDKSALAQILAIYASAYGDTTLFLRALKLAKEVGDKSALAQILAIYASAYGDTTLFLRALKLA
KEVGDKSALAQILAIYASAYGDTTLFLRALKLAKEVGDKSALAQILAIYASAYGDTTLFLRAL
KLAKEVGDKSALAQILAIYASAYGDTTLFLRALKLAKEVGDKSALAQILAIYASAYGDTTLFL
RALKLAKEV dTor_6x33R_4 repeat_num= 6 repeat_len= 33 protein_len= 198 (SEQ ID NO: 66)

GDLELYIRVLAIVAEAEGDKTKLELALKLALKKGDLKLYIEVLAIVAEAEGDKTKLELALKLAL
KKGDLELYIRVLAIVAKAEGDKTKLELALKLALKKGDLKLYIEVLAIVAEAEGDKTKLELALKL
ALKKGDLELYIRVLAIVAEAEGDKTKLELALKLALKKGDLKLYIEVLAIVAKAEGDKTKLELAL
KLALKK dTor_6x35L repeat_num= 6 repeat_len= 35 protein_len= 210 (SEQ ID NO: 67)

VSLEQALKILKVAAELGTTVEEAVKRALKLKTKLGVSLEQALKILEVAAELGTTVEEAVKRA
LKLKTKLGVSLEQALKILEVAAKLGTTVEEAVKRALKLKTKLGVSLEQALKILKVAAELGTTV
EEAVKRALKLKTKLGVSLEQALKILEVAAELGTTVEEAVKRALKLKTKLGVSLEQALKILEV
AAKLGTTVEEAVKRALKLKTKLG dTor_6x35L(SeMet) repeat_num= 6 repeat_len= 35 protein_len= 210 (SEQ ID NO: 68)

VSLEQALKILKVAAELGTTVEEAVKRALKLKTKLGVSLEQALKILEVAAELGTTVEEAVKRA
LKLKTKLGVSLEQALKILEVAAKLGTTVEEAVKRALKLKTKLGVSLEQALKILKVAAELGTTV
EEAVKRALKLKTKLGVSLEQALKILEVAAELGTTVEEAVKRAMKLKTKLGVSLEQALKILEV
AAKLGTTVEEAVKRALKLKTKLG dTor_9x31L repeat_num= 9 repeat_len= 31 protein_len= 279 (SEQ ID NO: 69)

GISVEELLKLAKAAYYSGTTVEEAYKLALKLGISVEELLKLAEAAYYSGTTVEEAYKLALKL
GISVEELLKLAKAAYYSGTTVEEAYKLALKLGISVEELLKLAKAAYYSGTTVEEAYKLALKL
GISVEELLKLAEAAYYSGTTVEEAYKLALKLGISVEELLKLAKAAYYSGTTVEEAYKLALKL
GISVEELLKLAKAAYYSGTTVEEAYKLALKLGISVEELLKLAEAAYYSGTTVEEAYKLALKL
GISVEELLKLAKAAYYSGTTVEEAYKLALKL

FIG. 23 cont'd dTor_12x31L repeat_num= 12 repeat_len= 31 protein_len= 372 (SEQ ID NO: 70)

GISVEELLKLAKAAYYSGTTVEEAYKLALKLGISVEELLKLAEAAYYSGTTVEEAYKLA
LKLGISVEELLKLAKAAYYSGTTVEEAYKLALKLGISVEELLKLAKAAYYSGTTVEEAY
KLALKLGISVEELLKLAEAAYYSGTTVEEAYKLALKLGISVEELLKLAKAAYYSGTTVE
EAYKLALKLGISVEELLKLAKAAYYSGTTVEEAYKLALKLGISVEELLKLAEAAYYSGT
TVEEAYKLALKLGISVEELLKLAKAAYYSGTTVEEAYKLALKLGISVEELLKLAKAAYY
SGTTVEEAYKLALKLGISVEELLKLAEAAYYSGTTVEEAYKLALKLGISVEELLKLAKA
AYYSGTTVEEAYKLALKL design_12x_insert_single (12 repeats w/ insert, 477 aas) (SEQ ID NO: 71)

GISVEELLKLAKAAYYSGTTVEEAYKLALKLGISVEELLKLAEAAYYSGTTVEEAYKLA
LKLGISVEELLKLAKAAYYSGTTVEEAYKLALKLGISVEELLKLAKAAYYSGTTVEEAY
KLALKLGISVEELLKLAEAAYYSGTTVEEAYKLALKLGISVEELLKLAKAAYYSGSGG
SEWYYGNVTRHQAECALNERGVEGDFLIRDSESSPSDFSVSLKASGKNKHFKVQL
VDNVYCIGQRRFHTMDELVEHYKKAPIFTSEHGEKLYLVRALQGSGGTVEEAYKLA
LKLGISVEELLKLAKAAYYSGTTVEEAYKLALKLGISVEELLKLAEAAYYSGTTVEEAY
KLALKLGISVEELLKLAKAAYYSGTTVEEAYKLALKLGISVEELLKLAKAAYYSGTTVE
EAYKLALKLGISVEELLKLAEAAYYSGTTVEEAYKLALKLGISVEELLKLAKAAYYSGT
TVEEAYKLALKLG> design_12x_insert_double (12 repeats w/ insert, 581 aas) (SEQ ID NO: 72)

GISVEELLKLAKAAYYSGTTVEEAYKLALKLGISVEELLKLAEAAYYSGTTVEEAYKLA
LKLGISVEELLKLAKAAYYSGTTVEEAYKLALKLGISVEELLKLAKAAYYSGSGGSEW
YYGNVTRHQAECALNERGVEGDFLIRDSESSPSDFSVSLKASGKNKHFKVQLVDN
VYCIGQRRFHTMDELVEHYKKAPIFTSEHGEKLYLVRALQGSGGTVEEAYKLALKLG
ISVEELLKLAEAAYYSGTTVEEAYKLALKLGISVEELLKLAKAAYYSGTTVEEAYKLAL
KLGISVEELLKLAKAAYYSGTTVEEAYKLALKLGISVEELLKLAEAAYYSGTTVEEAYK
LALKLGISVEELLKLAKAAYYSGTTVEEAYKLALKLGISVEELLKLAKAAYYSGSGGS
EWYYGNVTRHQAECALNERGVEGDFLIRDSESSPSDFSVSLKASGKNKHFKVQLV
DNVYCIGQRRFHTMDELVEHYKKAPIFTSEHGEKLYLVRALQGSGGTVEEAYKLAL
KLGISVEELLKLAEAAYYSGTTVEEAYKLALKLGISVEELLKLAKAAYYSGTTVEEAYK
LALKLG

SDS-PAGE

SEC

FIG. 24D

NLVPMVATV//GCGASGGGGSGGGGS//IQRTPKIQVYSRHPAENGKSNFLNCYVSGFH
PSDIEVDLLKNGERIEKVEHSDLSFSKDWSFYLLYYTEFTPTEKDEYACRVNHVTLSQP
KIVKWDRDM//GGGGSGGGGSGGGGSGGGGS//GSHSMRYFFTSVSRPGRGEPRFIA
VGYVDDTQFVRFDSDAASQRMEPRAPWIEQEGPEYWDGETRKVKAHSQTHRVDLGT
LRGCYNQSEAGSHTVQRMYGCDVGSDWRFLRGYHQYAYDGKDYIALKEDLRSWTAA
DMAAQTTKHKWEAAHVAEQLRAYLEGTCVEWLRRYLENGKETLQRTDAPKTHMTHH
AVSDHEATLRCWALSFYPAEITLTWQRDGEDQTQDTELVETRPAGDGTFQKWAAVVV
PSGQEQRYTCHVQHEGLPKPLTLRWEP//GGGGSGGGGS//PEAIKAAAELGKAGISSE
EILELLRAAHELGLDPEAIKAAAELGKAGISSEEILELLRAAHELGLDPEAIKAAAELGKA
GISSEEILELLRAAHELGLDPEAIKAAAELGKAGISSEEILELLRAAHELGLDPEAIKAAAE
LGKAGISSEEILELLRAAHELGLDPEAIKAAAELGKAGISSEEILELLRAAHELGLD//ENLY
FQ//GSHHHHHH  (SEQ ID NO: 167)

NLVPMVATV -- peptide (9 residues)  (SEQ ID NO: 166)

GCGASGGGGSGGGGS, GGGGSGGGGSGGGGSGGGGS, and GGGGSGGGGS - linkers per Fremont et al. (45 residues)  (SEQ ID NOs: 168, 169 and 161)

IQKTPQIQVYSRHPPENGKPNILNCYVTQFHPPHIEIQMLKNGKKIPKVEMSDMSFSKD
WSFYILAHTEFTPTETDTYACRVKHASMAEPKTVYWDRDM -- beta2-macroglobulin domain (99 residues)  (SEQ ID NO: 165)

GSHSMRYFFTSVSRPGRGEPRFIAVGYVDDTQFVRFDSDAASQRMEPRAPWIEQEG
PEYWDGETRKVKAHSQTHRVDLGTLRGYYNQSEAGSHTVQRMYGCDVGSDWRFLR
GYHQYAYDGKDYIALKEDLRSWTAADMAAQTTKHKWEAAHVAEQLRAYLEGTCVEWL
RRYLENGKETLQRTDAPKTHMTHHAVSDHEATLRCWALSFYPAEITLTWQRDGEDQT
QDTELVETRPAGDGTFQKWAAVVVPSGQEQRYTCHVQHEGLPKPLTLRWEP -- A2 alpha chain (276 residues)  (SEQ ID NO: 164)

PEAIKAAAELGKAGISSEEILELLRAAHELGLDPEAIKAAAELGKAGISSEEILELLRAAHE
LGLDPEAIKAAAELGKAGISSEEILELLRAAHELGLDPEAIKAAAELGKAGISSEEILELLR
AAHELGLDPEAIKAAAELGKAGISSEEILELLRAAHELGLDPEAIKAAAELGKAGISSEEIL
ELLRAAHELGLD  -- toroid repeats (198 residues) (SEQ ID NO: 170)

ENLYFQ//GSHHHHHH  -- Tev Protease Cleavage site // Poly-Histidine affinity tag
(SEQ ID NO: 171)

CIRCULAR TANDEM REPEAT PROTEINS

REFERENCE TO SEQUENCE LISTING

A computer readable text file, entitled SequenceListing.txt created on or about May 8, 2018, with a file size of ~156 KB, contains the Sequence Listing for this application and is hereby incorporated by reference in its entirety.

CROSS REFERENCE TO RELATED APPLICATION

This application claims priority to U.S. Provisional Patent Application No. 62/262,146 filed Dec. 2, 2015, the entire contents of which are incorporated by reference herein.

STATEMENT OF GOVERNMENT INTEREST

This invention was made with government support under grant numbers GM106117, GM049857, and GM115545 awarded by the National Institutes of Health. The government has certain rights in the invention.

FIELD OF THE DISCLOSURE

The present disclosure provides artificially designed circular tandem repeat proteins (cTRPs). The proteins are circular, handed, and include alpha-helical repeat proteins. The cTRPs have a number of uses as scaffolds for geometrically precise, arrayed presentation of cell-signaling and/or immune-related protein and peptide epitopes, as well as numerous other therapeutic, diagnostic, and nanotechnological uses.

BACKGROUND OF THE DISCLOSURE

Repeat proteins are formed by repetition of modular units of protein sub-structures. The overall structural architecture of repeat proteins is dictated by the internal geometry of the protein and the local packing of the repeat building blocks. These features are generated by underlying patterns of amino acid sequences, that themselves, are repetitive in nature.

Naturally existing repeat proteins play important biological roles as macromolecular binding and scaffolding domains, enzymes, and building blocks for the assembly of fibrous materials. The structure and identity of these repeat proteins are highly diverse, ranging from extended, superhelical folds that bind peptide, DNA, and RNA partners, to closed and compact conformations with internal cavities suitable for small molecule binding and catalysis.

SUMMARY OF THE DISCLOSURE

The current disclosure provides repeat proteins designed purely by geometric criteria defining the inter-repeat geometry, without reference to the sequences and structures of naturally existing repeat protein families. Because the design methodology did not rely on template sequence or structural information taken from natural repeat proteins, the resulting repeat proteins are unlike those seen in nature. More particularly, the designed repeat proteins have repetitive alpha ($\alpha$)-helical structures joined by linkers. The inter-repeat packing geometry is constrained so as to juxtapose the N- and C-termini creating circular architectures. Further, the $\alpha$-helical bundles of each circular $\alpha$-helical repeat protein can be either entirely left-handed or entirely right-handed. These proteins are self-folding, and have high thermostability and solubility. They are referred to herein as circular tandem repeat proteins, or "cTRPs" herein.

The disclosed cTRPs can have numerous uses as novel biomaterials. For example, the cTRPs have a number of uses as scaffolds for geometrically precise, arrayed presentation of cell-signaling and/or immune-related protein and peptide epitopes, as well as numerous other therapeutic, diagnostic, and nanotechnological uses. In particular embodiments, functional domains can be inserted between $\alpha$-helical sequences and/or linker sequences without significantly altering the cTRPs' engineered parameters (e.g., circular, handed, $\alpha$-helical repeats). The cTRPs can also be used as nanofilters.

DESCRIPTION OF THE FIGURES

The following nomenclature is used to reference specific cTRPs: "dTor_(number of structural repeats)×(number of amino acid residues within each structural repeat)(protein handedness)". For example, "dTor_3x33L" describes a designed cTRP protein including a single protein chain containing 3 repeats of 33 repetitive amino acids, wherein the helical bundles of that cTRP are entirely left-handed. In the case that a cTRP is assembled from multiple protein subunits that each contain a fraction of the total repeats in that cTRP, the nomenclature also may indicate the number of repeats in each subunit of a multimeric assemblage, and thereby can distinguish between multimeric cTRPs that contain the same total number of repeats. For example, "dTor_12x31L_sub3" describes an assembly of 4 identical protein subunits that each have 3 left-handed repeats, that come together to create a multimeric cTRP with 12 total repeats. In contrast, "dTor_12x31L_sub4" describes an assembly of 3 identical protein subunits that each have 4 repeats, that again come together to create a multimeric cTRP with 12 total repeats. See FIG. 6A for a depiction of these examples. In the case that a cTRP also contains additional functional protein domains fused to positions on its surface, the nomenclature may also indicate the presence of such domains. For example, "dTor_24x33L_sub6_IL2" describes an assembly of 4 identical protein subunits that each have 6 left-handed repeats, with an IL2 cytokine protein domain fused to each subunit. See FIG. 18A for a depiction of this example. Each structural repeat (also referred to herein as a repetitive $\alpha$-helical structure) includes an outer alpha (a) helix, an inner a helix, and at least one linker. In the following FIGs., representative design models are shown as cartoon representations as the chain proceeds from the N to C terminus.

FIGS. 1A-1E. Biophysical characterization of dTor_3× 33L. FIG. 1A: ribbon diagram of the design of dTor_3×33L, visualized from the top and the side of the designed protein repeats. FIG. 1B: SDS-PAGE electrophoretic analysis of purified dTor_3×33L. FIG. 10: Size Exclusion Chromatographic (SEC) separation and analysis of purified dTor_3× 33L. FIG. 1D: Circular Dichroism (CD) spectrum of purified dTor_3×33L at 22° and 95° C. FIG. 1E: Exemplary dTor_3× 33L used to generate data presented in FIGS. 1A-1D (SEQ ID NO: 117).

FIGS. 2A-2E. Biophysical characterization of dTor_6× 33R. FIG. 2A: ribbon diagram of the design of dTor_6×33R, visualized from the top and the side of the designed protein repeats. FIG. 2B: SDS-PAGE electrophoretic analysis of purified dTor_6×33R. FIG. 2C: Hydrodynamic radii of purified constructs, measured using dynamic light scattering (DLS), is indicated. FIG. 2D: Circular Dichroism (CD)

spectrum of purified dTor6_x33R at 22° and 95° C. FIG. 2E: Exemplary dTor_6×33R used to generate data presented in FIGS. 2A-2D (SEQ ID NO: 118).

FIGS. 3A-3E. Biophysical characterization of dTor_6× 35L. FIG. 3A: ribbon diagram of the design of dTor_6×35L, visualized from the top and the side of the designed protein repeats. FIG. 3B: SDS-PAGE electrophoretic analysis of purified dTor_6×35L. FIG. 3C: Size Exclusion Chromatographic (SEC) separation and analysis of purified dTor_6× 35L. FIG. 3D: Circular Dichroism (CD) spectrum of purified dTor_6×35L at 22° and 95° C. FIG. 3E: Exemplary dTor_6× 35L used to generate data presented in FIGS. 3A-3D (SEQ ID NO: 119).

FIGS. 4A-4E. Biophysical characterization of dTor_9× 31L. FIG. 4A: ribbon diagram of the design of dTor_9×31L, visualized from the top and the side of the designed protein repeats. FIG. 4B: SDS-PAGE electrophoretic analysis of purified dTor_9×31L. FIG. 4C: Size Exclusion Chromatographic (SEC) separation and analysis of purified dTor_9× 31L. FIG. 4D: Circular Dichroism (CD) spectrum of purified dTor_9×31L at 22° and 95° C. FIG. 4E: Exemplary dTor_9× 31L used to generate data presented in FIGS. 4A-4D (SEQ ID NO: 120).

FIGS. 5A-5E. Biophysical characterization of dTor_12× 31L FIG. 5A: ribbon diagram of the design of dTor_12×31L, visualized from the top and the side of the designed protein repeats. FIG. 5B: SDS-PAGE electrophoretic analysis of purified dTor_12×31L. FIG. 5C: Size Exclusion Chromatographic (SEC) separation and analysis of purified dTor_12× 31L. Hydrodynamic radii of purified constructs, measured using dynamic light scattering (DLS), is also indicated. FIG. 5D: Circular Dichroism (CD) spectrum of purified dTor_12× 31L at 22° and 95° C. FIG. 5E: Exemplary dTor_12×31L used to generate data presented in FIGS. 5A-5D (SEQ ID NO: 121).

FIGS. 6A-6E. Biophysical characterization of dTor_12× 31L_sub3 FIG. 6A: ribbon diagram of the design of dTor_12×31L_sub3, visualized from the top and the side of the designed protein repeats. FIG. 6B: SDS-PAGE electrophoretic analysis of purified dTor_12×31L_sub3. FIG. 6C: Size Exclusion Chromatographic (SEC) separation and analysis of purified dTor_12×31L_sub3. FIG. 6D: Circular Dichroism (CD) spectrum of purified dTor_12×31L_sub3 at 22° and 95° C. FIG. 6E: Exemplary dTor_12×31L_sub3 used to generate data presented in FIGS. 6A-6D (SEQ ID NO: 122).

FIGS. 7A-7E. Biophysical characterization of dTor_24× 33L (monomeric). FIG. 7A: ribbon diagram of the design of dTor_24×33L, visualized from the top and the side of the designed protein repeats. FIG. 7B: SDS-PAGE electrophoretic analysis of purified dTor_24×33L FIG. 7C: Size Exclusion Chromatographic (SEC) separation and analysis of purified dTor_24×33L. Hydrodynamic radii of purified constructs, measured using dynamic light scattering (DLS), is also indicated. FIG. 7D: Circular Dichroism (CD) spectrum of purified dTor_24×33L at 22° and 95° C. FIG. 7E: Exemplary dTor_24×33L used to generate data presented in FIGS. 7A-7D (SEQ ID NO: 123).

FIG. 8A: ribbon diagram of the design of dTor_24×33L, visualized from the top and the side of the designed protein repeats. FIG. 8B: Small Angle X-ray Scattering (SAXS) analysis of dTor_24× 33L, indicating a close agreement between the theoretical scattering curve calculated from the designed protein model, to the experimentally measured scattering curve determined with purified protein. The close superposition of the two curves indicates that the overall dimensions and molecular surface describing the design and the actual structure are extremely similar.

FIGS. 9A-9E. Biophysical characterization of four separate multimeric assemblages of dTor_24×33L_sub("n"). FIG. 9A: SDS Page electrophoretic analyses of four purified versions of dTor_24×33L, in which each construct is assembled from multiple protein subunits that harbor either 8 repeats (Sub8'), 6 repeats (Sub6'), 4 repeats (Sub4') or 3 repeats (Sub3'). FIG. 9A: composite of two separate regions of one gel. FIG. 9B: ribbon diagram of dTor_24×33L, in which the straight lines indicate that these constructs include multimeric assemblages of protein subunits that each contain 8, 6, 4 or 3 identical peptide repeats. FIG. 9C: Size Exclusion Chromatographic (SEC) separation and analysis of purified dTor_24×33L multimers. Hydrodynamic radii of purified constructs, measured using dynamic light scattering (DLS), is also indicated. FIG. 9D: Circular Dichroism (CD) spectrum of purified dTor_24×33Lx multimers at 22° and 95° C. FIG. 9E: Exemplary sequences used to generate the data presented in FIGS. 9A-9D (SEQ ID NOs: 135-138).

FIGS. 10A-10D. Biophysical characterization of dTor_9× 57L. FIG. 10A: ribbon diagram of the design of dTor_9× 57L_, visualized from the top and the side of the designed protein repeats. FIG. 10B: SDS-PAGE electrophoretic analysis of purified dTor_9×57L FIG. 10C: Size Exclusion Chromatographic (SEC) separation and analysis of purified dTor_9×57L. Hydrodynamic radii of purified constructs, measured using dynamic light scattering (DLS), is also indicated. FIG. 10D: Exemplary dTor_9×57L used to generate the data presented in FIGS. 10A-10C (SEQ ID NO: 145).

FIG. 12. A comparison of a designed left-handed cTRP versus a naturally occurring right-handed α-toroidal protein. Design dTor_12×31L, shown on the left, has an entirely left-handed helical bundle, which can be seen by observing the left-handed twist of the polypeptide chain as it wraps around the axis of the helical bundle. The native toroid on the right, which has a right-handed bundle, is taken from the PDB structure 4ADY and corresponds to the PC repeat domain of the 26S proteasome subunit Rpn2 (He, et al., Structure 20, 513-521, (2012)). Note that this protein domain is not self-folding on its own and does not include repetitive α-helical structures as defined herein.

FIG. 13. Characterization of Designed Constructs.

FIG. 15. Geometrical properties of the most common short α-helical linkers in the structural database.

FIGS. 16A-16E. Functional (peptide-binding) characterization of dTor_12×31L_SH2_single (12× scaffold containing 1 SH2 domain). FIG. 16A: SDS-PAGE electrophoretic analysis of purified dTor_12×31L SH2_single (corresponding to a monomeric cTRP containing 12 repeats, interrupted within repeat #3 by an SH2 domain derived from the human Nck2 adapter protein). FIG. 16B: ribbon diagram of the design of dTor_12×31L SH2_single, visualized from the top and the side of the designed protein repeats. FIG. 16C: Size Exclusion Chromatographic (SEC) separation and analysis of purified dTor_12×31L_SH2_single. Hydrodynamic radii of purified constructs, measured using dynamic light scattering (DLS), is also indicated. FIG. 16D: Binding of peptide corresponding to sequence by dTor_12×31L_SH2_single. Binding measured by monitoring Fluorescence Anisotropy signal from a labeled peptide as a function of increasing protein concentration. Curve labeled "12×" corresponds to a negative control in which a non-functionalized dTor_12×31L construct (lacking any inserted SH2 domain) is shown to not bind the same peptide sequence. The peptide construct includes an N-terminal FITC fluorescent label, followed by a linker of composition "NH2-(CH2)5-CO2", followed by the target sequence for the SH2 domain (EHIpYDEVAAD (SEQ ID NO: 159)). FIG. 16E: Exemplary dTor_12×31L_SH2_single used to generate data presented in FIGS. 16A-16D (SEQ ID NO: 149).

FIGS. 17A-17E. Functional (peptide-binding) characterization of dTor_12×31L_SH2_double (12× scaffold containing 2 SH2 domains). FIG. 17A: SDS-PAGE electrophoretic analysis of purified dTor_12×31L_SH2_double (corresponding to a monomeric cTRP containing 12 repeats, interrupted within repeats #4 and 10 by an SH2 domain derived from the human Nck2 adapter protein). FIG. 17B: ribbon diagram of the design of dTor_12×31L_SH2_single, visualized from the top and the side of the designed protein repeats. FIG. 17C: Size Exclusion Chromatography (SEC) separation and analysis of purified dTor_12×31L_SH2_single. Hydrodynamic radii of purified constructs, measured using dynamic light scattering (DLS), is also indicated. FIG. 17D: Binding of peptide corresponding to sequence by dTor_12×31L_SH2_single. Binding measured by monitoring Fluorescence Anisotropy signal from a labeled peptide as a function of increasing protein concentration. Curve labeled "12×" corresponds to a negative control in which a non-functionalized dTor_12×31L construct (lacking any inserted SH2 domain) is shown to not bind the same peptide sequence. The peptide construct includes an N-terminal FITC fluorescent label, followed by a linker of composition "NH2-(CH2)5-CO2", followed by the target sequence for the SH2 domain (SEQ ID NO: 159). FIG. 17E: Exemplary dTor_12×31L_SH2_double used to generate data presented in FIGS. 17A-17D (SEQ ID NO: 150).

FIGS. 18A-18F. Biophysical characterization of dTor_24×33L_sub6_IL2 (24× scaffold containing 4 IL-2 cytokines). FIG. 18A: ribbon diagram of the design of dTor_24×33L_sub6_IL2, visualized from the side and the top of the designed protein repeats. FIG. 18B: SDS-PAGE electrophoretic analysis of purified dTor_24×33L_sub6_IL2 (corresponding to a cTRP including 24 repeats, including 4 identical chains containing a single IL-2 cytokine domain followed by 6 identical repeat peptide sequences). FIG. 18C: Size Exclusion Chromatographic (SEC) separation and analysis of purified dTor_24×33L_sub6_IL2. Hydrodynamic radii of purified constructs, measured using dynamic light scattering (DLS), is also indicated. FIG. 18D: CD spectra of purified dTor_24×33L_sub6_IL2, at 22° and 95° C. FIG. 18E: Stimulation of growth and viability of IL-2 responsive human CTLL-2 cell line by purified dTor_24×33L_sub6_IL2. FIG. 18F: Exemplary dTor_24×33L_sub6_IL2 used to generate data presented in FIGS. 18A-18E (SEQ ID NO: 151).

FIG. 19. Crystallographic data and refinement statistics for representative designed cTRPs.

FIG. 22A: Electron difference density for construct dTor_6×35L. The left panel shows anomalous difference Fourier peaks calculated from data collected from a crystal of selenomethionine-derivatized protein. Although only one methionine residue (at position 168) is present in the construct, strong anomalous difference peaks (I/σI greater than 4.0) are observed at equivalent positions within at least 3 modular repeats. The right panel shows difference density extending across the modeled position of the N- and C-termini in the refined model, indicating partial occupancy at that position by a peptide bond. The other five equivalent positions around the toroidal protein structure display equivalent features of density, indicating that each position is occupied by a mixture of loops and protein termini. FIG. 22B: Electron density for construct dTor_12×31L, again calculated at a position corresponding to the refined N- and C-termini in the crystallographic model. As was observed for the hexameric toroid in FIG. 22A, the electron density indicates a mixture of loops and protein termini.

FIG. 23. Exemplary repetitively patterned amino acid sequences (SEQ. ID NOs. 51-70) generating repeat structures are shown. GBB linker sequences are underlined and found between sequences generating outer and inner α helices. SEQ ID NOs. 71 and 72 represent sequences with functional domains inserted.

FIGS. 24A-24D. Biophysical characterization of dTor_24×L_sub6_scMHC. FIG. 24A: ribbon diagram of the design of dTor_24×L_sub6_scMHC, visualized from the top and the side of the designed protein repeats. FIG. 24B: SDS-PAGE electrophoretic analysis of purified dTor_24×L_sub6_scMHC. FIG. 24C: Size Exclusion Chromatographic (SEC) separation and analysis of purified dTor_24×L_sub6_scMHC. FIG. 24D: Exemplary dTor_24×L_sub6_scMHC used to generate data presented in FIGS. 1A-1D (SEQ ID NO: 167).

DETAILED DESCRIPTION

Figure 3A:
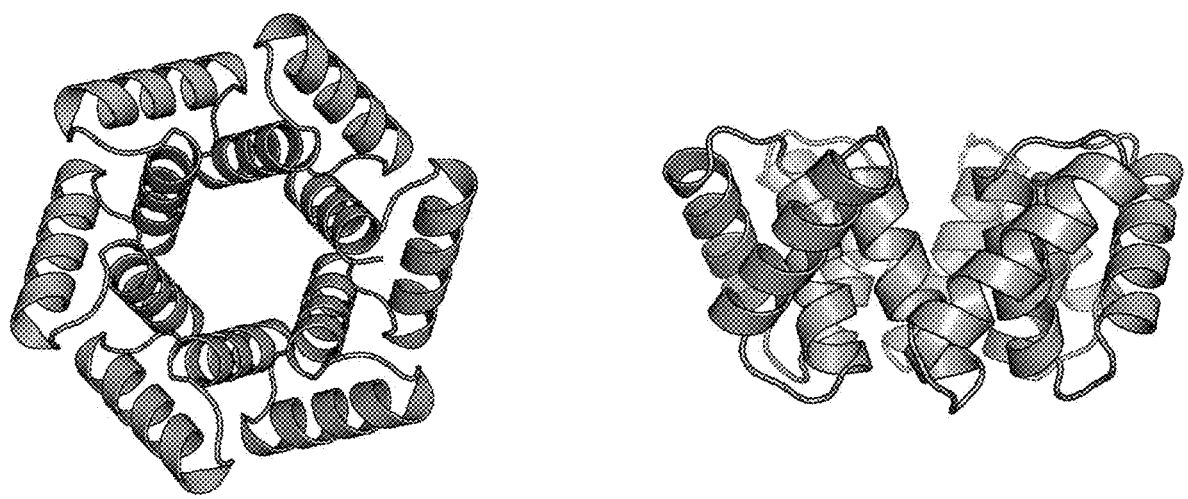
Figure 3B:
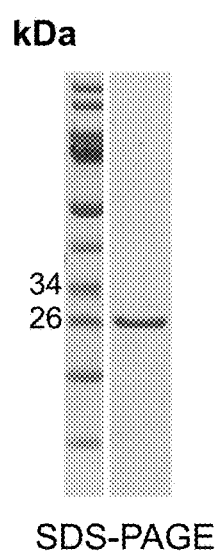
Figure 3C:
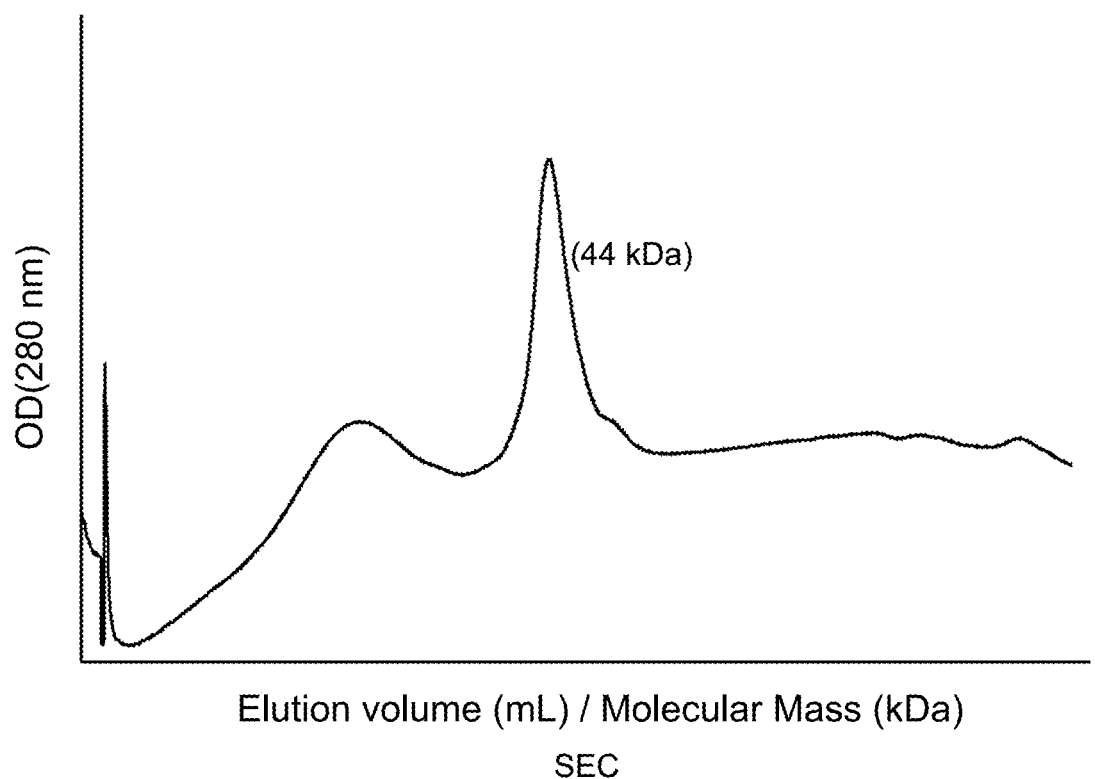
Figure 3D:
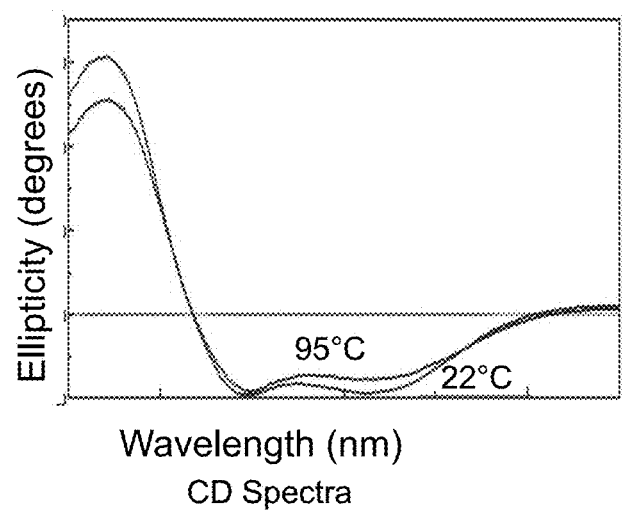
Figure 4A:
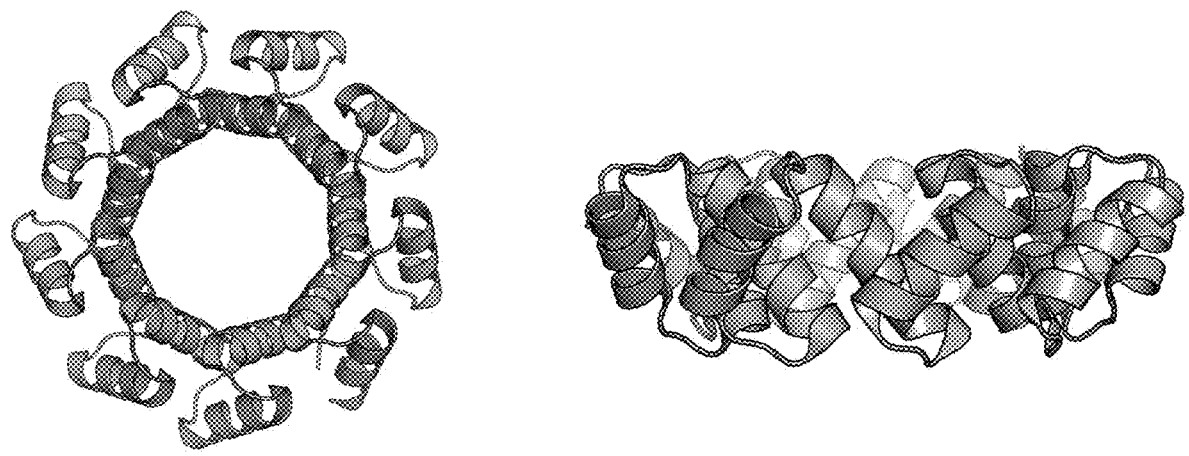
Figure 4B:
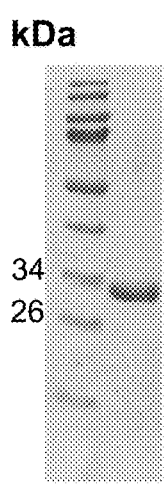
Figure 4C:
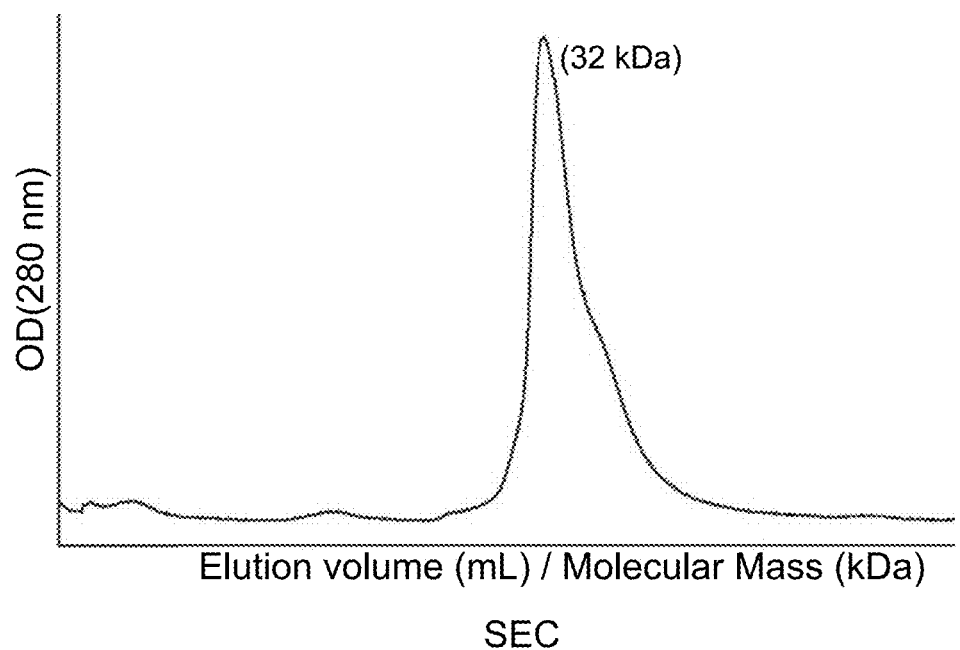
Figure 4D:
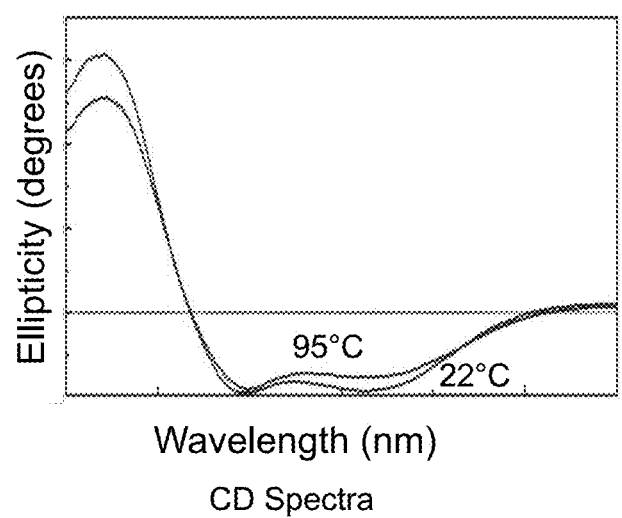
Figure 5A:
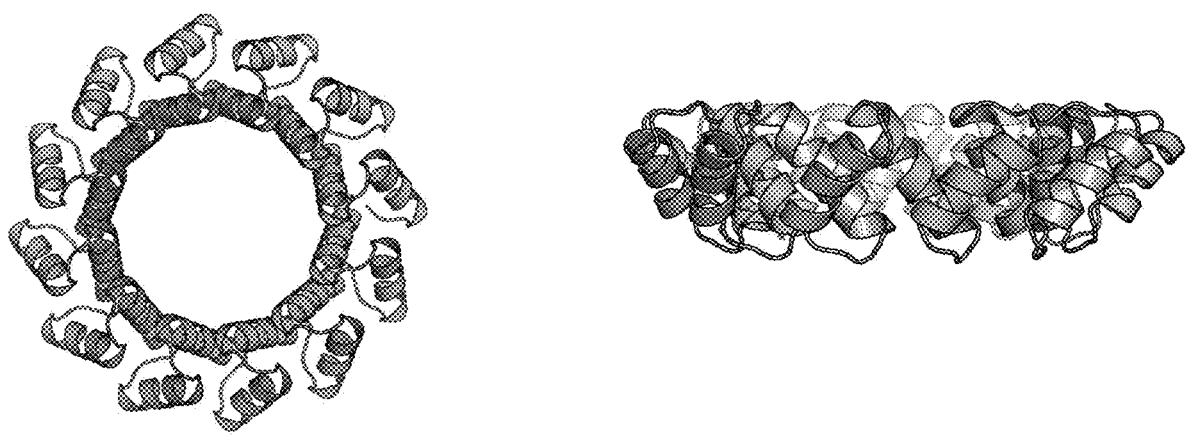
Figure 5B:
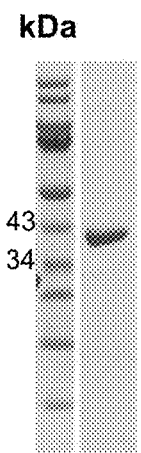
Figure 5C:
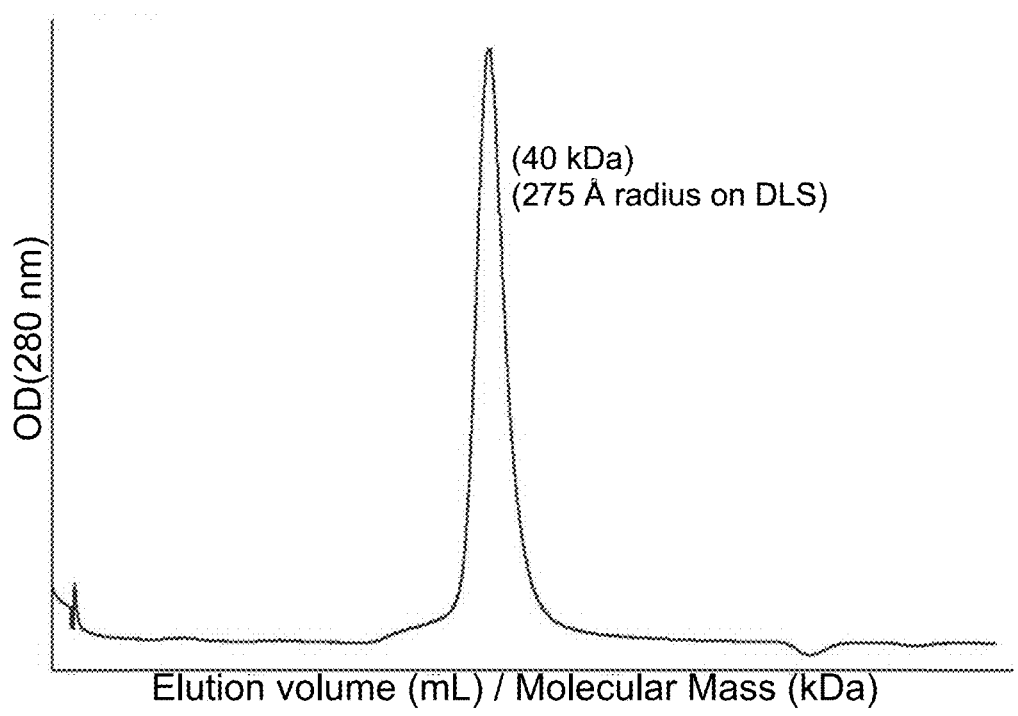
Figure 5D:
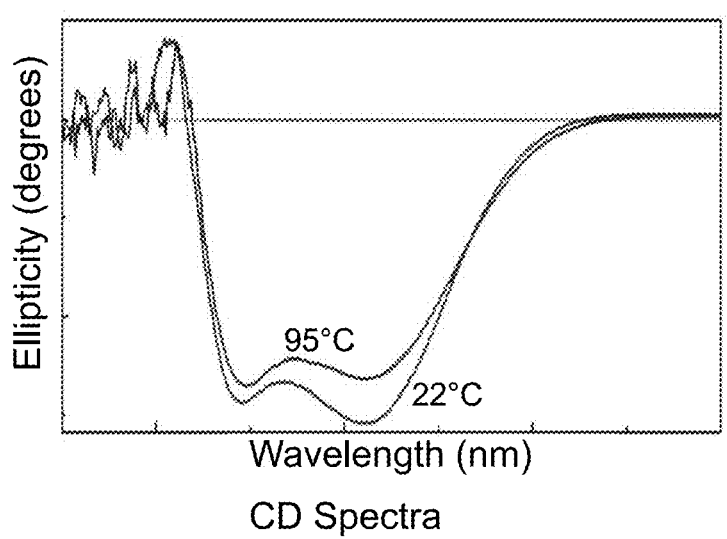
Figure 6A:
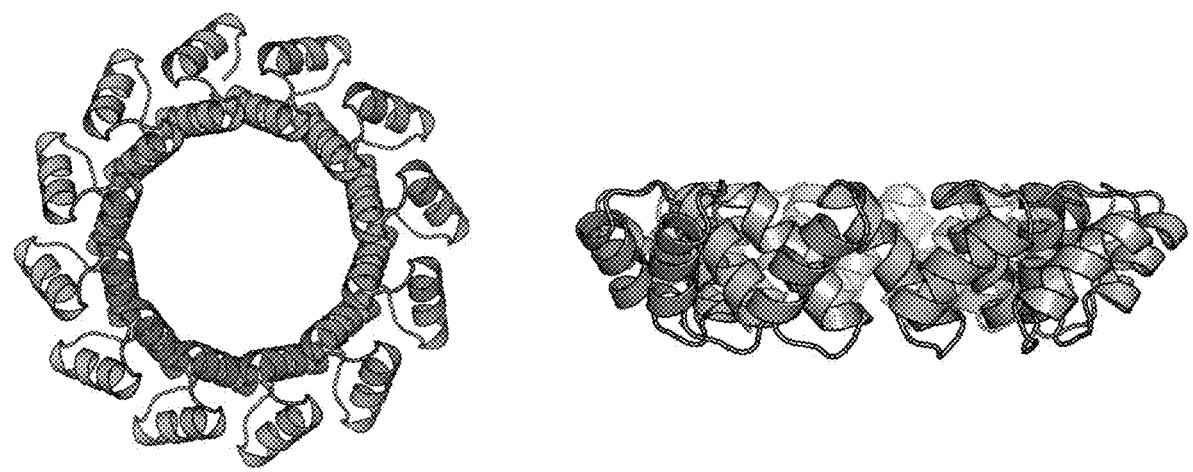
Figure 6B:
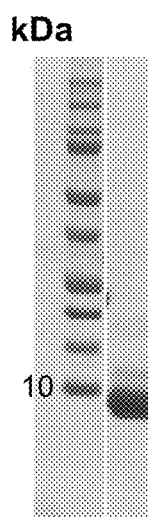
Figure 6C:
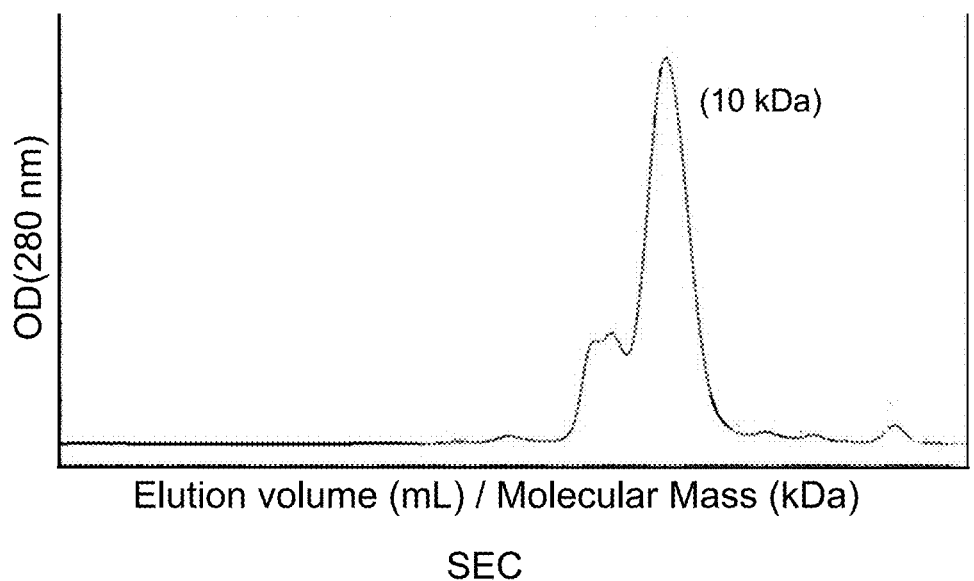
Figure 6D:
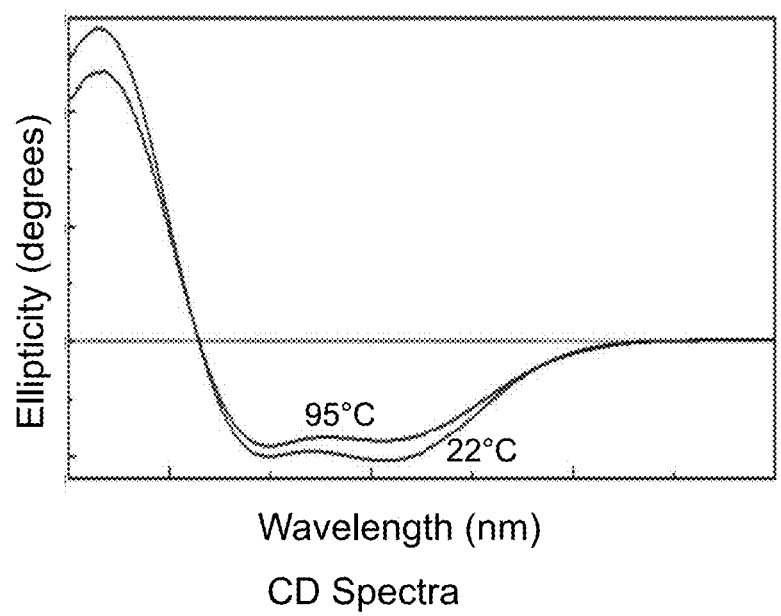
Figure 7A:
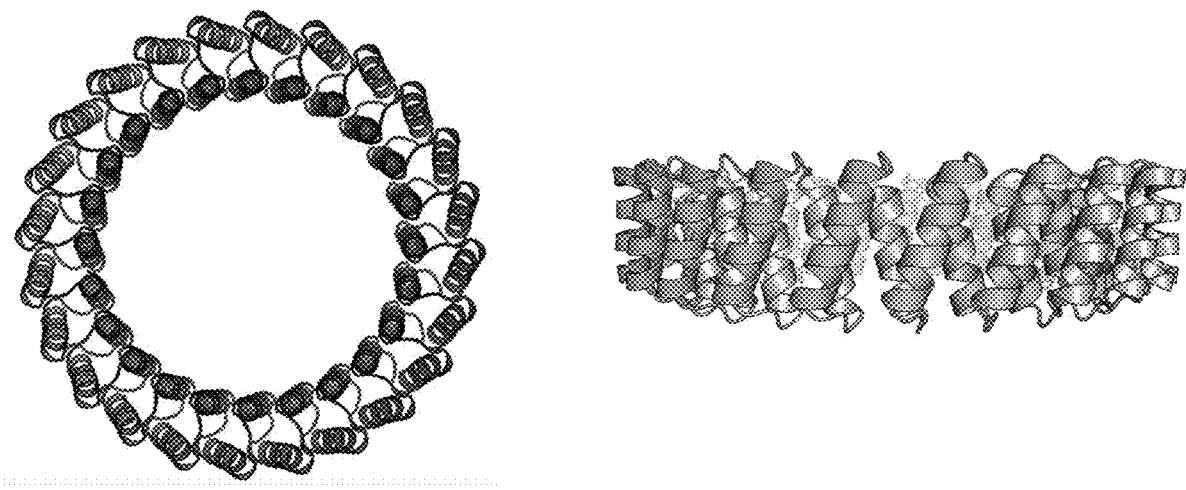
Figure 7B:
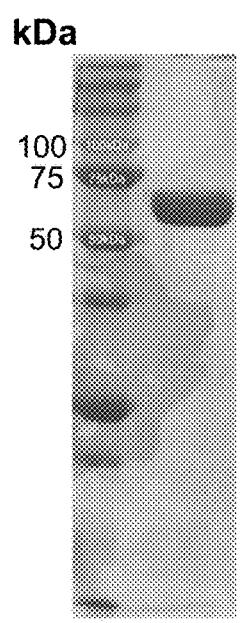
Figure 7C:
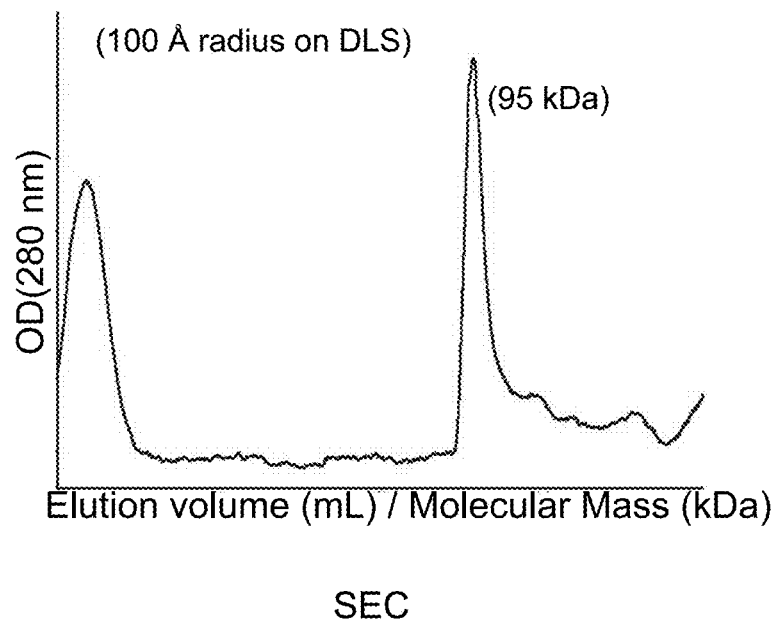
Figure 7D:
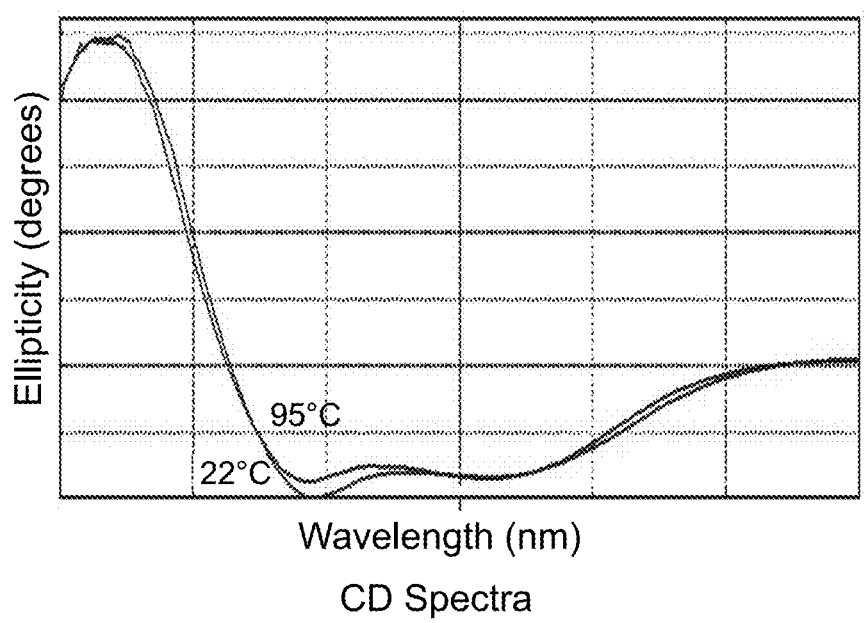

Repeat proteins are formed by repetition of modular units of protein sub-structures. The overall structural architecture of repeat proteins is dictated by the internal geometry of the protein and the local packing of the repeat building blocks. These features are generated by underlying patterns of amino acid sequences, that themselves, are repetitive in nature.

Naturally existing repeat proteins play important biological roles as macromolecular binding and scaffolding domains, enzymes, and building blocks for the assembly of fibrous materials. The structure and identity of these repeat proteins are highly diverse, ranging from extended, super-helical folds that bind peptide, DNA, and RNA partners, to closed and compact conformations with internal cavities suitable for small molecule binding and catalysis.

The current disclosure provides circular tandem repeat proteins (cTRPs) designed purely by geometric criteria defining the inter-repeat geometry, without reference to the sequences or the structures of naturally existing repeat protein families. Because the design methodology did not rely on template sequence or structural information taken from natural repeat proteins, the resulting cTRPs are unlike those seen in nature. More particularly, the designed cTRPs have highly repetitive α-helical structures joined by linkers. The inter-repeat packing geometry is constrained so as to juxtapose the N- and C-termini creating circular architectures. Further, the repeated domains including the circular α-helical repeat proteins are uniformly handed. These proteins are capable of independently self-folding, and have high thermostability and solubility.

The disclosed cTRPs can have numerous uses as novel biomaterials. For example, the cTRPs have a number of uses as scaffolds for geometrically precise, arrayed presentation of cell-signaling and/or immune-related protein and peptide epitopes, as well as numerous other therapeutic, diagnostic, and nanotechnological uses. In particular embodiments, functional domains can be inserted between or within α-helical sequences and linker sequences without significantly altering the cTRPs' engineered parameters (e.g., circular, handed, α-helical repeats). The cTRPs can also be used as nanofilters. The cTRPs, methods of generation, characteristics, and uses are now described in more detail.

cTRPs disclosed herein include repetitive α-helical structures joined by linkers. Referring to, for example, FIGS. 1A, 2A, 3A, 4A, 5A, 6A, 7A, 8A, 9B, 10A, and 12, each repetitive α-helical structure includes an outer α-helix and an inner α-helix. In particular embodiments, an α-helical structure is repetitive (e.g., structurally repetitive) when following (i) stacking with an adjacent α-helical structure; and (ii) comparison using root-mean-square-deviation (RMSD), the distance between corresponding atoms of the stacked outer α-helices and the stacked inner α-helices is within 2 angstrom (Å); within 1.5 Å; within 1 Å; within 0.5 Å; within 0.4 Å; or within 0.2 Å.

Exemplary amino acid sequences that generate an α-helix include VEELLKLAKAAYYS (SEQ ID NO: 1); VEEAYKLALKL (SEQ ID NO: 2); VEELLKLAEAAYYS (SEQ ID NO: 3); PTEALLKLIAEAK (SEQ ID NO: 4); ETEAKEEAEKALKE (SEQ ID NO: 5); STEAKEEAIKALKE (SEQ ID NO: 6); ELEAKVLAEKALKE (SEQ ID NO: 7); ETEAKLEAEKALKE (SEQ ID NO: 8); PTEVLLELIAEAS (SEQ ID NO: 9); KEEVKEKFLKELSK (SEQ ID NO: 10); KEEVKRKFLKELSK (SEQ ID NO: 11); KAEVKREFLWELSL (SEQ ID NO: 12); KEEVKEKFLAELEK (SEQ ID NO: 13); REEVKEKFLKELRK (SEQ ID NO: 14); KEEVKEKFLKELSF (SEQ ID NO: 15); KEEVKKKFWKELSL (SEQ ID NO: 16); KREVKRWFLFELRK (SEQ ID NO: 17); KAEVKLKFLFELSF (SEQ ID NO: 18); KEEVKEKFLKELFK (SEQ ID NO: 19); TTEALLILIAEAS (SEQ ID NO: 20); VEQQKQRFKELVKK (SEQ ID NO: 21); TAIAQILAIKASAK (SEQ ID NO: 22); TELERALRYAKKV (SEQ ID NO: 23); TELERALRYAVKV (SEQ ID NO: 24); TELEQALRYAKFV (SEQ ID NO: 25); LELTRALAYAKKV (SEQ ID NO: 26); TELERALRYAKLV (SEQ ID NO: 27); TELERALRYAKYV (SEQ ID NO: 28); PELEYALAYAKKV (SEQ ID NO: 29); TELERALIFAEAV (SEQ ID NO: 30); TELDRALWYAKKV (SEQ ID NO: 31); TELERALLYAKKV (SEQ ID NO: 32); TELERALAYARLV (SEQ ID NO: 33); TELERALRYAEKV (SEQ ID NO: 34); TELERALWYAKKV (SEQ ID NO: 35); SAIATAYIALAEYL (SEQ ID NO: 36); EALLKAIEIAIKL (SEQ ID NO: 37); SAIAEAYIALARYL (SEQ ID NO: 38); SALAQILAIYASAY (SEQ ID NO: 39); TLFLRALKLAKEV (SEQ ID NO: 40); ELYIRVLAIVAEAE (SEQ ID NO: 41); TKLELALKLALKK (SEQ ID NO: 42); KLYIEVLAIVAEAE (SEQ ID NO: 43); ELYIRVLAIVAKAE (SEQ ID NO: 44); KLYIEVLAIVAKAE (SEQ ID NO: 45); LEQALKILKVAAEL (SEQ ID NO: 46); VEEAVKRALKLKTKL (SEQ ID NO: 47); LEQALKILEVAAEL (SEQ ID NO: 48); LEQALKILEVAAKL (SEQ ID NO: 49); VEEAVKRAMKLKTKL (SEQ ID NO: 50); as well as SEQ ID NO: 124-129; 139, 140, 146 and 147.

Each repetitive α-helical structure includes 2 sequences that form an α helix. The two sequences forming a helices within each repetitive structure can be identical or can have at least 99%, at least 98%, at least 97%, at least 96%, at least 95%, at least 94%, at least 93%, at least 92%, at least 91%, at least 90% or at least 85% sequence identity to the other within the structure. Thus, in particular embodiments, a repetitive α-helical structure of a cTRP disclosed herein would include at least two sequences from SEQ ID NOs. 1-50; 124-129; 139, 140, 146 and 147 to generate an outer α helix and an inner α helix, respectively.

Disclosed engineered cTRPs that contain a circular architecture represent a target for rational, geometry-guided design of structural repeats for several reasons. Closure results from simple constraints on the inter-repeat geometry: if the transformation between successive repeats is considered as being composed of a rotation (curvature) about an axis together with a translation (rise) parallel to that axis, then the rise must equal zero and the curvature multiplied by the number of repeats must equal 360°. Circular structures are stabilized by interactions between the first and last repeats, obviating the need for capping repeats to maintain solubility and making them more tolerant than open repeat architectures to imperfections in the designed geometry. Thus, in particular embodiments, a circular protein (e.g., a protein having a circular architecture) is one wherein the N-terminal and C-terminal ends of the protein are naturally found within 10 Å following expression and folding. In particular embodiments, a circular protein is one wherein the N-terminal and C-terminal ends of the protein are naturally found within 10 Å; within 9 Å; within 8 Å; within 7 Å; within 6 Å; within 5 Å; within 4 Å; within 3 Å; within 2 Å; within 1 Å; or within 0.5 Å; following expression and folding. Naturally found means that the cTRP is self-folding. In particular embodiments, a circular protein is one designated as such by the teachings of Kajava, A. V. Tandem repeats in proteins: from sequence to structure. J. Struct. Biol. 179, 279-288, doi:10.1016/j.jsb.2011.08.009 (2012).

cTRPs offer the advantages of rotational symmetry (for example, in generating higher-order assemblies) with the added control provided by a covalent linkage between subunits. Conversely, and as described in more detail elsewhere herein, it is possible to convert a monomeric cTRP array into a symmetrical protein assembly by truncation (for example, converting a toroidal protein containing 'n' repeats into an equivalent homodimeric assembly containing 'n/2' repeats per subunit) if economy of protein length is required.

Figure 11:
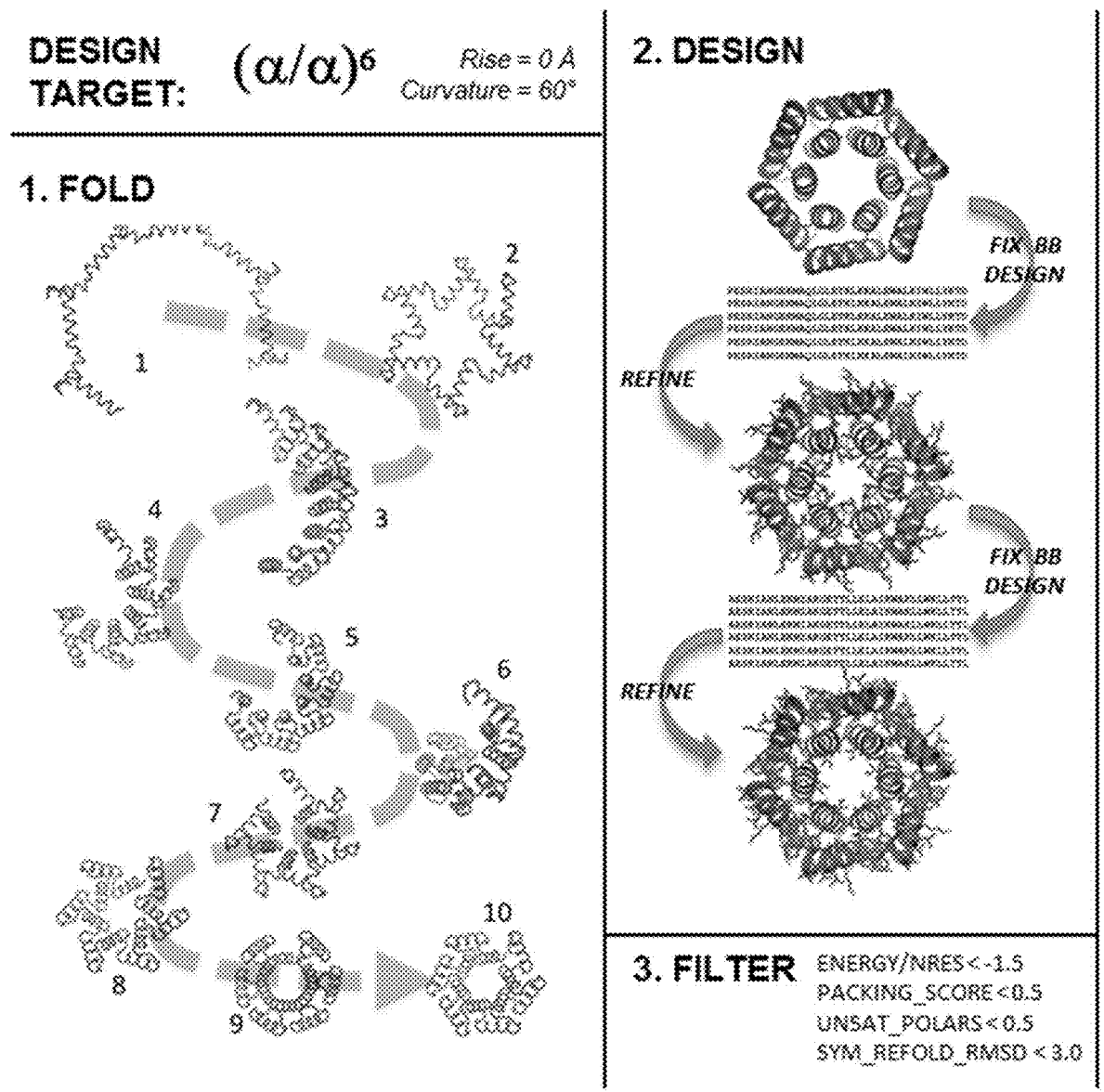
FIG. 11. Overview of the repeat module design process. Given a design target including secondary structure types, repeat number, and desired inter-repeat geometry, the main steps of the design methodology were (1) fragment assembly to generate starting backbone conformations; (2) all-atom sequence design and structure relaxation; (3) filtering to eliminate designs with poor packing, buried unsatisfied polar atoms, or low sequence structure compatibility; (4) clustering to identify recurring packing arrangements; (5) intensified sampling of architectures identified in the clustering step; and (6) final design assessment by large-scale re-prediction of the designed structure starting from the designed sequence. Design cluster identifiers (e.g., 14H-GBB-15H-GBB) record the length of the α-helices (14H and 15H) and the backbone conformations of the connecting loops (using a coarse-grained 5-state Ramachandran alphabet; Wintjens, et al., J Mol Biol 255, 235-253, (1996)).

To generate the cTRPs disclosed herein, an approach to geometry-guided repeat protein design (FIG. 11) that was implemented in the Rosetta molecular modeling package (Leaver-Fay, et al., Methods Enzymol. 487, 545-574, (2011)) and builds on published de novo design methodologies (Koga, et al., Nature 491, 222-227, (2012)) was developed. Key features include symmetry of backbone and side chain conformations extended across all repeats (allowing computational complexity to scale with repeat length rather than protein length); a pseudo-energy term that favors the desired inter-repeat geometry; clustering and resampling stages that allow intensified exploration of promising topologies; and an in silico validation step that assesses sequence-structure compatibility by attempting to re-predict the designed structure given only the designed sequence. Applying this design procedure produced a diverse array of toroidal structures (FIG. 11).

Designs with left-handed bundles (e.g., left-handed proteins; FIG. 12) were the primary focus because, as described elsewhere herein, this architecture (circular, left-handed α-helical) appears to be absent from all protein structural databases. In particular embodiments, to compute the handedness of helical bundles formed by cTRPs, an approximate helical bundle axis curve can be generated by joining the location of repeat-unit centers of mass in a sliding fashion along the protein chain. The handedness can then be determined by computing the directionality of the winding of the polypeptide chain about this axis curve. In particular embodiments, a left-handed protein is one wherein the protein is designated as such by the teachings of Kajava, A. V. Tandem repeats in proteins: from sequence to structure. J. Struct. Biol. 179, 279-288, doi:10.1016/j.jsb.2011.08.009 (2012).

Six monomeric repeat architectures have been initially selected for experimental characterization: a left-handed 3-repeat family (dTor_3×33L: designed Toroid with three 33-residue repeats, left-handed (FIGS. 1A-1E)), right- and left-handed 6-repeat families (dTor_6×33R (FIGS. 2A-2E) and dTor_6×35L (FIGS. 3A-3E)), a left-handed 9-repeat family (dTor_9×31L (FIGS. 4A-4E)), a left-handed 12-repeat design built by extending one of the 9-repeat designs by 3 repeats (dTor_12×31L (FIGS. 5A-5E)), and a left-handed 24-repeat design (dTor_24×33L). To enhance the likelihood of successful expression, purification, and crystallization, multiple designed sequences for some families were pursued, including a round of surface mutants for three designs that were refractory to crystallization (FIG. 13).

Figure 8A:
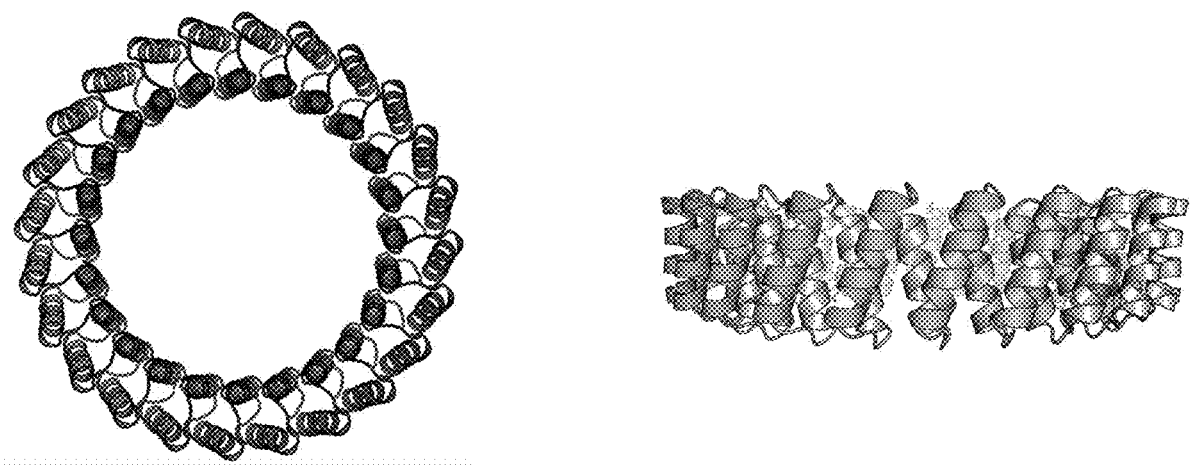
FIGS. 8A and 8B. Small Angle X-ray Scattering (SAXS) analysis of dTor_24×33L (monomeric).
Figure 8B:
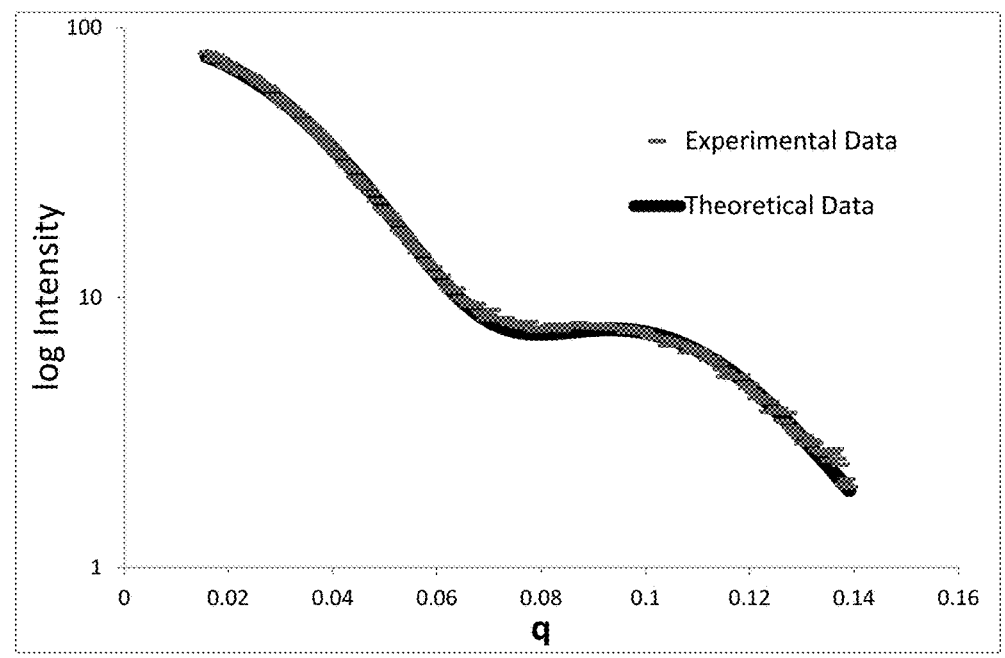
Figure 22A:
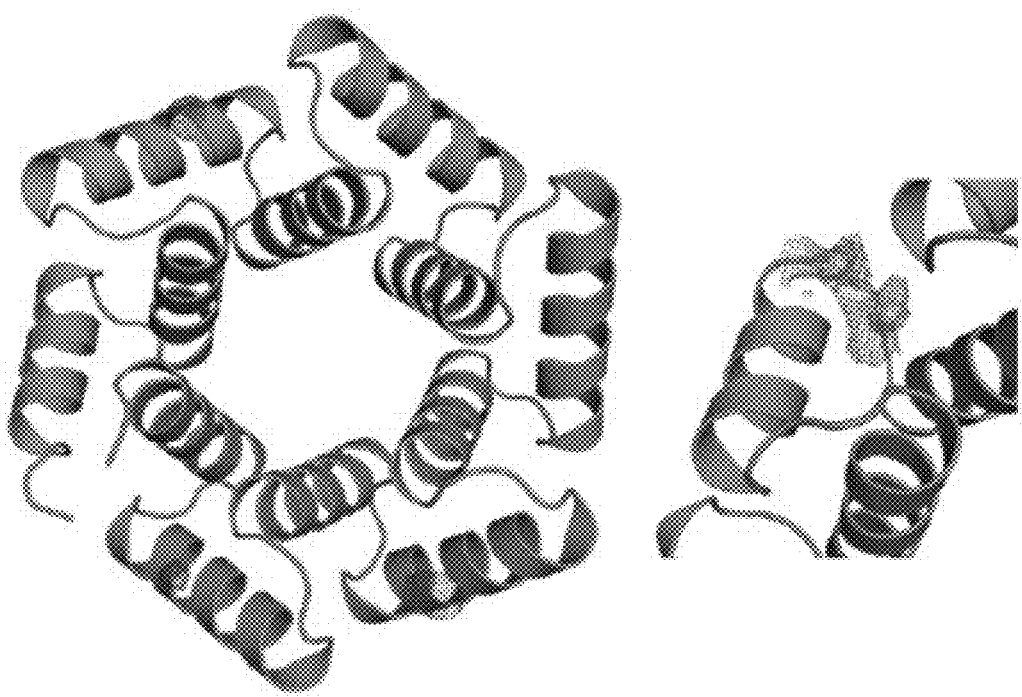
FIGS. 22A and 22B. The crystallographic structures of highly symmetrical designed toroidal cTRPs display rotational averaging in the crystal lattice.
Figure 22B:
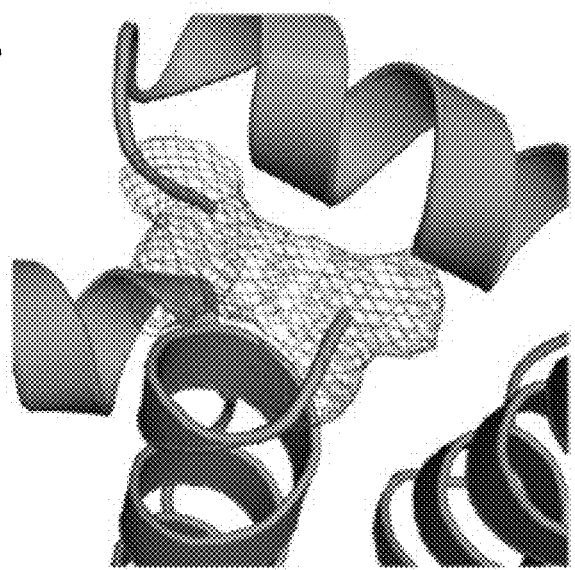
Figure 24A:
Figure 24B:
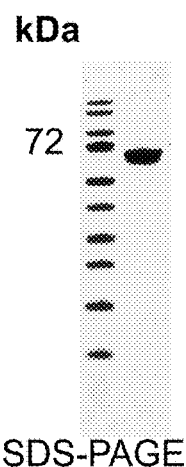
Figure 24C:
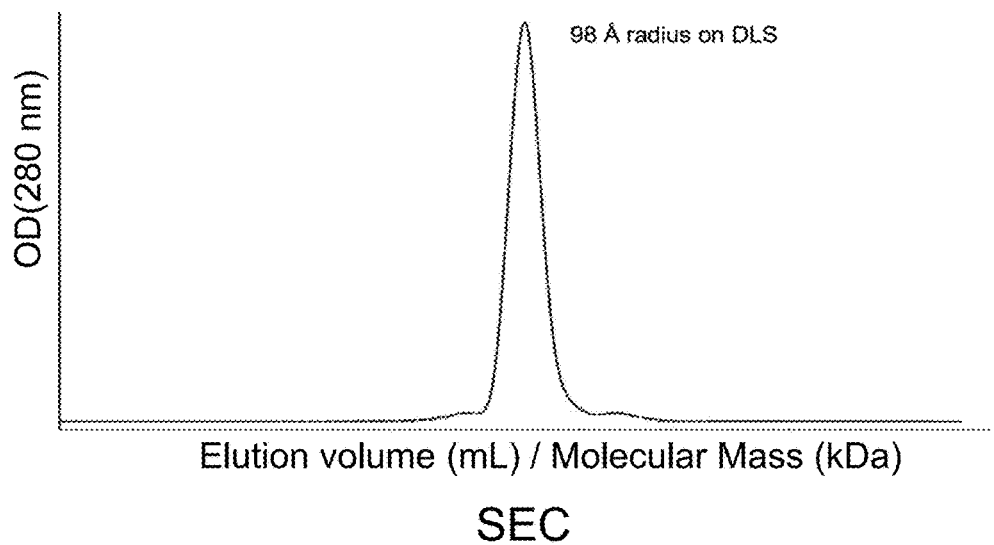

Crystal structures for the five monomeric repeat architectures were determined (FIG. 19), as well as a SAXS (small angle X-ray scattering) analysis of dTor_24×33L (FIG. 8). Close examination of the electron density for the five crystal structures, during and after refinement, indicated that most of these highly symmetrical designed cTRPs display significant rotational averaging within the crystal lattice, such that the positions corresponding to the loops that connect each repeated module are occupied by a mixture of continuous peptide and protein-termini (FIG. 22). This lattice behavior was observed for most of the structures, but only appeared to significantly affect the refinement R-factors for a final multimeric construct (described below) including multiple copies of the first 3 repeats of dTor_9×31L. In all cases, however, the positions and conformations of secondary structure and individual side chains, which are largely invariant from one repeat to the next, were clear and unambiguous in the respective density maps (FIG. 21). Kajander et al., have reported similar crystal averaging with associated disorder at protein termini in a set of structures for designed consensus TPR repeat proteins, albeit with translational averaging along a fiber axis rather than the rotational averaging observed here. Acta Crystallogr D Biol Crystallogr 63, 800-811, (2007).

Comparison of the design models to the experimental crystal structures shows that four of the initially characterized designs formed left-handed α-helical toroids with the intended geometries (FIG. 20). The structural deviation between design model and experimental structure increases with increasing repeat number: from 0.6 Å for the 3-repeat design, to 0.9 Å for the 6-repeat design, to 1.1 Å for the 9-repeat and 12-repeat designs. Inspection of the superpositions in for example, FIG. 20 suggest that the design models are slightly more compact than the experimental structures, a discrepancy which becomes more noticeable as the number of repeats increases. This trend may reflect a tendency of the current design procedure to over-pack side chains during the sequence optimization step (perhaps due to under-weighting of repulsive electrostatic or van der Waals interactions). Nevertheless, the crystal structures indicate that it is possible to control the geometry of the central pore by varying the number of repeats, without the need to re-optimize the sequence of individual repeats.

Figure 9A:
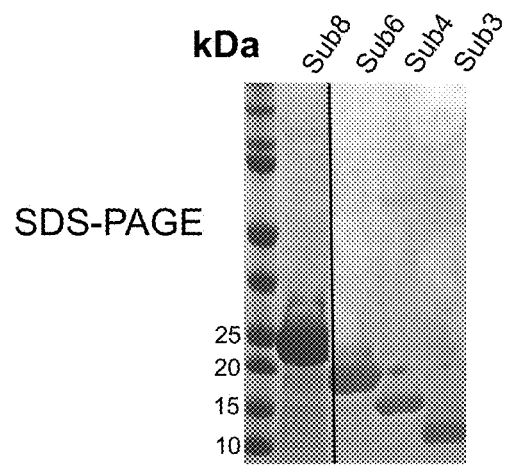
Figure 9B:
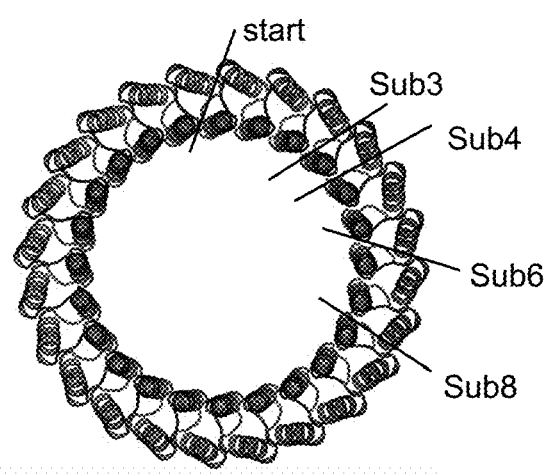
Figures 9C, 9D:
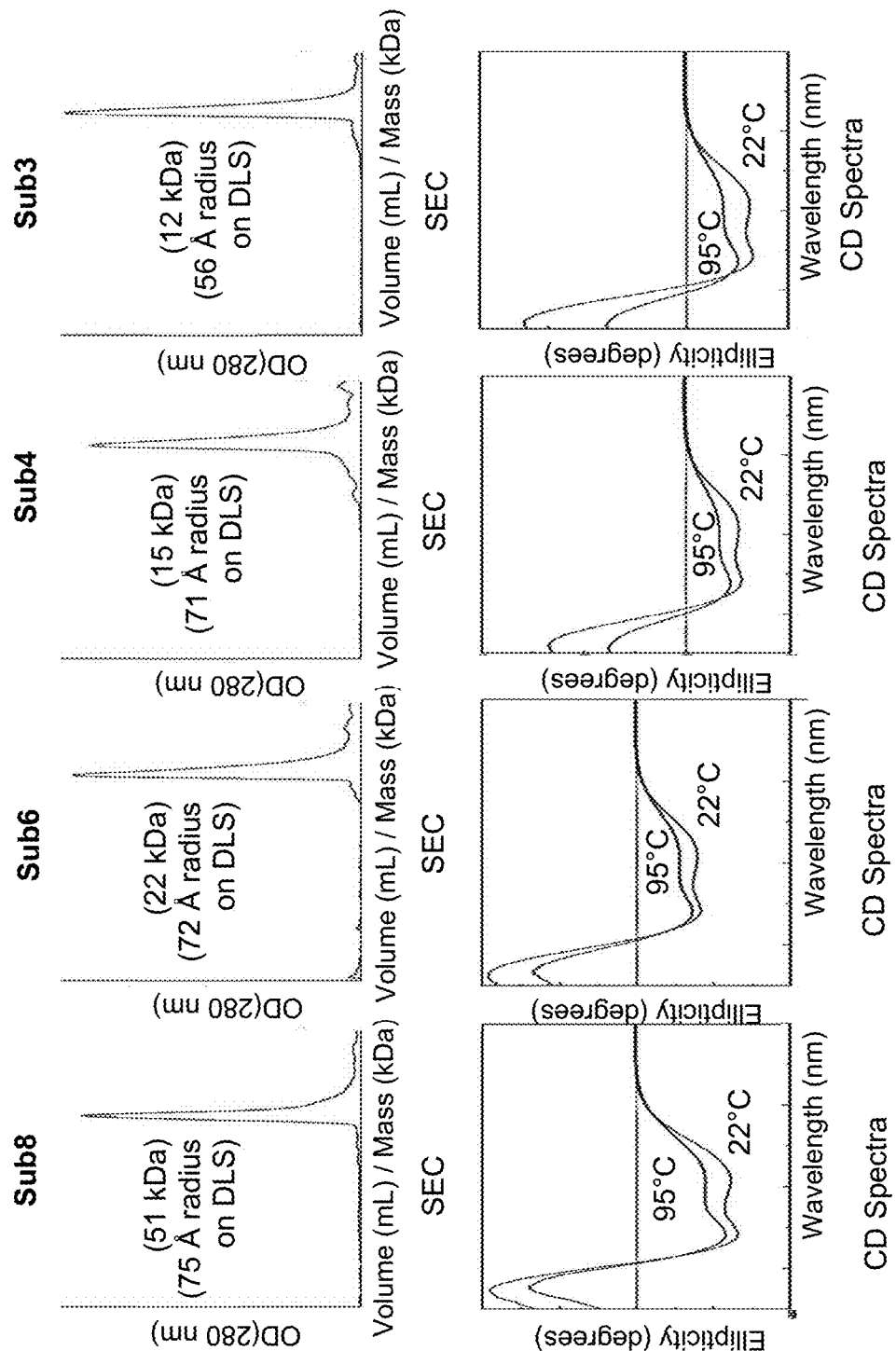

The feasibility of splitting monomeric designs into fragments that can assemble symmetrically to reform complete toroids including multiple copies of identical subunits was explored (see, for example, FIG. 9). Two of the crystallized toroid designs—dTor_3×33L and dTor_6×35L—form stable dimers in solution. To investigate the nature of these dimeric interfaces, the crystal packing interactions in disclosed solved structures was examined. For the 3×33L design, the same monomer-monomer packing interaction is seen in both the crystal forms ($P2_12_12_1$ and $P4_32_12$), which led to the belief that this mode of association provides a plausible model for the manner in which the monomers associate in solution. In the single crystal structure of the 6×35L design, two monomers stacking in a head-to-head manner and stabilized by electrostatic interactions appear to provide the most likely model of the solution dimer.

An alternative in either case would be for the monomers to associate as head-to-tail dimers to form a single larger ring, (akin to the tetrameric ring formed by the 3-repeat dTor_9×31L_sub3 construct), with concomitant breakage of the intra-monomer interactions between terminal repeats that are observed in the crystalline state. Given the stable, well-packed nature of the 3× and 6× designs, it was hypothesized that such an association mode would be disfavored due to loss of favorable packing interactions and energetic strain caused by the altered curvature of a larger ring. To evaluate this hypothesis in the case of the 3-repeat construct 3×33L_2-2, multiple independent symmetric folding simulations were performed in order to model the structure of a 6-repeat ring composed of two copies of the 3-repeat construct; for comparison, the same simulation protocol to model the 3-repeat construct forming a 3-repeat ring as designed was used. Analysis of packing quality and per-residue energies in these simulations suggests that the 6-repeat dimerization mode is indeed significantly less favorable than the 3.

Figure 14A:
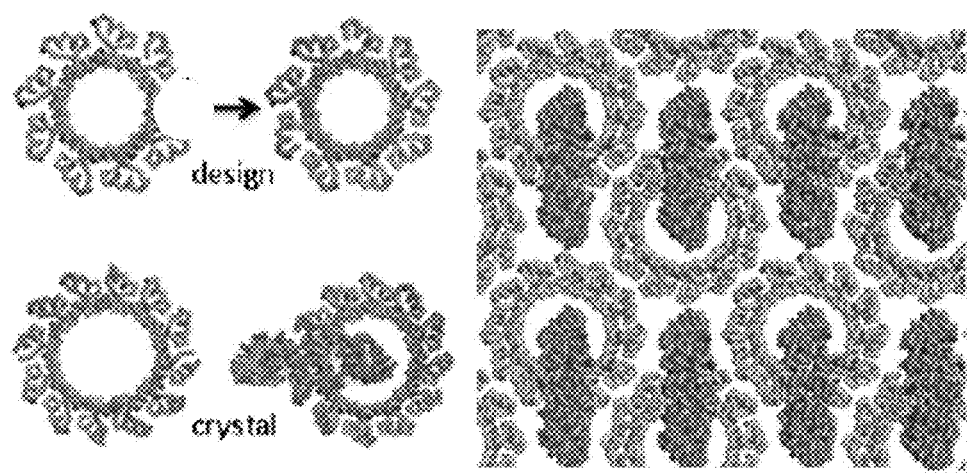
FIGS. 14A-14C. Various forms of cTRP interactions and packing as observed in crystal lattices solved by X-ray crystallography. Crystal packing geometries of designed toroid, dTor_9×31L_sub3 (FIG. 14A). Rather than forming the expected trimeric toroid ("design" arrow), the 3-repeat sub-fragment of dTor_9×31L associated in the crystal as two linked tetrameric rings ("crystal") which pack into the layers visualized on the right (the full crystal is then formed from stacks of these layers). Continuous channels are assembled from stacked toroids in the crystals of the monomeric dTor_9×31L and dTor_12×31L designs (FIG. 14B) and (FIG. 14C) respectively. These structures show the potential beneficial uses as filtering and/or fluid conducting materials.

The structurally characterized 9×31L design was selected to split into a small 3-repeat subfragment. The 3-repeat subfragments were expected to form a trimeric assembly. This 3-repeat fragment was expressed, purified, and formed diffraction-quality crystals. Upon determination of the experimental structure, it was discovered that the design fragment formed an unexpected crystal packing arrangement composed of linked tetrameric rings (i.e., including a total of 12 repeats per ring, FIG. 14A). Indeed, it was this unanticipated finding that led to the synthesis of the monomeric 12×31L design whose characterization demonstrated that the designed 31 residue repeat sequence is indeed compatible with both 9- and 12-repeat monomeric toroidal geometries (and presumably 10- and 11-repeat geometries as well). The crystal structure of the 3-repeat fragment suggests that the 12× geometry may be preferred, and indeed this would be consistent with the tendency of the disclosed design procedure to over-pack the design models.

The current database of solved protein structures was analyzed to assess the uniqueness of the disclosed designed cTRPs in terms of global similarity and bundle handedness.

DALI searches: Representative models from each of the design families were submitted to the DALI server. Holm & Rosenstrom, Nucleic Acids Research 38, W545-W549, (2010). For the left-handed bundles, top Z-scores ranged from 3 to 5 with relatively short alignments that did not cover substantial portions of the design or matched PDB structure. For the right-handed design dTor_6×33R, on the other hand, the top Z-scores exceeded 11.0 and top alignments were longer, although sequence identities were low (5-20%) and RMSD's were high (above 6 Å). Top-scoring matches were found primarily to right-handed helical bundles assembled from hairpins (as is dTor_6×33R), however toroidal (closed circular) structures were not found (by visual inspection of the top few matches).

To minimize the likelihood of missing a similar structure, multiple databases were consulted. Representatives from the SCOPe (Fox, et al., Nucleic Acids Res 42, D304-309, (2014)) a/a toroid fold (a.102), the CATH a/a barrel architecture, the ECOD (Cheng, et al., PLoS Comput Biot 10, e1003926, (2014)) a/a toroid topology, and the RepeatsDB (Di Domenico, et al., Nucleic Acids Res 42, D352-357, (2014)) α-barrel classification were visually inspected.

The SCOPe database contains two folds already classified by handedness: a.118, the α-α superhelix fold, described as having a right-handed superhelix, and a.298, the left-handed α-α superhelix fold. The a.118 fold class is composed 24 superfamilies, which include canonical α-helical repeats such as the Armadillo and TPR families. By contrast, the a.298 fold includes only the TAL effector-like family, composed of DNA-binding domains from plant-pathogenic bacteria (and designed variants thereof). These are not circular structures.

In the ECOD database, α superhelices are collected together into a single top-level grouping. Representative structures and domain boundaries (410 total) for this grouping were downloaded and analyzed using Rosetta to determine the handedness of the bundle. Visual inspection of all domains identified as potentially left-handed revealed that the only proteins containing multiple complete turns of the solenoid belonged to the mitochondrial mTERF and TAL effector families. Again, these are not circular structures. In ECOD these two homology-level families are grouped together at the "possible homology" ("X") level, and indeed there are similarities in their overall structures and modes of DNA binding. Finally, representatives of the α-solenoid (III.3) grouping were analyzed in RepeatsDB (48 domains) and no left-handed bundles were found.

It is worth mentioning that a few α-helical barrel structures (for example, PDB ID 1okc) were encountered for which it was difficult to assign a handedness because the α-helices composing the barrel follow an up-down path rather than twisting around a bundle axis (in other words, the helices do not form a true solenoid/super-helical structure, a fact which is supported by the SCOPe and ECOD classifications of 1okc).

Successful design of several left-handed cTRPs demonstrates that the apparent absence of this fold from the current database of solved structures is not due to constraints imposed by the helical solenoid architecture or the toroidal geometry.

In particular embodiments, the left-handedness of particular cTRPs is due in part to the use of inter-helical turns whose geometry naturally imparts a handedness to the resulting helical bundle. The 3-residue 'GBB' (αL-β-β) turn type used in particular embodiments prefers a left-handed dihedral twist between the connected helices, while the 'GB' turn found in dTor_6×33R correlates with right-handed geometry (FIG. 15). Both these turn types are also compatible with canonical helix capping interactions, which may explain their selection by the design procedure (helix capping guarantees satisfaction of backbone polar groups and also strengthens sequence-encoding of local structure).

Based on the foregoing, and as stated, in particular embodiments linkers between α helix residues can utilize a GBB format. In particular embodiments, the G residue is glycine. In particular embodiments, the G residue is not isoleucine or valine. In particular embodiments, the B residues are selected from serine, threonine, asparagine, or glutamine. FIG. 23 provides examples of GBB linkers (underlined) including GKS; GIT; GTT; GYS; GDK; GDE; NDK; GDR; GDL; and GIS. As will be understood by one of ordinary skill in the art, particular residues that fall within a G or B classification can depend on the particular protein at issue. Therefore, while representative (and common) selection options within these groups are provided, such examples are not exclusive to use of other potential residues. Without being bound by theory, and in particular embodiments, GBB linkers are utilized because they facilitate formation of left-handed proteins. See FIG. 15. Also referring to FIG. 23, it is important to note that while most of SEQ ID NOs. 51-72 are depicted starting with a GBB linker, due to the circular architecture of the disclosed repeat proteins, the repeat proteins can "begin" or "end" with any residue at the N- or C-terminus.

In particular embodiments, repetitive α-helical structures joined by linkers can be formed from sequences selected from:

GISVEELLKLAKAAYYSGTTVEEAYKLALKL; (SEQ ID NO: 73)

GISVEELLKLAEAAYYSGTTVEEAYKLALKL; (SEQ ID NO: 74)

GKSPTEALLKLIAEAKGITETEAKEEAEKALKE; (SEQ ID NO: 75)

GKSPTEALLKLIAEAKGITSTEAKEEAIKALKE; (SEQ ID NO: 76)

GKSPTEALLKLIAEAKGITELEAKVLAEKALKE; (SEQ ID NO: 77)

GKSPTEALLKLIAEAKGITETEAKLEAEKALKE; (SEQ ID NO: 78)

GKSPTEVLLELIAEASGTTKEEVKEKFLKELSK; (SEQ ID NO: 79)

GKSPTEVLLELIAEASGTTKEEVKRKFLKELSK; (SEQ ID NO: 80)

GKSPTEVLLELIAEASGTTKAEVKREFLWELSL; (SEQ ID NO: 81)

GKSPTEVLLELIAEASGTTKEEVKEKFLAELEK; (SEQ ID NO: 82)

GKSPTEVLLELIAEASGTTREEVKEKFLKELRK; (SEQ ID NO: 83)

GKSPTEVLLELIAEASGTTKEEVKEKFLKELSF; (SEQ ID NO: 84)

GKSPTEVLLELIAEASGTTKEEVKKKFWKELSL; (SEQ ID NO: 85)

GKSPTEVLLELIAEASGTTKREVKRWFLFELRK; (SEQ ID NO: 86)

GKSPTEVLLELIAEASGTTKAEVKLKFLFELSF; (SEQ ID NO: 87)

GKSPTEVLLELIAEASGTTKEEVKEKFLKELFK; (SEQ ID NO: 88)

GYSTTEALLILIAEASGTTVEQQKQRFKELVKK; (SEQ ID NO: 89)

GDKTAIAQILAIKASAKGDETELERALRYAKKV; (SEQ ID NO: 90)

GDKTAIAQILAIKASAKGDETELERALRYAVKV; (SEQ ID NO: 91)

GDKTAIAQILAIKASAKGDETELEQALRYAKFV; (SEQ ID NO: 92)

GDKTAIAQILAIKASAKGDELELTRALAYAKKV; (SEQ ID NO: 93)

GDKTAIAQILAIKASAKGDETELERALRYAKLV; (SEQ ID NO: 94)

GDKTAIAQILAIKASAKGDETELERALRYAKYV; (SEQ ID NO: 95)

GDKTAIAQILAIKASAKGDEPELEYALAYAKKV; (SEQ ID NO: 96)

GDKTAIAQILAIKASAKGDETELERALIFAEAV; (SEQ ID NO: 97)

NDKTAIAQILAIKASAKGDETELDRALVVYAKKV; (SEQ ID NO: 98)

GDKTAIAQILAIKASAKGDETELERALLYAKKV; (SEQ ID NO: 99)

GDKTAIAQILAIKASAKGDETELERALAYARLV; (SEQ ID NO: 100)

GDKTAIAQILAIKASAKGDETELERALRYAEKV; (SEQ ID NO: 101)

GDKTAIAQILAIKASAKGDEQELEAALIYAKKV; (SEQ ID NO: 102)

GDKTAIAQILAIKASAKGDETELERALVVYAKKV; (SEQ ID NO: 103)

GDRSAIATAYIALAEYLGDKEALLKAIEIAIKL; (SEQ ID NO: 104)

GDRSAIAEAYIALARYLGDKEALLKAIEIAIKL; (SEQ ID NO: 105)

GDKSALAQILAIYASAYGDTTLFLRALKLAKEV; (SEQ ID NO: 106)

GDLELYIRVLAIVAEAEGDKTKLELALKLALKK; (SEQ ID NO: 107)

GDLKLYIEVLAIVAEAEGDKTKLELALKLALKK; (SEQ ID NO: 108)

GDLELYIRVLAIVAKAEGDKTKLELALKLALKK; (SEQ ID NO: 109)

GDLKLYIEVLAIVAKAEGDKTKLELALKLALKK; (SEQ ID NO: 110)

GVSLEQALKILKVAAELGTTVEEAVKRALKLKTKL; (SEQ ID NO: 111)

GVSLEQALKILEVAAELGTTVEEAVKRALKLKTKL; (SEQ ID NO: 112)

GVSLEQALKILEVAAKLGTTVEEAVKRALKLKTKL; (SEQ ID NO: 113)

GVSLEQALKILEVAAELGTTVEEAVKRAMKLKTKL; (SEQ ID NO: 114)
and

LVSLEQALKILKVAAELGTTVEEAVKRALKLKTKL. (SEQ ID NO: 172)

Additional examples include SEQ ID NO: 130-134; 141-144; and 148.

SEQ ID NOs: 51-70; 117-123; 135-138; and 145 provide exemplary repetitively patterned amino acid sequences that create cTRPs. In particular embodiments, adjacent structural repeats can include sequences that are identical or that have at least 99%, at least 98%, at least 97%, at least 96%, at least 95%, at least 94%, at least 93%, at least 92%, at least 91%, at least 90% or at least 85% sequence identity to the adjacent structural repeat. Methods to determine sequence identity are described below.

As will be understood by one of ordinary skill in the art, variants of the cTRP sequences, that do not alter the circular, handed and repetitive structural nature of the proteins can also be used. Indeed, variants of all protein sequences disclosed herein can be used, so long as the variation does not render the protein unfit for its intended purpose.

"Variants" include protein sequences having one or more amino acid additions, deletions, stop positions, or substitutions, as compared to a protein sequence disclosed elsewhere herein.

An amino acid substitution can be a conservative or a non-conservative substitution. Variants of protein sequence disclosed herein can include those having one or more conservative amino acid substitutions. A "conservative substitution" or "conservative amino acid substitution" involves a substitution found in one of the following conservative substitutions groups: Group 1: Alanine (Ala; A), Glycine (Gly; G), Serine (Ser; S), Threonine (Thr; T); Group 2: Aspartic acid (Asp; D), Glutamic acid (Glu; E); Group 3: Asparagine (Asn; N), Glutamine (Gln; Q); Group 4: Arginine (Arg; R), Lysine (Lys; K), Histidine (His; H); Group 5: Isoleucine (Ile; I), Leucine (Leu; L), Methionine (Met; M), Valine (Val; V); and Group 6: Phenylalanine (Phe; F), Tyrosine (Tyr; Y), Tryptophan (Trp; W).

Additionally, amino acids can be grouped into conservative substitution groups by similar function, chemical structure, or composition (e.g., acidic, basic, aliphatic, aromatic, or sulfur-containing). For example, an aliphatic grouping may include, for purposes of substitution, G, A, V, L, and I. Other groups including amino acids that are considered conservative substitutions for one another include: sulfur-containing: M and C; acidic: D, E, N, and Q; small aliphatic, nonpolar or slightly polar residues: A, S, T, P, and G; polar, negatively charged residues and their amides: D, N, E, and Q; polar, positively charged residues: H, R, and K; large aliphatic, nonpolar residues: M, L, I, V, and C; and large aromatic residues: F, Y, and W.

Non-conservative substitutions include those that significantly affect: the structure of the peptide backbone in the area of the alteration (e.g., the α-helical or beta-sheet structure); the charge or hydrophobicity of the molecule at the target site; or the bulk of the side chain. Non-conservative substitutions which in general are expected to produce the greatest changes in the protein's properties are those in which (i) a hydrophilic residue (e.g. S or T) can be substituted for (or by) a hydrophobic residue (e.g. L, I, F, V, or A); (ii) a C or P can be substituted for (or by) any other residue; (iii) a residue having an electropositive side chain (e.g. K, R, or H) can be substituted for (or by) an electronegative residue (e.g. Q or D); or (iv) a residue having a bulky side chain (e.g. F), can be substituted for (or by) one not having a bulky side chain, (e.g. G). Additional information is found in Creighton (1984) Proteins, W.H. Freeman and Company.

Variants of protein sequences disclosed herein also include proteins with at least 70% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to a protein sequence disclosed herein.

"Percent (%) amino acid sequence identity" with respect to the sequences identified herein is defined as the percentage of amino acid residues in a candidate sequence that are identical with the amino acid residues in the reference sequence after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % amino acid sequence identity values generated using the WU-BLAST-2 computer program (Altschul et al., Methods in Enzymology, 266:460-480 (1996)) uses several search parameters, most of which are set to the default values. Those that are not set to default values (i.e., the adjustable parameters) are set with the following values: overlap span=1, overlap fraction=0.125, word threshold (T)=11 and scoring matrix BLOSUM62.

In addition to being circular, handed, and structurally repetitive, the cTRPs disclosed herein exhibit self-folding, high thermostability, and high solubility. Self-folding means that the cTRPs fold without any need for inclusion of additional folding domains or subunits (e.g., additional protein domains physically appended to the cTRP construct, or independently added protein folding chaperones such as GroEL/GroES or redox-dependent folding cofactors such as thioredoxin). High thermostability means that the proteins retain their overall secondary structure (including alpha-helices) and tertiary structures (defined by their size and shape) at temperatures as high as 95° C. High solubility means that the proteins can be concentrated to levels of 1 mg/mL or higher at physiological pH and salt concentrations without formation of soluble protein aggregates or protein precipitate.

Figure 14B:
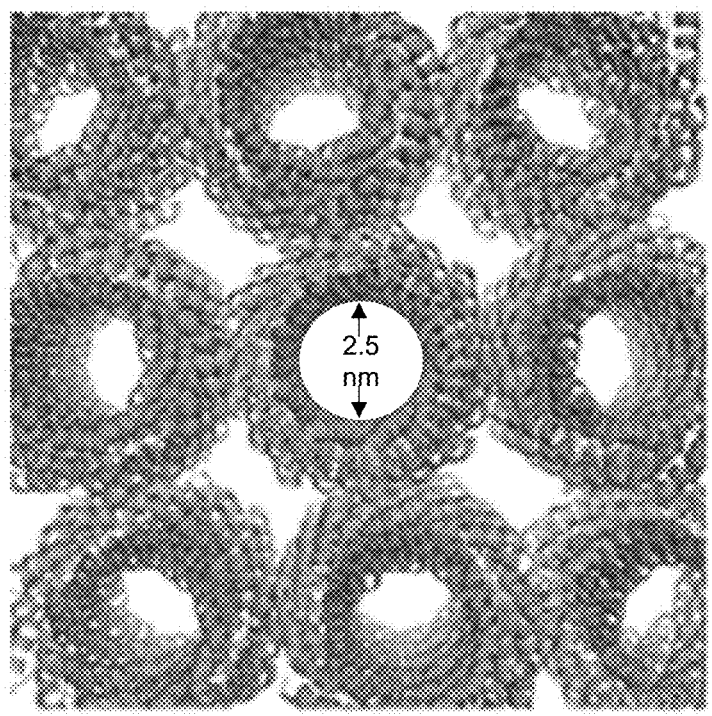
Figure 14C:
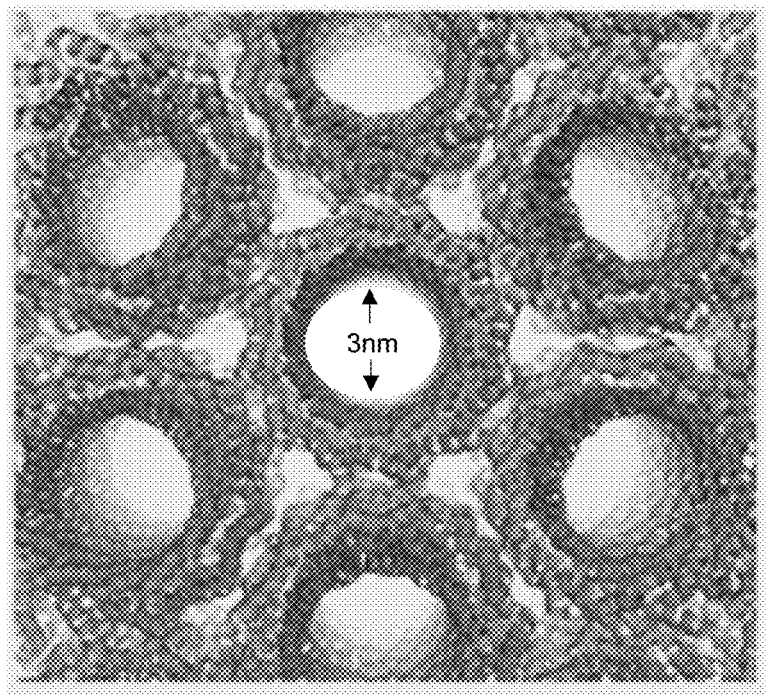
Figure 16C:
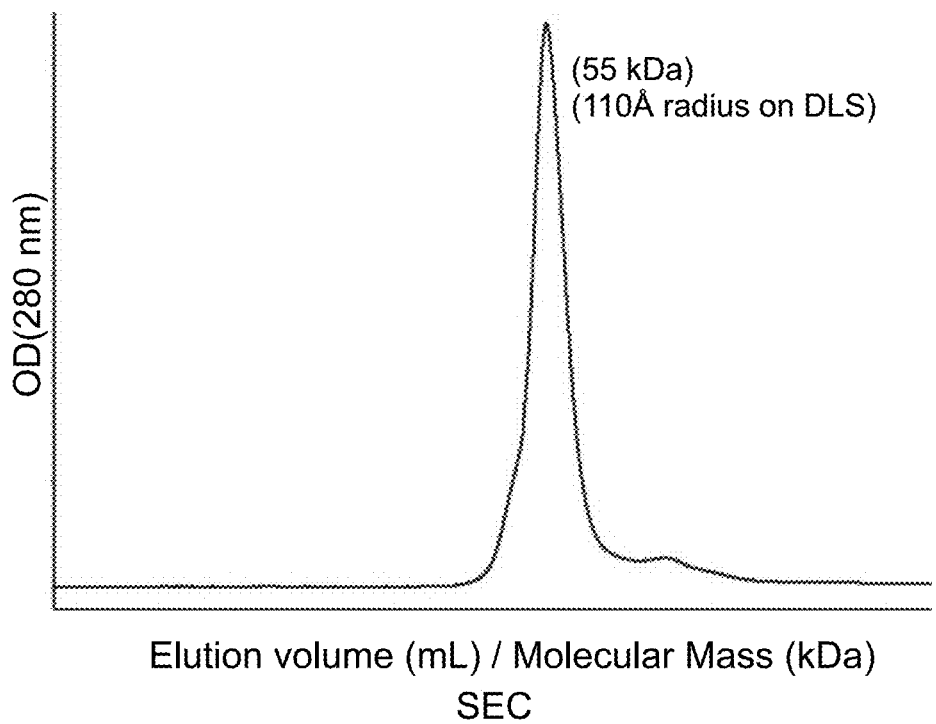
Figure 16D:
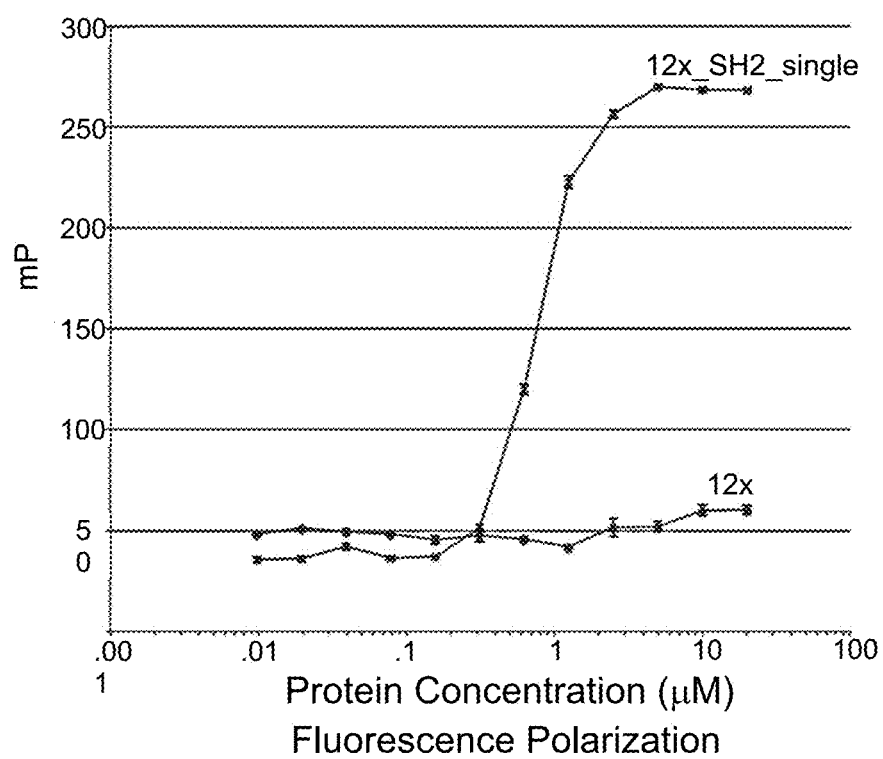
Figure 17C:
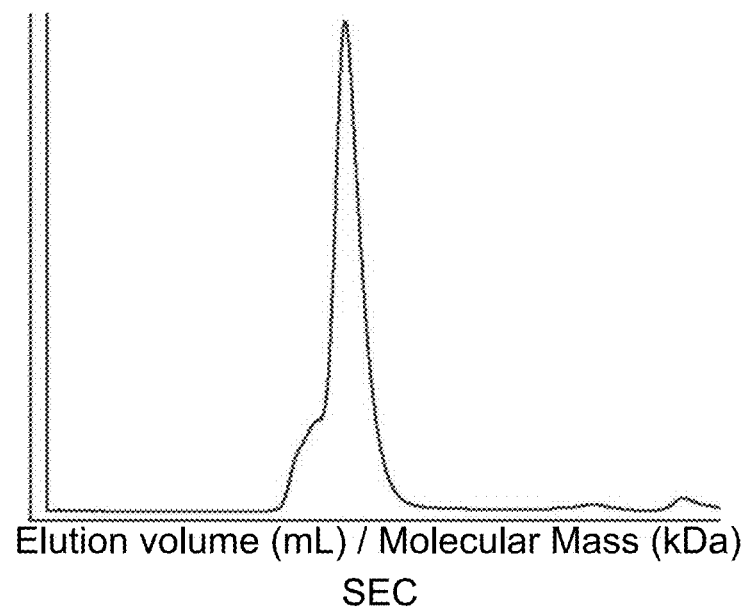
Figure 17D:
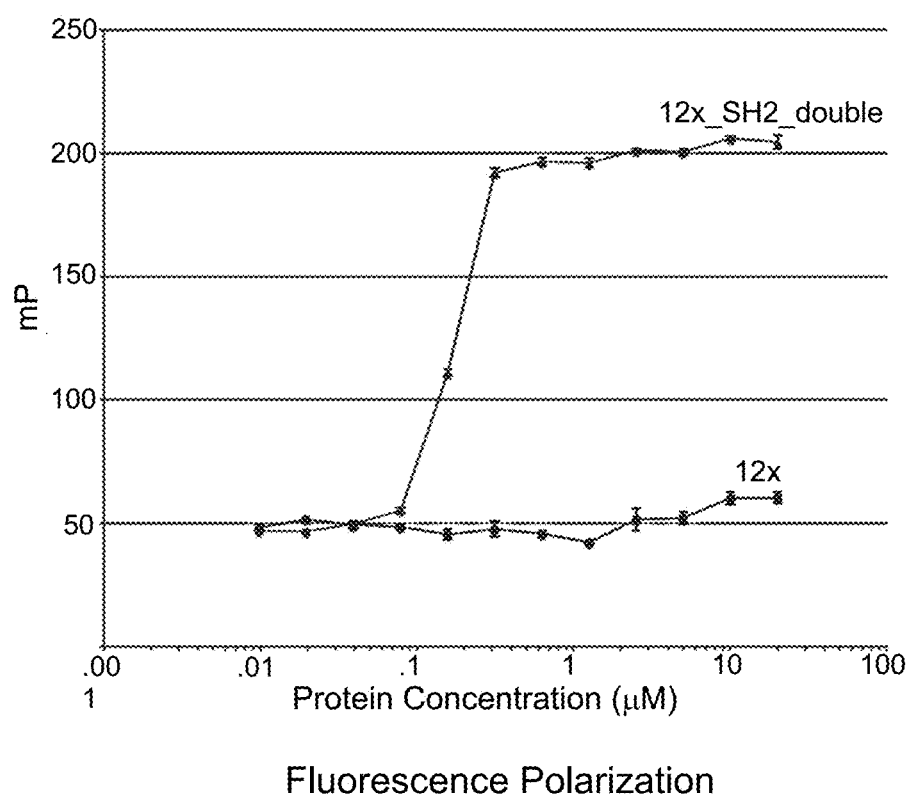
Figure 18A:
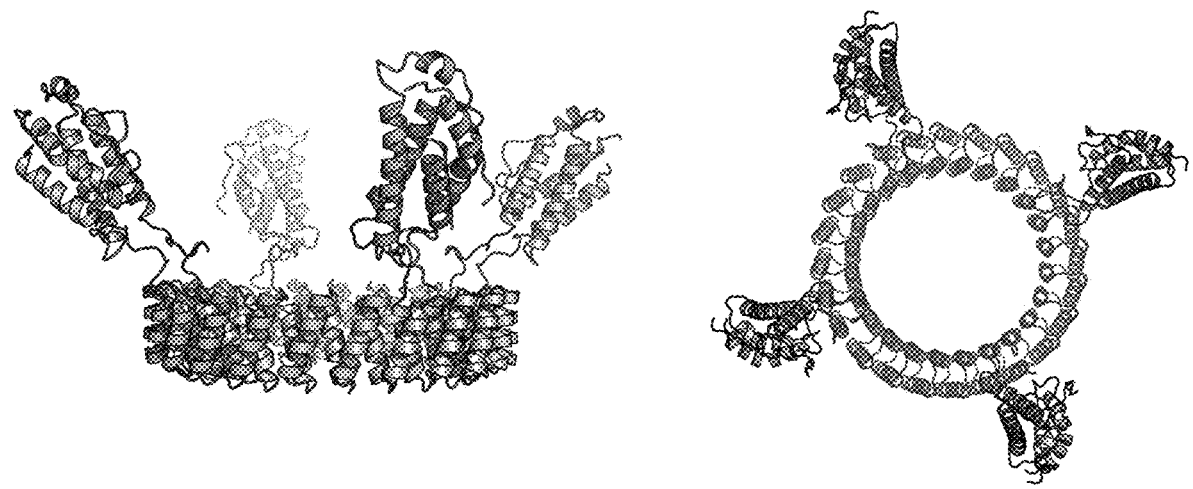
Figure 18B:
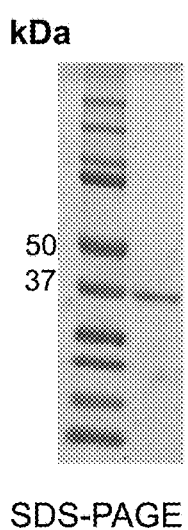
Figure 18C:
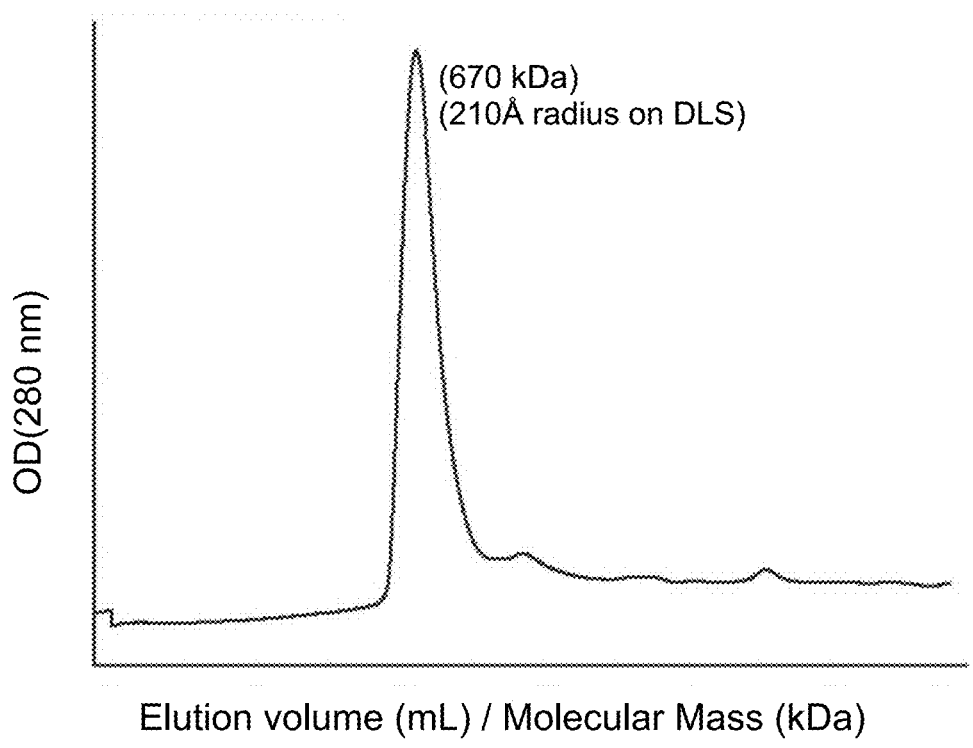
Figure 18D:
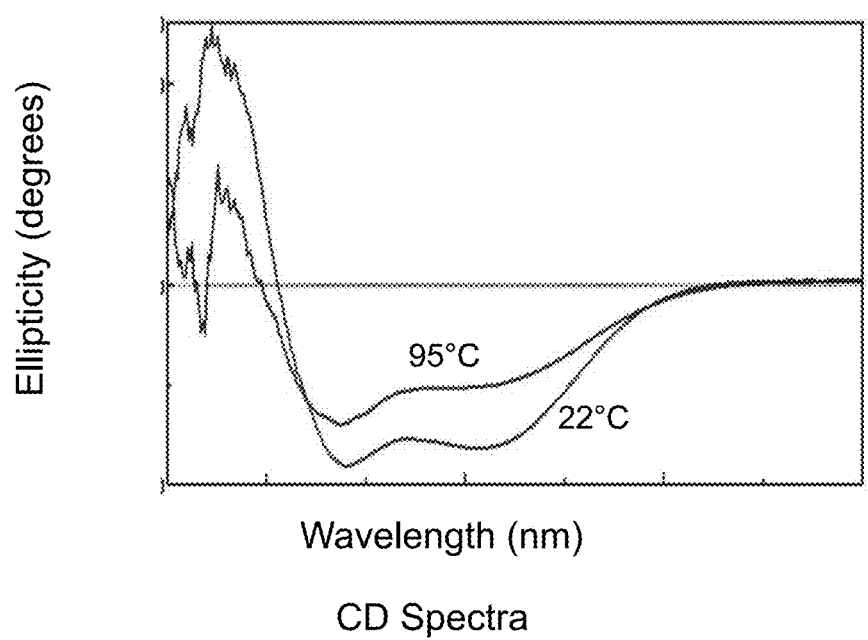
Figure 18E:
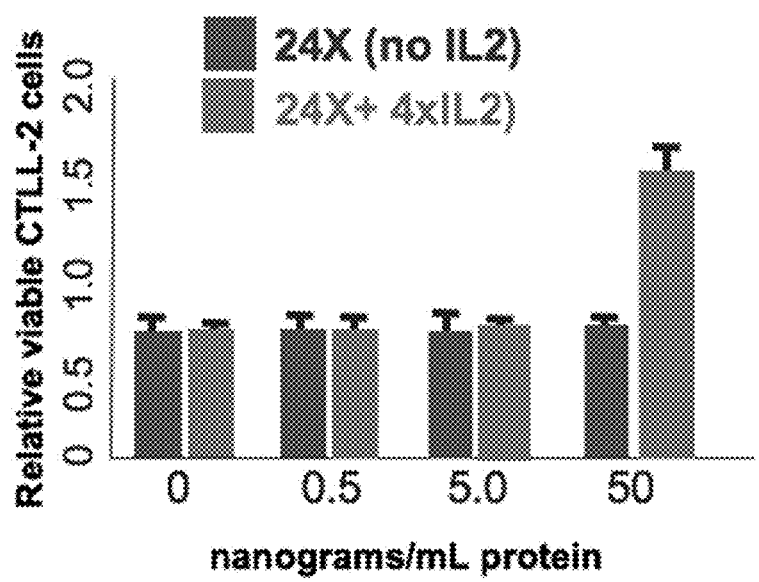
Figure 20A:
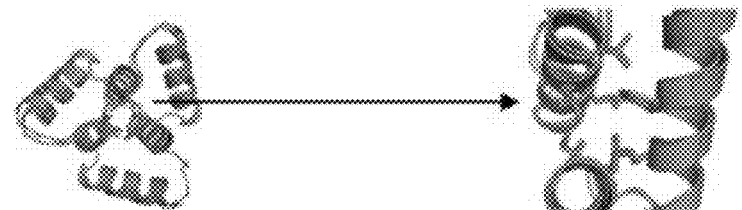
FIGS. 20A-20D. Superposition of designed cTRP models (dark grey) and their refined experimentally determined crystallographic structures (light grey). The left panels show the overall superposition of the entire protein backbone, with the side chains that line the innermost pore shown for both models. The right panels show the same superpositions, enlarged to show the packing of side chains and helices between consecutive repeat modules. The overall calculated α-carbon RMSD for all superimposed atoms across the entire structure, between each design and corresponding refined crystal structure, ranges from 0.6 Å for design dTor_3×33L (FIG. 20A), to 0.9 Å for design dTor_6×35L (FIG. 20B), to 1.1 Å for designs dTor_9×31L and dTor_12×31L (FIGS. 20C and D, respectively). The corresponding average RMSD values between design and refined crystal structures calculated across individual repeats is lower for each pair, ranging from 0.5 Å for dTor_3×33L to 0.8 Å for dTor_12×31L.
Figure 20B:
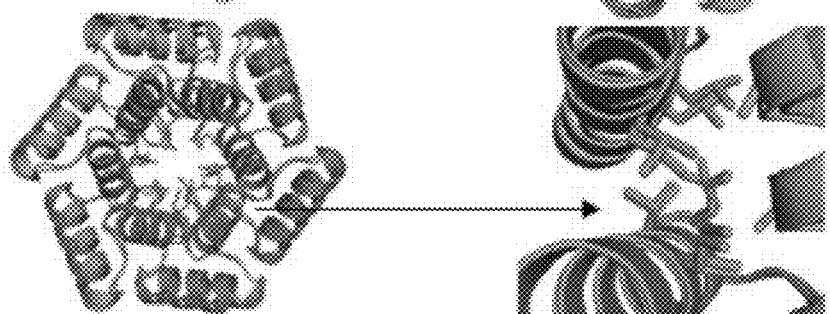
Figure 20C:
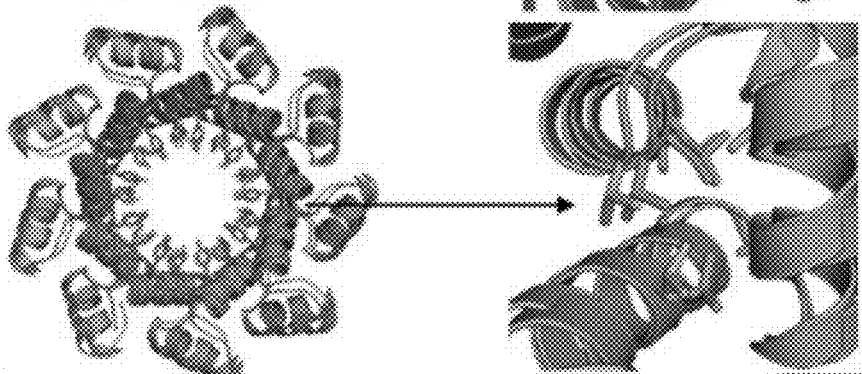
Figure 20D:
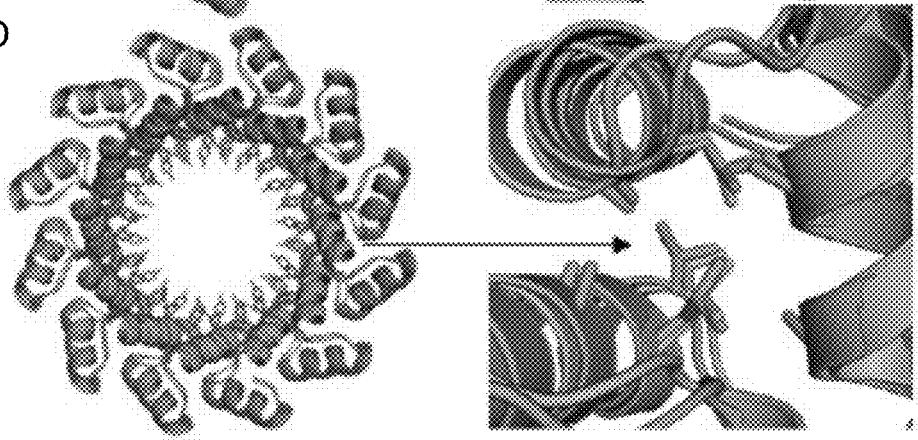
Figure 21A:
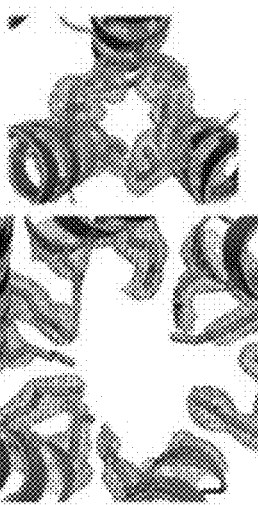
FIGS. 21A-21D. Unbiased 2Fo-Fc omit maps contoured around the side chains including the central pore regions for each crystallized toroid. The constructs shown are in the following order: (dTor_3×33L (FIG. 21A); dTor_6×35L (FIG. 21B), dTor_9×31L (FIG. 21C); and dTor_12×31L (FIG. 21D).
Figure 21B:
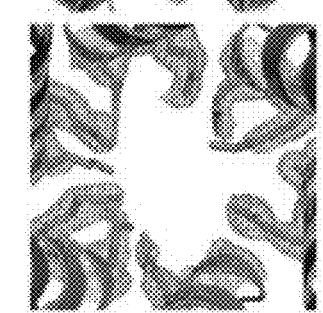
Figure 21C:
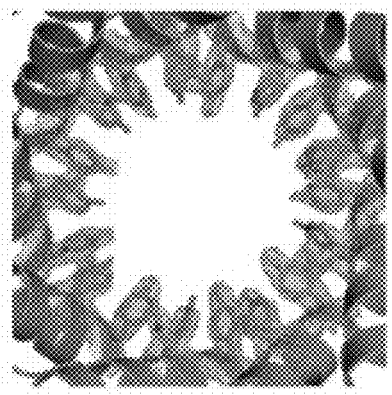
Figure 21D:
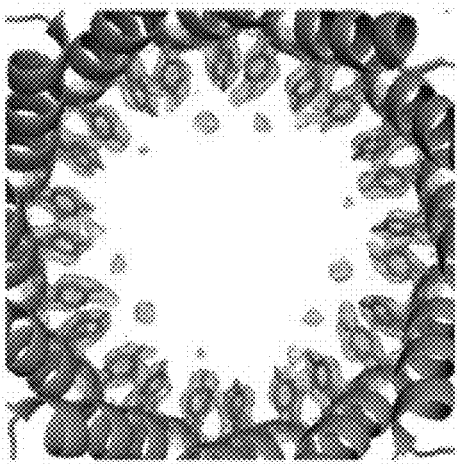

Examination of the crystalline arrangements formed by the cTRPs shows the creation of specific 1- and 2-dimensional assemblies: both the monomeric 9×31L and 12×31L crystals have channels extending continuously through the crystal formed from the pores in vertical stacks of proteins (FIGS. 14B and 14C), with 2-dimensional layers of toroids running perpendicular to these stacks. Interface design can be applied to stabilize the crystal contacts seen in the existing structures thereby further stabilizing either the crystalline state or these 1- or 2-dimensional sub-assemblies (Grove, et al., J. R. Soc. Interface 10, (2013); Lanci, et al., Proc. Natl. Acad. Sci. USA 109, 7304-7309, (2012)). Designed cTRPs with larger pores that crystallize in a similar manner can form crystal structures with channels capable of hosting guest molecules by covalent linkage or noncovalent binding. Stabilization of the concatemeric structure (FIGS. 14A-14C) formed by the 3-repeat fragment either by cross-linking or interface design could represent a path toward a variety of novel protein-based materials. Abe & Ueno, Rsc Adv 5, 21366-21375, (2015).

The disclosed cTRPs have applications as scaffolds for binding and catalysis and as building blocks for higher-order assemblies. Amino acids lining the central pores can be mutated to introduce binding or catalytic functionalities and/or sites of chemical modification. The modular symmetry of monomeric toroids can be exploited to array interaction surfaces with prescribed geometries: a designed interface on the external face of the 12×31L design, for example, could be replicated with 2, 3, 4, or 6-fold symmetry by repeating the interfacial mutations throughout the full sequence. Thus monomeric toroids could replace multimeric assemblies as symmetry centers in the assembly of protein cages; by breaking the symmetry of the interaction surfaces it is possible to create more complex heterotypic assemblies with non-uniform placement of functional sites. For example, SEQ ID NOs: 71; 72; and 149-151 provide inserted functional domains and FIGS. 16A-16D, 17A-17D, 18A-18D and 24A-24C show successful expression and folding of these cTRPs incorporating functional domains. Thus, the cTRPs disclosed herein can be exploited as insertion sites for peptides or protein moieties. The largest of the engineered repeat proteins created to date accommodates up to 24 inserted elements of variable composition. This provides highly adaptable nanoparticles for the display and delivery of precisely arranged arrays of peptides or protein factors. Particular embodiments can further include up to 50, 60, 70, 80, 90, 100, 110, 120, or 130 repetitive α-helical structures and/or functional domains of variable composition. Particular embodiments can include 96 or 124 repetitive α-helical structures and/or functional domains of variable composition.

In particular embodiments cTRPs include one or more functional domain. Examples of functional domains that can be incorporated into cTRPs include peptide binding domains (such as SH2 and SH3 domains), phosphotyrosine binding domains, LIM domains, SAM domains, PDZ domains, FERM domains, Pleckstrin homology domains, VVVV domains, oligosaccharide binding (OB) domains, Immunoglobulin domains (IgG), single chain MHC proteins, tumor specific antigens (such as CD19 or ROR1), receptor ectodomains, isolated antigenic or adjuvant peptides, small molecule ligand binding domains (e.g., maltose binding protein) and enzyme domains (for example, trypsin). In particular embodiments the functional domains include SH2, Protein L, cytokines (e.g., IL-2; IL-17c, IL-3); Notch ligands (e.g., Delta or Jagged); immunogenic peptides (e.g., SEQ ID NO: 116); and/or peptide adjuvants (e.g., SEQ ID NO: 115).

In embodiments incorporating functional domains, linkers can be utilized between the scaffold cTRP sequence and the functional domain sequence. Linkers can be used that fuse domains together and result in stably expressed, functional proteins. Examples of linkers can be found in Chen et al., Adv Drug Deliv Rev. 2013 Oct. 15; 65(10): 1357-1369. Linkers can be flexible, rigid, or semi-rigid, depending on the desired functional domain presentation to a target. Commonly used flexible linkers include Gly-Ser linkers such as SEQ ID NO: 152, SEQ ID NO: 153 and SEQ ID NO: 160. Additional examples include: GGGGSGGGGS (SEQ ID NO: 161); GGGSGGGS (SEQ ID NO: 162); and GGSGGS (SEQ ID NO: 163).

In some situations, flexible linkers may be incapable of maintaining a distance or positioning of functional domains needed for a particular use. In these instances, rigid or semi-rigid linkers may be useful. Examples of rigid or semi-rigid linkers include proline-rich linkers. In particular embodiments, a proline-rich linker is a peptide sequence having more proline residues than would be expected based on chance alone. In particular embodiments, a proline-rich linker is one having at least 30%, at least 35%, at least 36%, at least 39%, at least 40%, at least 48%, at least 50%, or at least 51% proline residues. Particular examples of proline-rich linkers include fragments of proline-rich salivary proteins (PRPs).

The rigidity of protein linkers refers to the degree of flexibility of the protein backbone over the entire length of a short, single chain protein as measured by the average root-mean-square (RMS) ($RMS^{fluct}$) of all internal torsion angles ($\phi,\psi$) over the length of a given single chain protein linker.

$RMS^{fluct}$ of a torsion angle is the standard deviation of the torsion angle value about the time-averaged value in a CHARMm molecular dynamics simulation, wherein $RMS^{fluct}$ is calculated as follows:

$$RMS^{fluct} = \sqrt{\frac{1}{N_f} \sum_f (\theta^f - \theta^{ave})^2}$$

where f refers to the frame number, N is the total number of frames in the trajectory file, and of and $\theta^{ave}$ are the current value and the average value for the torsion angle, respectively.

"CHARMm" (Chemistry at HARvard Macromolecular Mechanics) refers to a computer simulation engine (see Brooks et al., (1983) J Comp Chem 4: 187-217; MacKerell, et al., (1998) J. Phys. Chem. B 102(18): 3586-3616; and "CHARMM: The Energy Function and Its Parameterization with an Overview of the Program", by MacKerell et al., in The Encyclopedia of Computational Chemistry, Volume 1, 271-277, by Paul von Raque Schleyer et al., editors (John Wiley & Sons: Chichester, United Kingdom (1998)); and Brooks, et al., (2009) J. Comp. Chem., 30:1545-1615 (2009).

In particular embodiments, the average $RMS^{fluct}$ can be calculated using the formula: (average $RMS^{fluct}$ phi ($\phi$)+ average $RMS^{fluct}$ psi ($\psi$))/2. The average RMS fluctuation of all internal backbone torsion angles over the length of the protein can be used to quantify the rigidity of the protein linker. The more rigid the protein is the smaller the average RMS fluctuation should be due to a more limited conformational space accessible to the protein.

In particular embodiments, a rigid protein linker refers to a linker having an average $RMS^{fluct}$ of 25 or less, 20 or less 15 or less when measured using CHARMm modeling over a production run of 200 picoseconds (ps). In particular embodiments, a semi-rigid protein linker refers to a linker having an average $RMS^{fluct}$ of 45-25 when measured using CHARMm modeling over a production run of 200 picoseconds (ps).

As indicated, there are many possible uses of the disclosed cTRPs for synthetic biology and bioengineering (Mak, et al., Science 335, 716-719, (2012); Deng, et al., Science 335, 720-723, (2012); Barkan, et al., PLoS Genet. 8, e1002910, doi:10.1371/journal.pgen.1002910 (2012); Reichen et al., J. Struct. Biol. 185, 147-162, (2014); Wierenga, FEBS Lett. 492, 193-198 (2001)). Exemplary applications for the cTRPs include the incorporation and display of multiple copies of protein or peptide ligands for use in cell-stimulating growth factors and in vaccine development. Without being bound by theory, it is hypothesized that the display complex arrangements of multiple peptide and/or protein moieties onto stable protein nanoparticles, with well-defined symmetry and distances separating those individual components, will facilitate the creation of growth factor reagents and vaccines with exceptional biological activity as a result of (i) formation of high avidity interactions at the cell surface, and (ii) the potential to induce clustering of receptor complexes when the nanoparticle encounters its extracellular targets in vivo.

Cell manufacturing (e.g., the expansion of hematopoietic stem cells (and especially from limiting starting pools of such cells such as infant cord blood)) involves the addition of mixtures of cytokines and growth factors in various combinations to cell cultures. The overall biological activities of commercial cytokine and growth factor preparations in cell culture are suboptimal, being limited by the hostile environment of the cell incubator and media (which results in rapid protein degradation) and low activity in the wide-open spaces and volumes of the incubator (which negates the close intercellular distances that govern cytokine action in a living body). Therefore, the consumption, cost and effectiveness of these reagents is a clear target for improvement by a next generation of improved cell culture reagents, such as the cTRPs described herein. When used for cell manufacturing, the extreme physical and thermal stability of the underlying cTRP protein scaffolds (which have been shown to remain intact at temperatures up to 95° C.) greatly increases the stability and lifetime of the molecules used during manufacturing.

In particular embodiments, a variable number of copies of a well-characterized peptide binding domain (SH2 and/or SH3 domains) can be displayed on the surface of cTRPs (e.g., dTor_12×31L). SH2 domains are protein domains that can bind particular peptides or proteins motifs that contain a phosphorylated tyrosine. SH3 domains are protein domains that can bind particular peptides or protein motifs that contain two or more prolines. In particular embodiments the SH2 domain displayed on the surface of cTRPs is derived from the human Nck2 adapter protein, and binds a peptide with the sequence EHIpYDEVAAD (SEQ ID NO: 159). See, for example, FIGS. 16A-16E and FIGS. 17A-17E.

In particular embodiments, a variable number of copies of a well-characterized small ligand binding protein (Protein L) can be displayed on the surface of cTRPs (e.g., dTor_12×31L). Protein L exhibits very well-studied binding affinity and specificity towards IgG, and also has been used extensively as a model system for protein folding and stability (Kobe & Kajava, Trends Biochem. Sci. 25, 509-515 (2000); Main, et al., Structure 11, 497-508 (2003)).

In particular embodiments a variable number of copies of IL-2 can be displayed on the surface of cTRPs disclosed herein. IL-2 is a cytokine that stimulates various cell types, including T cells. In particular embodiments cTRPs that display IL-2 functional domains can be useful for stimulating T cells. In particular embodiments display of multiple copies of IL-2 on the surface of cTRPs can enhance IL-2 activity.

In particular embodiments, a variable number of copies of the IL-17c cytokine can be displayed on cTRPs disclosed herein. IL-17c has recently been shown to act as a potent neural growth factor. Because signaling is believed to be driven by ligand binding-induced multimerization of cell-surface IL-17RA and IL-17RE receptors, it is hypothesized that the presence of multiple copies IL-17c on the surface of the cTRPs can enhance signaling activity of the ligand.

In particular embodiments, a variable number of copies of IL-3 can be displayed on the surface of cTRPs disclosed herein. IL-3 is a cytokine that stimulates cells of the myeloid lineage, such as monocytes and dendritic cells. An example of an IL-3 sequence is SEQ ID NO: 173. In particular embodiments, cTRPs that display IL-3 functional domains can be useful for stimulating cells of the myeloid lineage.

In particular embodiments, a variable number of copies of Notch ligands (e.g. Delta or Jagged), or fragments and combinations thereof, can be displayed on the surface of cTRPs. Notch is a transmembrane protein with an extracellular EGF domain and intracellular domains that are involved in signaling. Notch proteins can be involved in embryogenesis and cell fate decisions, such as hematopoietic progenitor cell differentiation. Notch ligands such as Delta and Jagged can interact with Notch to influence cell differentiation. An example of a human Delta (also known as Delta-like protein) is SEQ ID NO: 174. An example of a human Jagged protein is SEQ ID NO: 175. The extracellular domains of Delta and Jagged proteins can interact with the extracellular domain of Notch protein. In particular embodiments, the extracellular domains of Notch and/or Jagged can be displayed on the surface of cTRPs.

In particular embodiments a functional domain linked to a cTRP can be a single chain MHC (scMHC) harboring an immunogenic peptide. MHC molecules are heterodimers (alpha chain and beta chain) that are expressed on the surface of cells and present peptides/antigens to T cells. There are several classes of MHC molecules and the best studied are class I and class II. Class I MHC molecules are expressed by all nucleated cells, and present non-self peptides. Class II MHC molecules are expressed on antigen presenting cells, and can present both self and non-self peptides. Single chain, scMHC molecules can be recombinant MHC proteins wherein functional fragments of an MHC alpha chain and an MHC beta chain are expressed from the same polypeptide. In particular embodiments the MHC alpha and beta chains can be derived from class I MHC molecules. In particular embodiments, the MHC alpha chain domain can be SEQ ID NO: 165. In particular embodiments, the MHC beta chain domain can be SEQ ID NO: 166. In particular embodiments, the immunogenic peptide can be derived from human cytomegalovirus. In particular embodiments, the immunogenic cytomegalovirus peptide can be NLVPMVATV (SEQ ID NO: 167)

In particular embodiments, a variable number of immunogenic peptide vaccine candidates (e.g., derived from a mutated growth factor receptor that acts as a commonly observed cancer-associated neoantigen) on one surface, along with multiple copies of a peptide adjuvant (e.g., derived from the HMGB1 high mobility group box protein) on the other can be displayed on cTRPs disclosed herein. For example, LEEKKGNYWTDHC (SEQ ID NO: 116) is an immunogenic peptide derived from in-frame deletion of exons 2 to 7 in the EGFR gene that results in an oncogenic growth factor receptor while also creating a high-frequency neoantigen across a wide variety of tumor types. This peptide is already very well studied as a peptide vaccine for treatment of Glioblastoma multiforme under the trade name 'Rindopepimut' (Boersma & Pluckthun, Curr. Opin. Biotechnol. 22, 849-857, (2011); Ramisch, et al., Proc. Natl. Acad. Sci. USA 111, 17875-17880, (2014). The peptide adjuvant (termed 'HP91; sequence DPNAPKRPPSAFFLFCSE (SEQ ID NO: 115)), which is derived from the B box domain of HMGB1 and induces activation of human and murine dendritic cells) can also be displayed. As described in Grove, et al., (Curr. Opin. Struct. Biol. 18, 507-515, (2008)) one of the simplest tests of immunogenicity of a vaccine candidate/adjuvant combination is an ELISPOT assay to monitor the activation of dendritic cells in vitro, as a function of the addition of the vaccine candidate molecules.

In particular embodiments, cTRPs can be linked to a detectable label. Detectable labels can be detected following administration to a subject using imaging techniques. Examples of imaging techniques include magnetic resonance imaging (MRI), magnetic resonance tomography (MRT), positron emission tomography (PET), computer tomography (CT), single-photon emission computed tomography (SPECT) and optical imaging, such as x-ray.

Detectable labels can include any suitable label or detectable group detectable by, for example, optical, spectroscopic, photochemical, biochemical, immunochemical, electrical, optical or chemical means. Such detectable labels include radiolabels (e.g., $^{35}S$, $^{125}I$, $^{32}P$, $^{3}H$, $^{14}C$, $^{131}I$), radioacoustic labels, enzyme labels (e.g., horseradish peroxidase, hydrolases, alkaline phosphatase), chemiluminescence labels, fluorescence labels (e.g., rhodamine, phycoerythrin, fluorescein, fluorescent proteins, Texas red), fluorescent proteins (e.g. a green fluorescent protein or one of its many modified forms), gold beads, magnetic beads (e.g. Dynabeads™), and biotin (with labeled avidin or streptavidin).

Based on the foregoing, it is anticipated that cTRPs disclosed herein can be formulated into compositions for administration to a subject. Subjects can include humans, veterinary animals (dogs, cats, reptiles, birds, etc.) livestock (horses, cattle, goats, pigs, chickens, etc.) and research animals (monkeys, rats, mice, fish, etc.).

Compositions include at least one repeat protein and at least one pharmaceutically acceptable carrier. In particular embodiments, the compositions include repeat proteins of at least 0.1%-99% w/v of the composition or from 0.1% w/w-99% w/w of composition.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

Exemplary antioxidants include ascorbic acid, methionine, and vitamin E. Exemplary buffering agents include citrate buffers, succinate buffers, tartrate buffers, fumarate buffers, and/or gluconate buffers. An exemplary chelating agent is EDTA. Exemplary isotonic agents include polyhydric sugar alcohols including trihydric or higher sugar alcohols, such as glycerin, erythritol, arabitol, xylitol, sorbitol, or mannitol. Exemplary preservatives include phenol, benzyl alcohol, meta-cresol, methyl paraben, propyl paraben, and/or octadecyldimethylbenzyl ammonium chloride.

Stabilizers refer to a broad category of excipients which can range in function from a bulking agent to an additive which solubilizes the repeat proteins or helps to prevent denaturation or adherence to the container wall. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as powders, capsules and tablets, suitable excipients include binders (gum tragacanth, acacia, cornstarch, gelatin), fillers such as sugars, e.g. lactose, sucrose, mannitol and sorbitol. If desired, disintegrating agents can be added, such as corn starch, potato starch, alginic acid, cross-linked polyvinylpyrrolidone, agar, or alginic acid. If desired, solid dosage forms can be sugar-coated or enteric-coated using standard techniques. Flavoring agents can also be used.

Compositions can be formulated as an aerosol. In one embodiment, the aerosol is provided as part of an anhydrous, liquid or dry powder inhaler. Aerosol sprays from pressurized packs or nebulizers can also be used with a suitable propellant, e.g., dichlorodifluoromethane, trichlorofluoromethane, dichlorotetrafluoroethane, carbon dioxide or other suitable gas. Capsules and cartridges of gelatin for use in an inhaler or insufflator may also be formulated containing a powder mix of repeat proteins and a suitable powder base such as lactose or starch.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts.

Additionally, compositions can be formulated as sustained-release systems utilizing semipermeable matrices of solid polymers including at least one cTRP. Various sustained-release materials have been established and are well known by those of ordinary skill in the art.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

Exemplary Embodiments

1. A protein having the formula: $(a-b-x-y)_n$ wherein
   a and x represent GBB linker sequences selected from GKS; GIT; GTT; GYS; GDK; GDE; NDK; GDR; GDL; and GIS;
   b represents an amino acid sequence that forms an alpha (α) helix;
   y represents an amino acid sequence that forms a second α helix;
   n=3, 6, 9, 12, or 24;
   each (a-b-x-y) unit is structurally repetitive to an adjacent (a-b-x-y) unit;
   the protein is left-handed; and
   the N- and C-termini of the protein create a circular architecture.
2. A protein of embodiment 1 wherein b and y are identical sequences.
3. A protein of embodiment 1 or 2 wherein b and y are selected from SEQ ID NOs. 1-50; 124-129; 139; 140; 146; and/or 147.
4. A protein of any of embodiments 1-3 wherein a (a-b-x-y) unit is selected from SEQ ID NOs. 73-114; 130-134; 141-144; 172; and/or 148.
5. A protein of any of embodiments 1-4 including a sequence selected from SEQ ID NOs. 51-70; 117-123; 135-138 or 145.
6. A protein of any of embodiments 1-5 further including a functional domain (d) inserted in a (a-b-x-y) unit at a position selected from (d-a-b-x-y); (a-d-b-x-y); (a-b-d-x-y); (a-b-x-d-y); and (a-b-x-y-d).
7. A protein of any of embodiments 1-5 further including at least two functional domains inserted in at least two (a-b-x-y) units at positions selected from (d-a-b-x-y); (a-d-b-x-y); (a-b-d-x-y); (a-b-x-d-y); and/or (a-b-x-y-d).
8. A protein of embodiment 6 or 7 wherein the functional domain is selected from a cytokine, a Notch ligand, an immunogenic peptide, a peptide adjuvant, a single-chain class I MHC domain, or a small molecule ligand binding domain.
9. A protein of any of embodiments 6-8 wherein the functional domain is SH2, SH3, IL-2, IL-3, IL-17c, single-chain MHC, the extracellular domain of the Delta-1 Notch protein ligand, Protein L, SEQ ID NO: 116, or SEQ ID NO: 115.
10. A protein of any of embodiments 6-9 further including a flexible, rigid, or semi-rigid linker adjacent to the functional domain.
11. A protein of any of embodiments 1-10 wherein the protein exhibits high thermostability.
12. A protein of any of embodiments 1-11 wherein the protein exhibits high solubility.

13. A protein of any of embodiments 1-12 wherein the protein is self-folding.
14. A protein of any of embodiments 1-13 wherein the protein exhibits high thermostability, high solubility, and is self-folding
15. A protein having the formula: (a-b-x-y)$_n$ wherein
    a and x represent linker sequences;
    b represents an amino acid sequence that forms an alpha (α) helix;
    y represents an amino acid sequence that forms a second α helix;
    n=2 or more;
    each (a-b-x-y) unit is structurally repetitive to an adjacent (a-b-x-y) unit;
    the protein is handed; and
    the N- and C-termini of the protein create a circular architecture.
16. A protein of embodiment 15 wherein the protein exhibits high thermostability.
17. A protein of embodiment 15 or 16 wherein the protein exhibits high solubility.
18. A protein of any of embodiments 15-17 wherein the protein is self-folding.
19. A protein of any of embodiments 15-18 wherein the protein exhibits high thermostability, high solubility, and is self-folding.
20. A protein of any of embodiments 15-19 wherein the protein is left-handed.
21. A protein of any of embodiments 15-20 wherein the linker sequences are flexible linker sequences.
22. A protein of any of embodiments 15-20 wherein the linker sequences are GBB linker sequences.
23. A protein of embodiment 22 wherein the GBB linker sequences are selected from GKS; GIT; GTT; GYS; GDK; GDE; NDK; GDR; GDL; and GIS.
24. A protein of any of embodiments 15-23 wherein b and y have at least 98% sequence identity.
25. A protein of any of embodiments 15-23 wherein b and y have 100% sequence identity.
26. A protein of any of embodiments 15-23 wherein each (a-b-x-y) unit has at least 95% sequence identity with an adjacent (a-b-x-y) unit.
27. A protein of any of embodiments 15-23 wherein each (a-b-x-y) unit has 100% sequence identity with an adjacent (a-b-x-y) unit.
28. A protein of any of embodiments 15-23 wherein b and y are selected from SEQ ID NOs. 1-50; 124-129; 139; 140; 146; and/or 147.
29. A protein of any of embodiments 15-23 wherein a (a-b-x-y) unit is selected from SEQ ID NOs. 73-114; 130-134; 141-144; 172; and/or 148.
30. A protein of any of embodiments 15-29 including a sequence selected from SEQ ID NOs. 51-70; 117-123; 135-138 or 145.
31. A protein of any of embodiments 15-30 further including a functional domain (d) inserted in a (a-b-x-y) unit at a position selected from (d-a-b-x-y); (a-d-b-x-y); (a-b-d-x-y); (a-b-x-d-y); and (a-b-x-y-d).
32. A protein of any of embodiments 15-30 further including at least two functional domains inserted in at least two (a-b-x-y) units at positions selected from (d-a-b-x-y); (a-d-b-x-y); (a-b-d-x-y); (a-b-x-d-y); and/or (a-b-x-y-d).
33. A protein of embodiments 31 or 32 wherein the functional domain includes a cytokine, a Notch ligand, an immunogenic peptide, a peptide adjuvant, a single-chain class I MHC domain, or a small molecule ligand binding domain.
34. A protein of any of embodiments 31-33 wherein the functional domain includes SH2, SH3, IL-2, IL-3, IL-17c, single-chain MHC, the extracellular domain of the Delta-1 Notch protein ligand, Protein L, SEQ ID NO: 116, or SEQ ID NO: 115.
35. A protein any of embodiments 15-34 further including a flexible, rigid, or semi-rigid linker adjacent to the functional domain.
36. A protein having the formula: (a-b-x-y)$_n$ wherein
    a represents an amino acid sequence that forms an alpha (α) helix;
    x represents an amino acid sequence that forms a second α helix;
    b and y represent linker sequences;
    n=2 or more;
    each (a-b-x-y) unit is structurally repetitive to an adjacent (a-b-x-y) unit;
    the protein is handed; and
    the N- and C-termini of the protein create a circular architecture.
37. A protein of embodiment 36 wherein the linker sequences are flexible linker sequences.
38. A protein of embodiment 36 wherein the linker sequences are GBB linker sequences.
39. A protein of embodiment 38 wherein the GBB linker sequences are selected from GKS; GIT; GTT; GYS; GDK; GDE; NDK; GDR; GDL; and GIS.
40. A protein of any of embodiments 36-39 wherein b and y are selected from SEQ ID NOs. 1-50; 124-129; 139; 140; 146; and/or 147.
41. A protein of any of embodiments 36-40 further including a functional domain (d) inserted in a (a-b-x-y) unit at a position selected from (d-a-b-x-y); (a-d-b-x-y); (a-b-d-x-y); (a-b-x-d-y); and (a-b-x-y-d).
42. A protein of any of embodiments 36-41 further including at least two functional domains inserted in at least two (a-b-x-y) units at positions selected from (d-a-b-x-y); (a-d-b-x-y); (a-b-d-x-y); (a-b-x-d-y); and/or (a-b-x-y-d).
43. An artificially-designed circular, handed α-helical repeat protein (cTRP) wherein each repetitive α-helical structure includes an outer α helix and an inner α helix.
44. A cTRP of embodiment 43 wherein the outer α helix and the inner α helix are joined by a linker.
45. A cTRP of embodiment 44 wherein the linker is a flexible linker.
46. A cTRP of embodiment 44 wherein the linker is a GBB linker.
47. A cTRP of embodiment 46 wherein the GBB linker is a sequence selected from GKS; GIT; GTT; GYS; GDK; GDE; NDK; GDR; GDL; and GIS.
48. A cTRP of any of embodiments 43-47 wherein the outer α helix and the inner α helix are produced by a sequence selected from SEQ ID NOs. 1-50; 124-129; 139; 140; 146; and/or 147.
49. A cTRP of any of embodiments 43-48 including a sequence selected from SEQ ID NOs. 51-70; 117-123; 135-138 or 145.
50. A cTRP of any of embodiments 43-49 further including a functional domain.
51. A cTRP of any of embodiments 43-50 further including at least two functional domains.
52. A cTRP of embodiment 50 selected from SEQ ID NOs. 71; 72; 149; 150; or 151.

Example 1

Methods. Computational design. The repeat module design process applied here includes an initial "diversification" round of large-scale sampling followed by filtering and clustering and then a second "intensification" round of sampling focused on successful topologies identified in the first round.

Fragment assembly: Starting backbone models for sequence design are built using a fragment assembly protocol which is based on the standard Rosetta ab initio protocol (Simons, et al., J Mol Biol 268, 209-225, (1997)) with the following modifications: (1) fragment replacement moves are performed symmetrically across all repeats, guaranteeing that backbone torsion angles are identical at corresponding positions across repeats; (2) a pseudo-energy term (equal to the deviation between actual and desired curvature, in degrees, plus the deviation in rise multiplied by a factor of 5) is added to the potential to favor satisfaction of the geometric constraints; (3) the amino acid sequence used for low-resolution scoring is assigned randomly at the start of each simulation from secondary-structure specific distributions (helix: Ala+Ile+Leu+Asp+Ser, turn: Gly+Ser), which has the effect of increasing the diversity in helix packing distances and geometries compared with using a constant sequence such as poly-Val or poly-Leu.

Providing supplemental method information regarding fragment assembly, first round designs sampled helix lengths from 7 to 20 residues, turn lengths from 1 to 5 residues, and total repeat lengths ranging from 20 to 40 residues. At the start of each independent first round design trajectory the lengths of the secondary structure elements and turns are chosen randomly, defining the target secondary structure of the repeat module and its length. Together with the number of repeats, this defines the total length of the protein and the complete secondary structure, which is used to select 3 and 9 residue backbone fragments for use in the low-resolution fragment assembly phase.

Sequence design: The low-resolution fragment assembly simulation is followed by an all-atom sequence design stage including two cycles alternating between fixed-backbone sequence design and fixed-sequence structure relaxation. Symmetry of backbone and side chain torsion angles and sequence identities is maintained across all repeats. Since the starting backbones for design are built by relatively coarse sampling in a low-resolution potential, sequences designed with the standard all-atom potential are dominated by small amino acids and the resulting structures tend to be under-packed. To correct for this tendency, a softened Lennard-Jones potential (Dantas, et al., J Mol Biol 366, 1209-1221, (2007)) is used for the sequence design steps, while the standard potential is used during the relaxation step. The Rosetta "score12prime" weights set was used for these design calculations.

Filtering and clustering: Final design models (typically 10-100,000) are first sorted by per-residue energy (total energy divided by the number of residues, to account for varying repeat length) and the top 20% are filtered for packing quality, satisfaction of buried polar groups, and sequence-structure compatibility via a fast, low-resolution symmetric refolding test (40 trajectories, requiring at least 1 under a length-dependent RMSD threshold). Designs that pass these filters are clustered by C-α RMSD (allowing for register shifts when aligning helices with unequal lengths) in order to identify recurring architectures. The clusters are ranked by averaging residue energy, packing quality, and refolding success over all cluster members.

Providing supplemental method information regarding filtering and clustering, the following filtering thresholds were used: sasapack_score<0.5, # buried unsatisfied donors per repeat<1.5, # buried unsatisfied acceptors per repeat<0.5, refolding RMSD threshold of 2 Angstroms for 3-repeat designs, and 4 Angstroms for larger designs.

Resampling: During the second round of designs, representative topologies from successful design clusters are specifically resampled by enforcing their helix and turn lengths as well as their turn conformations (defined using a 5-state, coarse-grained backbone torsion alphabet (Wintjens, et al., J Mol Biol 255, 235-253, (1996))) during fragment selection.

Providing supplemental method information regarding resampling, the following boundaries were used for the coarse-grained Ramachandran alphabet1 (FIG. 19):

'A'=(phi<=0, -125<psi<=50), 'B'=(phi<=0, psi>50 or psi<=-125); 'G'=(phi>0, -100<psi<=100); 'E'=(phi>0, psi>100 or psi<=-100), and 'O'=(|omega|<90).

Large-scale refolding: Selected low-energy designs from the second round that pass the filters described above are evaluated by a large-scale refolding test in which 2,000-10,000 ab initio models are built by standard (asymmetric) fragment assembly followed by all-atom relaxation. Success is measured by assessing the fraction of low energy ab initio models with RMSDs to the design model under a length-dependent threshold.

Symmetry-breaking in the central pore: For designed toroids with an open, polar central pore, perfect symmetry may not allow optimal electrostatic interactions between nearby side chains corresponding to the same repeat position in successive repeats. Symmetry-breaking mutations were therefore explored at a handful of inward-pointing positions via fixed-backbone sequence design simulations in which the length of the repeating sequence unit was doubled/tripled (for example, whereas perfect 6-fold repeat symmetry would require KKKKKK (SEQ ID NO: 156) or EEEEEE (SEQ ID NO: 157), doubling the repeat length permits charge complementarity with KEKEKE (SEQ ID NO: 158)). Solutions from these designs were accepted if they significantly lowered the total energy.

Structural bioinformatics: To assess similarity between design models and proteins in the structural database, searches were performed using the structure-structure comparison program DALI33 as well as consulting the protein structure classification databases CATH34, SCOPe35, and ECOD36. Further details are given elsewhere herein.

Cloning and Protein Expression. The plasmids encoding individual constructs were cloned into previously described bacterial pET15HE expression vectors (Mak et al., Science 335(6069):716-9, (2012)) including a cleavable N-terminal His-tag and an ampicillin resistance cassette.

Sequence verified plasmids were transformed into BL21 (DE3)RIL *E. coli* cells (Agilent Technologies) and plated on LB medium with ampicillin (100 µg/mL). Colonies were individually picked and transferred to individual 10 mL aliquots of LB-Ampicillin media and shaken overnight at 37° C. Individual 10 mL aliquots of overnight cell cultures were added to individual 1 L volumes of LB-Ampicillin, which were then shaken at 37° C. until the cells reached an OD600 value of 0.6 to 0.8. The cells were chilled for 20 minutes at 4° C., then IPTG was then added to each flask to a final concentration of 0.5 mM to induce protein expression. The flasks were shaken overnight at 16° C., and then pelleted by centrifugation and stored at -20° C. until purification.

Construct dTor_6×35L(SeMet), incorporating a single Methionine residue at position 168 in the original design construct, was generated using a 'QuikChange' site-directed mutagenesis kit (Agilent) and corresponding protocol from the vendor. The resulting plasmid construct was again transformed into BL21(DE3)RIL *E. coli* cells (Agilent Technologies) and plated on LB plates including ampicillin (100 µg/mL) and chloramphenicol (35 g/mL). Subsequent cell culture and protein expression in minimal media, along with incorporation of selenomethionine was incorporated during protein expression according to reference Walden et al., Acta Crystallogr D Biol Crystallogr. April 1; 66(Pt 4): 352-357 (2010).

Purification. Cell pellets from 3L of cell culture were resuspended in 60 mL of PBS solution (140 mM NaCl, 2.5 mM KCl, 10 mM NaHPO4, 2 mM KH2PO4) including 10 mM imidazole (pH 8.0). Cells were lysed via sonication and centrifuged to remove cell debris. The supernatant was passed through a 0.2 micron filter, and then incubated on a rocker platform at 4° C. for one hour after adding 3 mL of resuspended Nickel-NTA metal affinity resin (Invitrogen). After loading onto a gravity-fed column, the resin was washed with 45 mL of the same lysis buffer described above, and the protein was eluted from the column with three consecutive aliquots of PBS including 150 mM imidazole (pH 8.0). Purified protein was concentrated to 5 mg/mL to 25 mg/mL while buffer exchanging into 25 mM Tris (pH 7.5) and 200 mM NaCl and then further purified via size exclusion chromatography using HiLoad 16/60 Superdex 200 column (GE).

Protein samples were then split in half; one sample was used directly for crystallization while the other had the His-tag removed by an overnight digest with biotinylated thrombin (Novagen), prior to additional crystallization trials. The digested sample was incubated for 30 minutes with streptavidin-conjugated agarose (Novagen) to remove the thrombin. All samples were tested for purity and removal of the His-tag via SDS PAGE. The final protein samples, both with and without the N-terminal poly-histidine affinity tag, were concentrated to values of 5 mg/mL to 25 mg/mL for crystallization trials.

Solution Size and Stability Analysis. Proteins at a concentration of 4 to 10 mg/ml were run over a Superdex 75 10/300 GL column (GE Healthcare) in 25 mM Tris pH 8.0 plus 100 or 750 mM NaCl at a rate of 0.4 ml/min on an AKTAprime plus chromatography system (GE Healthcare). All fractions including eluted toroid protein (visualized via electrophoretic gel analyses) were pooled, concentrated and run over the column a second time in order to assess their solution oligomeric behavior using protein with a minimal background of contaminants. Gel filtration standards (Bio-Rad) were run over the same column in matching buffer, and the UV trace of the proteins was overlaid onto the standards using UNICORN 5 software (GE Healthcare).

For measurements of protein stability using circular dichroism (CD) spectroscopy, purified recombinant toroid constructs were diluted to between 10 to 20 µM concentration and dialyzed overnight into 10 mM potassium phosphate buffer at pH 8.0. Circular dichroism (CD) thermal denaturation experiments were performed on a JASCO J-815 CD spectrometer with a Peltier thermostat. Wavelength scans (190-250 or 260 nm) were carried out for each construct at 22° C. and 95° C. or 80° C. (see FIGS. 1D, 2D, 3D, 4D, 5D, 6D, 7D, 9D). Additional thermal denaturation experiments were conducted by monitoring CD signal strength at 206 nm over a temperature range of 4° C. to 95° C. (0.1 cm pathlength cell), with measurements taken every 2 degrees. Sample temperature was allowed to equilibrate for 30 seconds before each measurement.

Crystallization and Data Collection. Purified proteins were initially tested for crystallization via sparse matrix screens in 96-well sitting drops using a mosquito (TTP LabTech). Crystallization conditions were then optimized with constructs that proved capable of crystallizing in larger 24-well hanging drops. Out of 11 constructs that were purified to homogeneity, ten were crystallized, of which five yielded high quality x-ray diffraction that resulted in successful structure determination. dTor_6×35L was crystallized in 160 mM Sodium Chloride, 100 mM Bis-Tris pH 8.5 and 24% (w/v) Polyethylene Glycol 3350 at a concentration of 26 mg/mL. The crystal was transferred to a solution including 300 mM, then 500 mM Sodium Chloride and flash frozen in liquid nitrogen. Data was collected on a R-AXIS IV++ and processed on HKL20004.

dTor_6×35L(SeMet) was crystallized in 140 mM Sodium Chloride, 100 mM Tris pH 8.5 and 22% (w/v) Polyethylene Glycol 3350 at a concentration of 26 mg/mL. The crystal was transferred to a solution including 300 mM, then 500 mM Sodium Chloride and flash frozen in liquid nitrogen. Data was collected at ALS Beamline 5.0.2 at wavelength 0.9794 Angstroms and processed on HKL20004.

dTor_3×33L_2-2 was crystallized in two different conditions, producing two different crystal lattices. The first condition had 30% Polyethylene Glycol 3350, 100 mM Tris pH 6.5, 200 mM NaCl with a protein concentration of 1.8 mM. The protein was soaked in a 15% Ethylene Glycol cryoprotectant for one minute prior to being flash frozen in liquid nitrogen. Data was collected on a Saturn 944+ (Rigaku) for 180 degrees at phi=0 and another 180 degrees at phi=180. Data was then processed on HKL20004 out to 1.85 Å in space group P212121.

The second condition had 45% Polyethylene Glycol 400 and 100 mM Tris pH 7.7 with a protein concentration of 1.8 mM. Protein crystal was flash frozen without being cryoprotected. Data was collected on a Saturn 944+(Rigaku) for 180 degrees at phi=0 and another 180 degrees at phi=180. Data was then processed on HKL20004 out to 1.85 Å in space group P43212.

dTor_9×31L_sub3 was crystallized in 100 mM Tris pH 8.5 and 15% (v/v) Ethanol at a concentration of 11.5 mg/mL. The crystal was transferred to a solution including 75 mM Tris pH 8.5, 7.5% (v/v) Ethanol and 25% (v/v) Glycerol and flash frozen in liquid nitrogen. Data was collected at ALS BL5.0.2 and processed on HKL20004 out to 2.9 Å in space group P 41 21 2/P 43 21 2.

dTor_9×31L was crystallized in 0.1 M Sodium Citrate pH 5.4 and 1.0 M Ammonium Phosphate Monobasic at a concentration of 8.8 mg/mL in 3 ul drops including 1 ul protein and 2 ul well solution. The crystal was transferred to a solution including the well plus 25% (v/v) Glycerol and flash frozen in liquid nitrogen. Data was collected on a Saturn 944+CCD and processed on HKL20004 out to 2.5 Å in space group P 21 21 21.

dTor_12×31L was crystallized in 0.9 M Sodium malonate pH 7.0, 0.1 M HEPES pH 7.0 and 0.5% Jeffamine ED-2001 pH 7.0 at a concentration of 8.8 mg/mL in 2 ul drops including 1 ul protein and 1 ul well solution. The crystal was transferred to a solution including 0.675 M Sodium malonate pH 7.0, 0.075 M HEPES pH 7.0, 0.375% Jeffamine ED-2001 pH 7.0 and 25% Glycerol, and flash frozen in liquid nitrogen. Data was collected on a Saturn 944+ CCD and processed on HKL20004 out to 2.3 Å in space group R 3:H.

Phasing and Refinement. The dTor_6×35L and both dTor_3×33L_2-2 structures were solved by Molecular Replacement with Phaser5 via CCP4i6 using the Rosetta-designed structure as a search model. The structures were then built and refined using Coot7 and Refmac58, respectively.

The structure of dTor_6×35L(SeMet) was solved by Molecular Replacement with Phaser5 via PHENIX9 using the best refined model of dTor_6×35L as a phasing model. The structure was then built and refined using Coot7 and PHENIX10, respectively.

The structures of dTor_9×31L_sub3 and dTor_9×31L were solved by Molecular Replacement with Phaser5 via PHENIX9 using the Rosetta-designed structure as a search model. The structure was then built and refined using Coot7 and PHENIX10, respectively.

The structure of dTor_12×31L was solved by Molecular Replacement with Phaser5 via PHENIX9 using a 4 repeat subunit the Rosetta-designed structure as a search model. The structure was then built and refined using Coot7 and PHENIX10, respectively.

Additional Supporting Methods. Design model for dTor_12×31L: The 12×31L design was constructed by duplicating the final 3 repeats of the 9×31L design. To generate a "design model" for comparison with the experimentally determined structure, the round 2 design protocol now forcing the 12×31L repeat sequence in addition to the number of repeats (Main, et al., Structure 11, 497-508 (2003)) and the helix and turn lengths (H14-L3-H11-L3) and turn conformations (GBB) was followed. Thus the sequence design steps were reduced to rotamer optimization (since the amino acid identities were fixed). This symmetric structure prediction process was repeated 10,000 times and the lowest-energy final model was taken as the computational model.

Surface mutations to enhance crystallization: For a single representative of the 3×31L and 6×31R families lattice docking and design simulations were performed to select mutations that might promote crystallization. Core positions were frozen at the design sequence. Candidate space groups were selected from those most commonly observed in the protein structural database. Theoretical models of crystal packing arrangements were built by randomly orienting the design model within the unit cell and reducing the lattice dimensions until clashes were encountered. Symmetric interface design was performed on these docked arrangements, and final designs were filtered by energy, packing, satisfaction of polar groups, and number of mutations from the original design model.

Handedness of repeat helical bundles: To compute the handedness of helical bundles formed by cTRPs, an approximate helical bundle axis curve was generated by joining the location of repeat-unit centers of mass in a sliding fashion along the protein chain. The handedness was then estimated by computing the directionality of the winding of the polypeptide chain about this axis curve.

Summary of Example 1

Example 1 described creation and characterization of cTRPs including: 3 repeats, 6 repeats, 9 repeats, and 12 repeats. Characterization included (i) protein expression and purification; (ii) size determination using gel filtration chromatography (also termed 'size exclusion chromatography or 'SEC') and dynamic light scattering ('DLS') (iii) demonstration of thermostability using circular dichroism spectroscopy ('CD') and (iv) determination of high resolution molecular structures using X-ray Crystallography. Example 1 also provided demonstration that cTRPs can also be assembled from smaller protein subunits including a fraction of the total number of repeats found in the fully circularized protein constructs (e.g., generation of a circular protein including 12 repeats from the assembly of four identical subunits each including 3 repeats).

Example 2

Methods. Protein Expression and Purification. Designed constructs were cloned into a previously described bacterial expression vector, named 'pET15HE', which incorporates a cleavable N-terminal poly-histidine affinity tag and a thrombin cleavage site (Mak et al., Science 335(6069): 716-9, (2012)).

Sequence verified plasmids were transformed into BL21 (DE3) RIL *E. coli* cells and plated on LB-Amp plates to grow at 37° C. Colonies were grown in 10 mL overnight cultures of LB+Amp (100 μg/mL) and diluted 1:100 the next day to a final volume of 1 L. Cell cultures were shaken at 37° C. until the cells reached an OD600 between 0.6-0.8. Cells were then incubated on ice for 30 minutes, induced with 200 mM IPTG, and incubated overnight at 16° C. Induced cells were pelleted and stored at −20° C. Successful protein induction was verified by SDS-PAGE.

Cell pellets were resuspended in a buffer including 25 mM Tris/HCl pH 7.5, 200 mM NaCl, and 5% glycerol. PMSF and benzonase (Sigma-Aldrich) were added to 1 mM concentrations prior to sonication. Cell debris was pelleted and the supernatant was filtered through a 0.20 μm filter.

His-tagged proteins were incubated with pre-equilibrated Nickel-NTA resin (3 mL bed volume), gravity-loaded onto a column, and washed with buffer including increasing concentrations of imidazole at pH 8.0. Fractions including eluted protein were concentrated and exchanged to a thrombin cleavage buffer (0.3 M NaCl, 25 mM Tris pH 7.5, and 5% v/v glycerol). The His-tag was removed with an overnight incubation at 4° C. with biotinylated thrombin. The following morning, streptavidin-conjugated agarose resin was added to the sample and incubated for 30 minutes at room temperature. Thrombin was then removed by gravity filtration over an empty column, and pure, tagless protein was collected.

Determination of apparent molecular mass using size exclusion chromatography ('SEC'). The constructs were then concentrated to 5-20 mg/mL and passed over a size exclusion chromatography (SEC) column (15 mL Superdex 200 10/300 GL, GE Life Sciences) in the presence of 25 mM Tris/HCl pH 7.5, 200 mM NaCl, and 5% glycerol. The apparent molecular weight of the purified construct was determined based on interpolation of each construct's elution volume relative to a set of protein-based molecular weight standards.

Determination of hydrodynamic radius using Dynamic Light Scattering ('DLS'). The average hydrodynamic radii and diameter of protein constructs were characterized by measuring the diffusion rate of those particles moving under Brownian motion. Designs were measured in 1×PBS (Phosphate buffered Saline; 10 mM P043-, 137 mM NaCl, and 2.7 mM KCl) at a protein concentration of 1 mg/mL and temperature of 25° C. on a Zetasizer Nano Series instrument (Malvern Instruments).

Determination of thermal stability using CD spectroscopy. Purified recombinant meganuclease constructs were diluted to between 10-20 μM concentration and dialyzed overnight into 10 mM potassium phosphate buffer at pH 8.0. Circular dichroism (CD) spectra were then collected on a JASCO J-815 CD spectrometer with a Peltier thermostat. Wavelength scans extending from 190-250 nm were carried out for each construct at 22° C. and 95° C.

Crystallization and Structure Determination. Protein samples, both before and after proteolytic removal of the poly-histidine purification tag, were screened for initial crystals in broad sparse matrix screens using nanoliter volume sitting drops in a Mosquito crystallization robotic platform (LabTech TTP). Promising hits were then optimized, when necessary in a larger microliter hanging drop format. Data were collected using X-rays generated either on a rotating anode MicroMax-007HF generator (Rigaku) or at the Advanced Light Source (ALS) beamline 5.0.2 (Lawrence Berkeley National Laboratory). Structures were solved via Molecular Replacement, using initial designed models, using program Phaser (Mccoy et al., J Appl Crystallogr 40: 658-674, (2007)) and went through multiple rounds of refinement and rebuilding using Refmac5 (Skubak et al., Acta Crystallogr D 60: 2196-2201, (2004)) or Phenix.refine (Afonine et al., Acta Crystallogr D 68: 352-367, (2012)) and Coot (Emsley et al., Acta Crystallogr D 66: 486-501, (2010)). Validation of final structures was performed using MolProbity (Chen et al., Acta Crystallogr D 66: 12-21, (2010)) and RCSB's validation server, and were then deposited into the RCSB (Berman et al., Nucleic Acids Res 28: 235-242 (2000)).

SAXS analyses. Purified proteins were transferred by dialysis into 150 mM NaCl, 25 mM Tris pH 8.0, 2% glycerol at protein concentrations ranging from 10 mg/mL to 2 mg/mL. SAXS data were collected on the SIBYLS small angle x-ray scattering beamline at the Advanced Light Source (Lawrence Berkeley National Laboratory) using a Pilatus3 2 M detector with exposure times of 0.5, 1, 2, and 4 seconds. Data was processed using program SCATTER.

Determination of ligand binding using Fluorescence Polarization (FP): Each protein construct was 2-fold serially diluted into twelve concentrations, from 23 µM to 0.011 µM, using FP Buffer (20 mM HEPES+150 mM KCl at pH7.4). A 90 uL aliquot of each concentration was mixed with 10 µL of 0.5 µM FITC-labeled peptide so the final concentrations were 20.7 µM to 0.01 µM with 50 nM peptide. Each reaction was incubated at room temperature, protected from light, for 20 minutes. FP was run using a SpectraMax M5 (Molecular Devices) at an excitation of 485 nm and emission of 525 nm. Background was subtracted from raw perpendicular and parallel fluorescence intensity, which were then converted to fluorescence polarization (mP) by the following equation:

$$mP = \frac{F_{\parallel} - F_{\perp}}{F_{\parallel} + F_{\perp}} * 1000$$

where, $F_{\parallel}$=adjusted parallel intensity and $F_{\perp}$=adjusted perpendicular intensity Example 2 describes expansion of the cTRP scaffolds out to constructs including 24 repetitive α-helical structures in a single protein construct. These constructs were characterized using all the methods noted above in Example 1, except for X-ray crystallography (because crystals of these constructs do not diffract to appropriate resolution for a full analysis). Structural characterization for these constructs was instead performed using small angle X-ray scattering ('SAXS') analyses.

Example 2 also provides expansion of the cTRP scaffolds in the '3rd' dimension (i.e. increasing their thickness, rather than their diameter) to increase the designable 'surface area' between each protein repeat and between the N- and C-termini of each protein subunit within those constructs. These constructs have been characterized by protein expression and purification, as well as SEC and DLS (FIG. 10C).

Example 2 also further explored the functionalization of cTRPs by grafting several different binding domains and cell signaling protein subunits onto their exterior. Particularly, variable numbers (1, 2, 4, and 6) of a peptide-binding domain (the SH2 domain from the Nck2 cell signaling adapter protein, which is 100 amino acids in size) have been incorporated into a cTRP scaffold harboring 12 repeats. This domain recognizes and binds a peptide sequence corresponding to "N-Glu-His-Ile-pTyr-Asp-Glu-Val-Ala-Ala-Asp-C", (SEQ ID NO: 159) which was used for binding analyses. In these particular constructs, a minimum length protein linker required for folding and function of the SH2 domain functional domain appears to be 8 residues, currently GGSGGGSG (SEQ ID NO: 160).

Peptide binding function and behavior of these constructs, relative to 'free' SH2 domain, using both fluorescence polarization ('FP') and surface plasmon resonance ('SPR') was explored. Constructs including 4 or 6 copies of SH2 (i.e. that have a ratio of 1 SH2 per 3 repeats or 1 SH2 per 2 repeats) display aggregation behavior, presumably due to steric crowding and subtle misfolding behavior (i.e. there's not quite enough room for them to all fit). These constructs, however, still display binding activity. Conversely, constructs including 1 or 2 SH2 domains (i.e. that display a ratio of 1 SH2 per 12 or 6 repeats) are well-behaved. Thus, it is believed that a minimum ratio of SH2 inserts to repeats is '6' (i.e. 6 repeats per SH2 insert are required for assembly, folding and function) is an optimized format for these embodiments. As this indicates, functionalization of the cTRPs with particular functional domains will require some experimentation and optimization. This experimentation is well within the ordinary skill level in the art following the extensive teachings provided herein. A toroid with 3 copies of SH2 within a 12-repeat cTRP and another toroid with 4 copies of SH2 within a 12-repeat cTRP, where the SH2 copies alternate between the 'top' and 'bottom' surfaces of the toroid will also be created and analyzed.

cTRPs with 12 or 24 repeats and including variable numbers of the IL-2 cytokine (a larger protein including 130 residues) have also been created. First, variable numbers (2, 3 and 4) of IL-2 were incorporated into a cTRP scaffold including 12 repeats. The construct including 2 copies of IL-2 expressed and purified well, but size analysis using SEC indicates that the protein formed large, presumably aggregated protein assemblages. The constructs including 3 or 4 copies of IL-2 expressed but formed fully insoluble inclusion bodies and were not usable in further experiments. Thus, 4 or 6 IL-2 molecules were incorporated onto a split cTRP scaffold including 24 repeats total. The construct including 4 copies of IL-2 (including four protein subunits that each include 1 copy of IL-2 embedded in 6 protein repeats) has been expressed, purified, and its size determined using SEC and DLS. It is well behaved folds into the expected dimensions and size relative to the 'naked' cTRP including 24 unmodified repeats. The protein is currently undergoing SAXS analysis to further examine its dimensions. Furthermore, a monomeric, 'single-chain' version of the 24-repeat toroid harboring 4 copies of IL-2 for a comparative analysis of size, behavior and function has been created.

A construct including 4 copies of a single-chain MHC protein harboring an immunogenic peptide from cytomegalovirus, in a cTRP including 24 repeats has also been created (see FIGS. 24A-24D, SEQ ID NO: 167). As above, this construct includes four identical protein subunits that each include 1 copy of sc-MHC embedded in 6 protein repeats. It has been demonstrated that this construct can be expressed at very high levels (200 mg per liter) from human HEK293T cells in suspension, and easily purified directly from corresponding cell culture media. This demonstrates that the cTRP platform is compatible with human cell culture, allowing production under conditions required for therapeutic use. However, this construct does not appear to be properly self-assembling to generate a cTRP, but instead appears to be remaining as separate protein subunits in solution. Without being bound by theory, it is believed this is due to the strategy used to graft the scMHC molecule onto the cTRP repeats; instead of embedding the protein in between repeats, it is instead fused to the N-terminus of each protein (while the C-terminus is simultaneously occupied with a purification tag). This construct will be altered to remove extra residues from the C-terminus of each subunit, and rescue of the assembly is expected. This protein will also be used in a larger cTRP with more surface area available to drive and control assembly.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in the handed repetitive nature of the alpha-helical structure as measured by RMSD. Within this context, a structure is repetitive when, following stacking and comparison, the distance between corresponding atoms of the stacked outer α-helix and the stacked inner α-helix is within 2 Å.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A protein comprising the formula:

[(d-a-b-x-y)$_1$(a-b-x-y)$_5$]$_4$ wherein d is a single-chain protein domain comprising a class I major histocompatibility complex (MHC)-peptide complex;
a is GLN;
x is GIS;
b is SEQ ID NO: 124;
y is SEQ ID NO: 125 or SEQ ID NO: 129;
the protein is left-handed; and
the N- and C-termini of the protein create a circular architecture.

2. The protein of claim 1, wherein each (a-b-x-y) unit has the sequence set forth in SEQ ID NO: 130 or SEQ ID NO: 134.

3. The protein of claim 1, wherein each (a-b-x-y) unit that is not an end unit of the protein has 100% sequence identity with an adjacent (a-b-x-y) unit.

4. The protein of claim 1, wherein the protein exhibits high thermostability, high solubility, and is self-folding.

5. The protein of claim 1, wherein the N- and C-termini of the protein create a closed architecture.

6. A protein having the formula: (a-b-x-y)n wherein
a represents a linker sequence;
x represents a linker sequence;
b represents an amino acid sequence that forms an alpha (α) helix;
y represents an amino acid sequence that forms a second α helix;
n=2 or more;
each (a-b-x-y) unit is structurally repetitive to an adjacent (a-b-x-y) unit,
the protein is left-handed;
the N- and C-termini of the protein create a circular architecture, and
wherein the feature of structurally repetitive is determined by stacking each (a-b-x-y) unit with an adjacent (a-b-x-y) unit, and after stacking, the distance between corresponding atoms of the stacked outer α-helices and the stacked inner α-helices is within 2 angstrom (Å) measured using root-mean-square deviation (RMSD).

7. The protein of claim 6, wherein b has the sequence set forth in SEQ ID NO: 124 in at least one (a-b-x-y) unit.

8. The protein of claim 6, wherein y has the sequence set forth in SEQ ID NO: 125 in at least one (a-b-x-y) unit.

9. The protein of claim 6, wherein y has the sequence set forth in SEQ ID NO: 129 in at least one (a-b-x-y) unit.

10. The protein of claim 6, wherein b and y are selected from the sequence set forth in SEQ ID NOs. 1-50; 124-129; 139; 140; 146; or 147 provided that b and y are not the same sequence.

11. The protein of claim 6, wherein at least one (a-b-x-y) unit has the sequence set forth in SEQ ID NO: 130.

12. The protein of claim 6, wherein at least one (a-b-x-y) unit has the sequence set forth in SEQ ID NO: 134.

13. The protein of claim 6, wherein a (a-b-x-y) unit has the sequence set forth in Previously Presented SEQ ID NOs. 73-114; 130-134; 141-144; 172; or 148.

14. The protein of claim 6, wherein the linker sequences comprise GBB linker sequences.

15. The protein of claim 14, wherein the GBB linker sequences are selected from GKS; GIT; GTT; GYS; GDK; GDE; NDK; GDR; GDL; and GIS.

16. The protein of claim 6, comprising a functional domain (d) at the N-terminus of at least one (a-b-x-y) unit.

17. The protein of 68, wherein the functional domain comprises SH2, SH3, IL-2, IL-3, IL-17c, a single-chain MHC domain, the extracellular domain of the Delta-1 Notch protein ligand, Protein L, the sequence set forth in SEQ ID NO: 116, or the sequence set forth in SEQ ID NO: 115.

18. The protein of claim 6, wherein n=24.

19. The protein of claim 18, comprising a functional domain (d) at the N-terminus of the first (a-b-x-y) unit, the N-terminus of the seventh (a-b-x-y) unit, the N-terminus of the thirteenth (a-b-x-y) unit, and the N-terminus of the nineteenth (a-b-x-y) unit.

20. The protein of 71, wherein the functional domain comprises SH2, SH3, IL-2, IL-3, IL-17c, a single-chain MHC domain, the extracellular domain of the Delta-1 Notch protein ligand, Protein L, or the sequence set forth in SEQ ID NO: 116, or the sequence set forth in SEQ ID NO: 115.

* * * * *

UNITED STATES PATENT AND TRADEMARK OFFICE
CERTIFICATE OF CORRECTION

PATENT NO. : 10,597,466 B2  
APPLICATION NO. : 15/780397  
DATED : March 24, 2020  
INVENTOR(S) : Philip Bradley et al.

Page 1 of 1

It is certified that error appears in the above-identified patent and that said Letters Patent is hereby corrected as shown below:

In the Claims

In Column 160, Line 57, cancel the text "Previously Presented";

In Column 160, Line 66, the claim reference numeral "68" should read --16--.

In Column 161, Line 10, the claim reference numeral "71" should read --19--.

Signed and Sealed this  
First Day of June, 2021

Drew Hirshfeld  
*Performing the Functions and Duties of the*  
*Under Secretary of Commerce for Intellectual Property and*  
*Director of the United States Patent and Trademark Office*

```
                              SEQUENCE LISTING

<160> NUMBER OF SEQ ID NOS: 175

<210> SEQ ID NO 1
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 1

Val Glu Glu Leu Leu Lys Leu Ala Lys Ala Ala Tyr Tyr Ser
1               5                   10

<210> SEQ ID NO 2
<211> LENGTH: 11
<212> TYPE: PRT
<213> ORGANISM: Artificial Sequence
<220> FEATURE:
<223> OTHER INFORMATION: alpha-helix generating peptide

<400> SEQUENCE: 2

Val Glu Glu Ala Tyr Lys Leu Ala Leu Lys Leu
1               5                   10

<210> SEQ ID NO 3
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 3

Val Glu Glu Leu Leu Lys Leu Ala Glu Ala Ala Tyr Tyr Ser
1               5                   10

<210> SEQ ID NO 4
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 4

Pro Thr Glu Ala Leu Leu Lys Leu Ile Ala Glu Ala Lys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: alpha-helix generating peptide
```

<400> SEQUENCE: 5

Glu Thr Glu Ala Lys Glu Glu Ala Glu Lys Ala Leu Lys Glu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 6

Ser Thr Glu Ala Lys Glu Glu Ala Ile Lys Ala Leu Lys Glu
1               5                   10

<210> SEQ ID NO 7
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 7

Glu Leu Glu Ala Lys Val Leu Ala Glu Lys Ala Leu Lys Glu
1               5                   10

<210> SEQ ID NO 8
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 8

Glu Thr Glu Ala Lys Leu Glu Ala Glu Lys Ala Leu Lys Glu
1               5                   10

<210> SEQ ID NO 9
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 9

Pro Thr Glu Val Leu Leu Glu Leu Ile Ala Glu Ala Ser
1               5                   10

<210> SEQ ID NO 10
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 10

Lys Glu Glu Val Lys Glu Lys Phe Leu Lys Glu Leu Ser Lys
1               5                   10

<210> SEQ ID NO 11
<211> LENGTH: 14
<212> TYPE: PRT
<213> ORGANISM: Artificial Sequence
<220> FEATURE:
<223> OTHER INFORMATION: alpha-helix generating peptide

```
<400> SEQUENCE: 11

Lys Glu Glu Val Lys Arg Lys Phe Leu Lys Glu Leu Ser Lys
1               5                   10

<210> SEQ ID NO 12
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 12

Lys Ala Glu Val Lys Arg Glu Phe Leu Trp Glu Leu Ser Leu
1               5                   10

<210> SEQ ID NO 13
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 13

Lys Glu Glu Val Lys Glu Lys Phe Leu Ala Glu Leu Glu Lys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 14

Arg Glu Glu Val Lys Glu Lys Phe Leu Lys Glu Leu Arg Lys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 15

Lys Glu Glu Val Lys Glu Lys Phe Leu Lys Glu Leu Ser Phe
1               5                   10

<210> SEQ ID NO 16
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 16

Lys Glu Glu Val Lys Lys Lys Phe Trp Lys Glu Leu Ser Leu
1               5                   10

<210> SEQ ID NO 17
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 17
```

-continued

Lys Glu Glu Val Lys Lys Phe Trp Lys Glu Leu Ser Leu
1               5                   10

<210> SEQ ID NO 18
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 18

Lys Ala Glu Val Lys Leu Lys Phe Leu Phe Glu Leu Ser Phe
1               5                   10

<210> SEQ ID NO 19
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 19

Lys Glu Glu Val Lys Glu Lys Phe Leu Lys Glu Leu Phe Lys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 20

Thr Thr Glu Ala Leu Leu Ile Leu Ile Ala Glu Ala Ser
1               5                   10

<210> SEQ ID NO 21
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 21

Val Glu Gln Gln Lys Gln Arg Phe Lys Glu Leu Val Lys Lys
1               5                   10

<210> SEQ ID NO 22
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 22

Thr Ala Ile Ala Gln Ile Leu Ala Ile Lys Ala Ser Ala Lys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 23

```
Thr Glu Leu Glu Arg Ala Leu Arg Tyr Ala Lys Lys Val
1               5                   10
```

<210> SEQ ID NO 24
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 24

```
Thr Glu Leu Glu Arg Ala Leu Arg Tyr Ala Val Lys Val
1               5                   10
```

<210> SEQ ID NO 25
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 25

```
Thr Glu Leu Glu Gln Ala Leu Arg Tyr Ala Lys Phe Val
1               5                   10
```

<210> SEQ ID NO 26
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 26

```
Leu Glu Leu Thr Arg Ala Leu Ala Tyr Ala Lys Lys Val
1               5                   10
```

<210> SEQ ID NO 27
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 27

```
Thr Glu Leu Glu Arg Ala Leu Arg Tyr Ala Lys Leu Val
1               5                   10
```

<210> SEQ ID NO 28
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 28

```
Thr Glu Leu Glu Arg Ala Leu Arg Tyr Ala Lys Tyr Val
1               5                   10
```

<210> SEQ ID NO 29
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 29

```
Pro Glu Leu Glu Tyr Ala Leu Ala Tyr Ala Lys Lys Val
```

```
1               5                   10
```

<210> SEQ ID NO 30
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 30

```
Thr Glu Leu Glu Arg Ala Leu Ile Phe Ala Glu Ala Val
1               5                   10
```

<210> SEQ ID NO 31
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 31

```
Thr Glu Leu Asp Arg Ala Leu Trp Tyr Ala Lys Lys Val
1               5                   10
```

<210> SEQ ID NO 32
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 32

```
Thr Glu Leu Glu Arg Ala Leu Leu Tyr Ala Lys Lys Val
1               5                   10
```

<210> SEQ ID NO 33
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 33

```
Thr Glu Leu Glu Arg Ala Leu Ala Tyr Ala Arg Leu Val
1               5                   10
```

<210> SEQ ID NO 34
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 34

```
Thr Glu Leu Glu Arg Ala Leu Ala Tyr Ala Arg Leu Val
1               5                   10
```

<210> SEQ ID NO 35
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 35

```
Thr Glu Leu Glu Arg Ala Leu Trp Tyr Ala Lys Lys Val
1               5                   10
```

<210> SEQ ID NO 36
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 36

Ser Ala Ile Ala Thr Ala Tyr Ile Ala Leu Ala Glu Tyr Leu
1               5                   10

<210> SEQ ID NO 37
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 37

Glu Ala Leu Leu Lys Ala Ile Glu Ile Ala Ile Lys Leu
1               5                   10

<210> SEQ ID NO 38
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 38

Ser Ala Ile Ala Glu Ala Tyr Ile Ala Leu Ala Arg Tyr Leu
1               5                   10

<210> SEQ ID NO 39
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 39

Ser Ala Leu Ala Gln Ile Leu Ala Ile Tyr Ala Ser Ala Tyr
1               5                   10

<210> SEQ ID NO 40
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 40

Thr Leu Phe Leu Arg Ala Leu Lys Leu Ala Lys Glu Val
1               5                   10

<210> SEQ ID NO 41
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 41

Glu Leu Tyr Ile Arg Val Leu Ala Ile Val Ala Glu Ala Glu
1               5                   10

```
<210> SEQ ID NO 42
<211> LENGTH: 13
<212> TYPE: PRT
<213> ORGANISM: Artificial Sequence
<220> FEATURE:
<223> OTHER INFORMATION: alpha-helix generating peptide

<400> SEQUENCE: 42

Thr Lys Leu Glu Leu Ala Leu Lys Leu Ala Leu Lys Lys
1               5                   10

<210> SEQ ID NO 43
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 43

Lys Leu Tyr Ile Glu Val Leu Ala Ile Val Ala Glu Ala Glu
1               5                   10

<210> SEQ ID NO 44
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 44

Glu Leu Tyr Ile Arg Val Leu Ala Ile Val Ala Lys Ala Glu
1               5                   10

<210> SEQ ID NO 45
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 45

Lys Leu Tyr Ile Glu Val Leu Ala Ile Val Ala Lys Ala Glu
1               5                   10

<210> SEQ ID NO 46
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 46

Leu Glu Gln Ala Leu Lys Ile Leu Lys Val Ala Ala Glu Leu
1               5                   10

<210> SEQ ID NO 47
<211> LENGTH: 15
<212> TYPE: PRT
<213> ORGANISM: Artificial Sequence
<220> FEATURE:
<223> OTHER INFORMATION: alpha-helix generating peptide

<400> SEQUENCE: 47

Val Glu Glu Ala Val Lys Arg Ala Leu Lys Leu Lys Thr Lys Leu
1               5                   10                  15
```

```
<210> SEQ ID NO 48
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 48

Leu Glu Gln Ala Leu Lys Ile Leu Glu Val Ala Ala Glu Leu
1               5                   10

<210> SEQ ID NO 49
<211> LENGTH: 14
<212> TYPE: PRT
<213> ORGANISM: Artificial Sequence
<220> FEATURE:
<223> OTHER INFORMATION: alpha-helix generating peptide

<400> SEQUENCE: 49

Leu Glu Gln Ala Leu Lys Ile Leu Glu Val Ala Ala Lys Leu
1               5                   10

<210> SEQ ID NO 50
<211> LENGTH: 15
<212> TYPE: PRT
<213> ORGANISM: Artificial Sequence
<220> FEATURE:
<223> OTHER INFORMATION: alpha-helix generating peptide

<400> SEQUENCE: 50

Val Glu Glu Ala Val Lys Arg Ala Met Lys Leu Lys Thr Lys Leu
1               5                   10                  15

<210> SEQ ID NO 51
<211> LENGTH: 93
<212> TYPE: PRT
<213> ORGANISM: Artificial Sequence
<220> FEATURE:
<223> OTHER INFORMATION: dTor_9x31L_sub repeat_num= 3 repeat_len= 31
      protein_len= 93

<400> SEQUENCE: 51

Gly Ile Ser Val Glu Glu Leu Leu Lys Leu Ala Lys Ala Ala Tyr Tyr
1               5                   10                  15

Ser Gly Thr Thr Val Glu Glu Ala Tyr Lys Leu Ala Leu Lys Leu Gly
            20                  25                  30

Ile Ser Val Glu Glu Leu Leu Lys Leu Ala Glu Ala Ala Tyr Tyr Ser
        35                  40                  45

Gly Thr Thr Val Glu Glu Ala Tyr Lys Leu Ala Leu Lys Leu Gly Ile
    50                  55                  60

Ser Val Glu Glu Leu Leu Lys Leu Ala Lys Ala Ala Tyr Tyr Ser Gly
65                  70                  75                  80

Thr Thr Val Glu Glu Ala Tyr Lys Leu Ala Leu Lys Leu
                85                  90

<210> SEQ ID NO 52
<211> LENGTH: 99
<212> TYPE: PRT
<213> ORGANISM: Artificial Sequence
<220> FEATURE:
<223> OTHER INFORMATION: dTor_3x33L_1 repeat_num= 3 repeat_len= 33
      protein_len= 99

<400> SEQUENCE: 52

Gly Lys Ser Pro Thr Glu Ala Leu Leu Lys Leu Ile Ala Glu Ala Lys
```

```
                1               5                   10                  15
            Gly Ile Thr Glu Thr Glu Ala Lys Glu Glu Ala Glu Lys Ala Leu Lys
                                20                  25                  30
            Glu Gly Lys Ser Pro Thr Glu Ala Leu Leu Lys Leu Ile Ala Glu Ala
                        35                  40                  45
            Lys Gly Ile Thr Glu Thr Glu Ala Lys Glu Glu Ala Glu Lys Ala Leu
                    50                  55                  60
            Lys Glu Gly Lys Ser Pro Thr Glu Ala Leu Leu Lys Leu Ile Ala Glu
            65                  70                  75                  80
            Ala Lys Gly Ile Thr Glu Thr Glu Ala Lys Glu Glu Ala Glu Lys Ala
                            85                  90                  95
            Leu Lys Glu

<210> SEQ ID NO 53
<211> LENGTH: 99
<212> TYPE: PRT
<213> ORGANISM: Artificial Sequence
<220> FEATURE:
<223> OTHER INFORMATION: dTor_3x33L_1-1 repeat_num= 3 repeat_len= 33
      protein_len= 99

<400> SEQUENCE: 53

Gly Lys Ser Pro Thr Glu Ala Leu Leu Lys Leu Ile Ala Glu Ala Lys
1               5                   10                  15
Gly Ile Thr Ser Thr Glu Ala Lys Glu Glu Ala Ile Lys Ala Leu Lys
                20                  25                  30
Glu Gly Lys Ser Pro Thr Glu Ala Leu Leu Lys Leu Ile Ala Glu Ala
            35                  40                  45
Lys Gly Ile Thr Glu Leu Glu Ala Lys Val Leu Ala Glu Lys Ala Leu
        50                  55                  60
Lys Glu Gly Lys Ser Pro Thr Glu Ala Leu Leu Lys Leu Ile Ala Glu
65                  70                  75                  80
Ala Lys Gly Ile Thr Glu Thr Glu Ala Lys Leu Glu Ala Glu Lys Ala
                85                  90                  95
Leu Lys Glu

<210> SEQ ID NO 54
<211> LENGTH: 99
<212> TYPE: PRT
<213> ORGANISM: Artificial Sequence
<220> FEATURE:
<223> OTHER INFORMATION: dTor_3x33L_2 repeat_num= 3 repeat_len= 33
      protein_len= 99

<400> SEQUENCE: 54

Gly Lys Ser Pro Thr Glu Val Leu Leu Glu Leu Ile Ala Glu Ala Ser
1               5                   10                  15
Gly Thr Thr Lys Glu Glu Val Lys Glu Lys Phe Leu Lys Glu Leu Ser
                20                  25                  30
Lys Gly Lys Ser Pro Thr Glu Val Leu Leu Glu Leu Ile Ala Glu Ala
            35                  40                  45
Ser Gly Thr Thr Lys Glu Glu Val Lys Glu Lys Phe Leu Lys Glu Leu
        50                  55                  60
Ser Lys Gly Lys Ser Pro Thr Glu Val Leu Leu Glu Leu Ile Ala Glu
65                  70                  75                  80
Ala Ser Gly Thr Thr Lys Glu Glu Val Lys Glu Lys Phe Leu Lys Glu
                85                  90                  95
```

Leu Ser Lys

<210> SEQ ID NO 55
<211> LENGTH: 99
<212> TYPE: PRT
<213> ORGANISM: Artificial Sequence
<220> FEATURE:
<223> OTHER INFORMATION: dTor_3x33L_2-1 repeat_num= 3 repeat_len= 33
      protein_len= 99

<400> SEQUENCE: 55

Gly Lys Ser Pro Thr Glu Val Leu Leu Glu Leu Ile Ala Glu Ala Ser
1               5                   10                  15

Gly Thr Thr Lys Glu Glu Val Lys Arg Lys Phe Leu Lys Glu Leu Ser
            20                  25                  30

Lys Gly Lys Ser Pro Thr Glu Val Leu Leu Glu Leu Ile Ala Glu Ala
        35                  40                  45

Ser Gly Thr Thr Lys Ala Glu Val Lys Arg Glu Phe Leu Trp Glu Leu
50                  55                  60

Ser Leu Gly Lys Ser Pro Thr Glu Val Leu Leu Glu Leu Ile Ala Glu
65                  70                  75                  80

Ala Ser Gly Thr Thr Lys Glu Glu Val Lys Glu Lys Phe Leu Ala Glu
                85                  90                  95

Leu Glu Lys

<210> SEQ ID NO 56
<211> LENGTH: 99
<212> TYPE: PRT
<213> ORGANISM: Artificial Sequence
<220> FEATURE:
<223> OTHER INFORMATION: dTor_3x33L_2-2 repeat_num= 3 repeat_len= 33
      protein_len= 99

<400> SEQUENCE: 56

Gly Lys Ser Pro Thr Glu Val Leu Leu Glu Leu Ile Ala Glu Ala Ser
1               5                   10                  15

Gly Thr Thr Arg Glu Glu Val Lys Glu Lys Phe Leu Lys Glu Leu Arg
            20                  25                  30

Lys Gly Lys Ser Pro Thr Glu Val Leu Leu Glu Leu Ile Ala Glu Ala
        35                  40                  45

Ser Gly Thr Thr Lys Glu Glu Val Lys Glu Lys Phe Leu Lys Glu Leu
50                  55                  60

Ser Phe Gly Lys Ser Pro Thr Glu Val Leu Leu Glu Leu Ile Ala Glu
65                  70                  75                  80

Ala Ser Gly Thr Thr Lys Glu Glu Val Lys Lys Lys Phe Trp Lys Glu
                85                  90                  95

Leu Ser Leu

<210> SEQ ID NO 57
<211> LENGTH: 99
<212> TYPE: PRT
<213> ORGANISM: Artificial Sequence
<220> FEATURE:
<223> OTHER INFORMATION: dTor_3x33L_2-3 repeat_num= 3 repeat_len= 33
      protein_len= 99

<400> SEQUENCE: 57

Gly Lys Ser Pro Thr Glu Val Leu Leu Glu Leu Ile Ala Glu Ala Ser
1               5                   10                  15

Gly Thr Thr Lys Glu Glu Val Lys Glu Lys Phe Leu Lys Glu Leu Ser

```
                    20                  25                  30

Lys Gly Lys Ser Pro Thr Glu Val Leu Leu Glu Leu Ile Ala Glu Ala
            35                  40                  45

Ser Gly Thr Thr Lys Glu Glu Val Lys Glu Lys Phe Leu Lys Glu Leu
        50                  55                  60

Ser Lys Gly Lys Ser Pro Thr Glu Val Leu Leu Glu Leu Ile Ala Glu
 65                  70                  75                  80

Ala Ser Gly Thr Thr Lys Arg Glu Val Lys Arg Trp Phe Leu Phe Glu
                85                  90                  95

Leu Arg Lys

<210> SEQ ID NO 58
<211> LENGTH: 99
<212> TYPE: PRT
<213> ORGANISM: Artificial Sequence
<220> FEATURE:
<223> OTHER INFORMATION: dTor_3x33L_2-4 repeat_num= 3 repeat_len= 33
      protein_len= 99

<400> SEQUENCE: 58

Gly Lys Ser Pro Thr Glu Val Leu Leu Glu Leu Ile Ala Glu Ala Ser
 1               5                  10                  15

Gly Thr Thr Lys Ala Glu Val Lys Leu Lys Phe Leu Phe Glu Leu Ser
            20                  25                  30

Phe Gly Lys Ser Pro Thr Glu Val Leu Leu Glu Leu Ile Ala Glu Ala
            35                  40                  45

Ser Gly Thr Thr Lys Glu Glu Val Lys Glu Lys Phe Leu Lys Glu Leu
        50                  55                  60

Phe Lys Gly Lys Ser Pro Thr Glu Val Leu Leu Glu Leu Ile Ala Glu
 65                  70                  75                  80

Ala Ser Gly Thr Thr Lys Glu Glu Val Lys Glu Lys Phe Leu Lys Glu
                85                  90                  95

Leu Ser Lys

<210> SEQ ID NO 59
<211> LENGTH: 99
<212> TYPE: PRT
<213> ORGANISM: Artificial Sequence
<220> FEATURE:
<223> OTHER INFORMATION: dTor_3x33L_3 repeat_num= 3 repeat_len= 33
      protein_len= 99

<400> SEQUENCE: 59

Gly Tyr Ser Thr Thr Glu Ala Leu Leu Ile Leu Ile Ala Glu Ala Ser
 1               5                  10                  15

Gly Thr Thr Val Glu Gln Gln Lys Gln Arg Phe Lys Glu Leu Val Lys
            20                  25                  30

Lys Gly Tyr Ser Thr Thr Glu Ala Leu Leu Ile Leu Ile Ala Glu Ala
            35                  40                  45

Ser Gly Thr Thr Val Glu Gln Gln Lys Gln Arg Phe Lys Glu Leu Val
        50                  55                  60

Lys Lys Gly Tyr Ser Thr Thr Glu Ala Leu Leu Ile Leu Ile Ala Glu
 65                  70                  75                  80

Ala Ser Gly Thr Thr Val Glu Gln Gln Lys Gln Arg Phe Lys Glu Leu
                85                  90                  95

Val Lys Lys
```

```
<210> SEQ ID NO 60
<211> LENGTH: 198
<212> TYPE: PRT
<213> ORGANISM: Artificial Sequence
<220> FEATURE:
<223> OTHER INFORMATION: dTor_6x33R_1 repeat_num= 6 repeat_len= 33
      protein_len= 198

<400> SEQUENCE: 60
```

Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Arg Tyr Ala Lys Lys
            20                  25                  30

Val Gly Asp Lys Thr Ala Ile Ala Gln Ile Leu Ala Ile Lys Ala Ser
        35                  40                  45

Ala Lys Gly Asp Glu Thr Glu Leu Glu Arg Ala Leu Arg Tyr Ala Lys
    50                  55                  60

Lys Val Gly Asp Lys Thr Ala Ile Ala Gln Ile Leu Ala Ile Lys Ala
65                  70                  75                  80

Ser Ala Lys Gly Asp Glu Thr Glu Leu Glu Arg Ala Leu Arg Tyr Ala
                85                  90                  95

Lys Lys Val Gly Asp Lys Thr Ala Ile Ala Gln Ile Leu Ala Ile Lys
            100                 105                 110

Ala Ser Ala Lys Gly Asp Glu Thr Glu Leu Glu Arg Ala Leu Arg Tyr
        115                 120                 125

Ala Lys Lys Val Gly Asp Lys Thr Ala Ile Ala Gln Ile Leu Ala Ile
    130                 135                 140

Lys Ala Ser Ala Lys Gly Asp Glu Thr Glu Leu Glu Arg Ala Leu Arg
145                 150                 155                 160

Tyr Ala Lys Lys Val Gly Asp Lys Thr Ala Ile Ala Gln Ile Leu Ala
                165                 170                 175

Ile Lys Ala Ser Ala Lys Gly Asp Glu Thr Glu Leu Glu Arg Ala Leu
            180                 185                 190

Arg Tyr Ala Lys Lys Val
        195

```
<210> SEQ ID NO 61
<211> LENGTH: 198
<212> TYPE: PRT
<213> ORGANISM: Artificial Sequence
<220> FEATURE:
<223> OTHER INFORMATION: dTor_6x33R_1-1 repeat_num= 6 repeat_len= 33
      protein_len= 198

<400> SEQUENCE: 61
```

Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Arg Tyr Ala Val Lys
            20                  25                  30

Val Gly Asp Lys Thr Ala Ile Ala Gln Ile Leu Ala Ile Lys Ala Ser
        35                  40                  45

Ala Lys Gly Asp Glu Thr Glu Leu Glu Gln Ala Leu Arg Tyr Ala Lys
    50                  55                  60

Phe Val Gly Asp Lys Thr Ala Ile Ala Gln Ile Leu Ala Ile Lys Ala
65                  70                  75                  80

Ser Ala Lys Gly Asp Glu Leu Glu Leu Thr Arg Ala Leu Ala Tyr Ala
                85                  90                  95

Lys Lys Val Gly Asp Lys Thr Ala Ile Ala Gln Ile Leu Ala Ile Lys

```
                    100                 105                 110
Ala Ser Ala Lys Gly Asp Glu Thr Glu Leu Glu Arg Ala Leu Arg Tyr
        115                 120                 125

Ala Lys Leu Val Gly Asp Lys Thr Ala Ile Ala Gln Ile Leu Ala Ile
    130                 135                 140

Lys Ala Ser Ala Lys Gly Asp Glu Thr Glu Leu Glu Arg Ala Leu Arg
145                 150                 155                 160

Tyr Ala Lys Tyr Val Gly Asp Lys Thr Ala Ile Ala Gln Ile Leu Ala
                165                 170                 175

Ile Lys Ala Ser Ala Lys Gly Asp Glu Pro Glu Leu Glu Tyr Ala Leu
            180                 185                 190

Ala Tyr Ala Lys Lys Val
        195
```

<210> SEQ ID NO 62
<211> LENGTH: 198
<212> TYPE: PRT
<213> ORGANISM: Artificial Sequence
<220> FEATURE:
<223> OTHER INFORMATION: dTor_6x33R_1-2 repeat_num= 6 repeat_len= 33
      protein_len= 198

<400> SEQUENCE: 62

```
Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Arg Tyr Ala Lys Lys
                20                  25                  30

Val Gly Asp Lys Thr Ala Ile Ala Gln Ile Leu Ala Ile Lys Ala Ser
            35                  40                  45

Ala Lys Gly Asp Glu Thr Glu Leu Glu Arg Ala Leu Ile Phe Ala Glu
        50                  55                  60

Ala Val Gly Asp Lys Thr Ala Ile Ala Gln Ile Leu Ala Ile Lys Ala
65                  70                  75                  80

Ser Ala Lys Gly Asp Glu Thr Glu Leu Glu Arg Ala Leu Arg Tyr Ala
                85                  90                  95

Lys Lys Val Asn Asp Lys Thr Ala Ile Ala Gln Ile Leu Ala Ile Lys
            100                 105                 110

Ala Ser Ala Lys Gly Asp Glu Thr Glu Leu Asp Arg Ala Leu Trp Tyr
        115                 120                 125

Ala Lys Lys Val Gly Asp Lys Thr Ala Ile Ala Gln Ile Leu Ala Ile
    130                 135                 140

Lys Ala Ser Ala Lys Gly Asp Glu Thr Glu Leu Glu Arg Ala Leu Arg
145                 150                 155                 160

Tyr Ala Lys Lys Val Gly Asp Lys Thr Ala Ile Ala Gln Ile Leu Ala
                165                 170                 175

Ile Lys Ala Ser Ala Lys Gly Asp Glu Thr Glu Leu Glu Arg Ala Leu
            180                 185                 190

Leu Tyr Ala Lys Lys Val
        195
```

<210> SEQ ID NO 63
<211> LENGTH: 198
<212> TYPE: PRT
<213> ORGANISM: Artificial Sequence
<220> FEATURE:
<223> OTHER INFORMATION: dTor_6x33R_1-3 repeat_num= 6 repeat_len= 33
      protein_len= 198

```
<400> SEQUENCE: 63

Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Arg Tyr Ala Lys Lys
            20                  25                  30

Val Gly Asp Lys Thr Ala Ile Ala Gln Ile Leu Ala Ile Lys Ala Ser
        35                  40                  45

Ala Lys Gly Asp Glu Thr Glu Leu Glu Arg Ala Leu Ala Tyr Ala Arg
50                  55                  60

Leu Val Gly Asp Lys Thr Ala Ile Ala Gln Ile Leu Ala Ile Lys Ala
65                  70                  75                  80

Ser Ala Lys Gly Asp Glu Thr Glu Leu Glu Arg Ala Leu Arg Tyr Ala
                85                  90                  95

Glu Lys Val Gly Asp Lys Thr Ala Ile Ala Gln Ile Leu Ala Ile Lys
            100                 105                 110

Ala Ser Ala Lys Gly Asp Glu Gln Glu Leu Glu Ala Ala Leu Ile Tyr
        115                 120                 125

Ala Lys Lys Val Gly Asp Lys Thr Ala Ile Ala Gln Ile Leu Ala Ile
    130                 135                 140

Lys Ala Ser Ala Lys Gly Asp Glu Thr Glu Leu Glu Arg Ala Leu Arg
145                 150                 155                 160

Tyr Ala Lys Lys Val Gly Asp Lys Thr Ala Ile Ala Gln Ile Leu Ala
                165                 170                 175

Ile Lys Ala Ser Ala Lys Gly Asp Glu Thr Glu Leu Glu Arg Ala Leu
            180                 185                 190

Trp Tyr Ala Lys Lys Val
        195

<210> SEQ ID NO 64
<211> LENGTH: 198
<212> TYPE: PRT
<213> ORGANISM: Artificial Sequence
<220> FEATURE:
<223> OTHER INFORMATION: dTor_6x33R_2 repeat_num= 6 repeat_len= 33
      protein_len= 198

<400> SEQUENCE: 64

Gly Asp Arg Ser Ala Ile Ala Thr Ala Tyr Ile Ala Leu Ala Glu Tyr
1               5                   10                  15

Leu Gly Asp Lys Glu Ala Leu Leu Lys Ala Ile Glu Ile Ala Ile Lys
            20                  25                  30

Leu Gly Asp Arg Ser Ala Ile Ala Glu Ala Tyr Ile Ala Leu Ala Arg
        35                  40                  45

Tyr Leu Gly Asp Lys Glu Ala Leu Leu Lys Ala Ile Glu Ile Ala Ile
50                  55                  60

Lys Leu Gly Asp Arg Ser Ala Ile Ala Thr Ala Tyr Ile Ala Leu Ala
65                  70                  75                  80

Glu Tyr Leu Gly Asp Lys Glu Ala Leu Leu Lys Ala Ile Glu Ile Ala
                85                  90                  95

Ile Lys Leu Gly Asp Arg Ser Ala Ile Ala Glu Ala Tyr Ile Ala Leu
            100                 105                 110

Ala Arg Tyr Leu Gly Asp Lys Glu Ala Leu Leu Lys Ala Ile Glu Ile
        115                 120                 125

Ala Ile Lys Leu Gly Asp Arg Ser Ala Ile Ala Thr Ala Tyr Ile Ala
    130                 135                 140
```

Leu Ala Glu Tyr Leu Gly Asp Lys Glu Ala Leu Leu Lys Ala Ile Glu
145                 150                 155                 160

Ile Ala Ile Lys Leu Gly Asp Arg Ser Ala Ile Ala Glu Ala Tyr Ile
                165                 170                 175

Ala Leu Ala Arg Tyr Leu Gly Asp Lys Glu Ala Leu Leu Lys Ala Ile
            180                 185                 190

Glu Ile Ala Ile Lys Leu
            195

<210> SEQ ID NO 65
<211> LENGTH: 198
<212> TYPE: PRT
<213> ORGANISM: Artificial Sequence
<220> FEATURE:
<223> OTHER INFORMATION: dTor_6x33R_3 repeat_num= 6 repeat_len= 33
      protein_len= 198

<400> SEQUENCE: 65

Gly Asp Lys Ser Ala Leu Ala Gln Ile Leu Ala Ile Tyr Ala Ser Ala
1               5                   10                  15

Tyr Gly Asp Thr Thr Leu Phe Leu Arg Ala Leu Lys Leu Ala Lys Glu
            20                  25                  30

Val Gly Asp Lys Ser Ala Leu Ala Gln Ile Leu Ala Ile Tyr Ala Ser
        35                  40                  45

Ala Tyr Gly Asp Thr Thr Leu Phe Leu Arg Ala Leu Lys Leu Ala Lys
    50                  55                  60

Glu Val Gly Asp Lys Ser Ala Leu Ala Gln Ile Leu Ala Ile Tyr Ala
65                  70                  75                  80

Ser Ala Tyr Gly Asp Thr Thr Leu Phe Leu Arg Ala Leu Lys Leu Ala
                85                  90                  95

Lys Glu Val Gly Asp Lys Ser Ala Leu Ala Gln Ile Leu Ala Ile Tyr
            100                 105                 110

Ala Ser Ala Tyr Gly Asp Thr Thr Leu Phe Leu Arg Ala Leu Lys Leu
        115                 120                 125

Ala Lys Glu Val Gly Asp Lys Ser Ala Leu Ala Gln Ile Leu Ala Ile
    130                 135                 140

Tyr Ala Ser Ala Tyr Gly Asp Thr Thr Leu Phe Leu Arg Ala Leu Lys
145                 150                 155                 160

Leu Ala Lys Glu Val Gly Asp Lys Ser Ala Leu Ala Gln Ile Leu Ala
                165                 170                 175

Ile Tyr Ala Ser Ala Tyr Gly Asp Thr Thr Leu Phe Leu Arg Ala Leu
            180                 185                 190

Lys Leu Ala Lys Glu Val
            195

<210> SEQ ID NO 66
<211> LENGTH: 198
<212> TYPE: PRT
<213> ORGANISM: Artificial Sequence
<220> FEATURE:
<223> OTHER INFORMATION: dTor_6x33R_4 repeat_num= 6 repeat_len= 33
      protein_len= 198

<400> SEQUENCE: 66

Gly Asp Leu Glu Leu Tyr Ile Arg Val Leu Ala Ile Val Ala Glu Ala
1               5                   10                  15

Glu Gly Asp Lys Thr Lys Leu Glu Leu Ala Leu Lys Leu Ala Leu Lys
            20                  25                  30

```
Lys Gly Asp Leu Lys Leu Tyr Ile Glu Val Leu Ala Ile Val Ala Glu
            35                  40                  45

Ala Glu Gly Asp Lys Thr Lys Leu Glu Leu Ala Leu Lys Leu Ala Leu
 50                  55                  60

Lys Lys Gly Asp Leu Glu Leu Tyr Ile Arg Val Leu Ala Ile Val Ala
 65                  70                  75                  80

Lys Ala Glu Gly Asp Lys Thr Lys Leu Glu Leu Ala Leu Lys Leu Ala
                85                  90                  95

Leu Lys Lys Gly Asp Leu Lys Leu Tyr Ile Glu Val Leu Ala Ile Val
                100                 105                 110

Ala Glu Ala Glu Gly Asp Lys Thr Lys Leu Glu Leu Ala Leu Lys Leu
        115                 120                 125

Ala Leu Lys Lys Gly Asp Leu Glu Leu Tyr Ile Arg Val Leu Ala Ile
        130                 135                 140

Val Ala Glu Ala Glu Gly Asp Lys Thr Lys Leu Glu Leu Ala Leu Lys
145                 150                 155                 160

Leu Ala Leu Lys Lys Gly Asp Leu Lys Leu Tyr Ile Glu Val Leu Ala
                165                 170                 175

Ile Val Ala Lys Ala Glu Gly Asp Lys Thr Lys Leu Glu Leu Ala Leu
                180                 185                 190

Lys Leu Ala Leu Lys Lys
                195

<210> SEQ ID NO 67
<211> LENGTH: 210
<212> TYPE: PRT
<213> ORGANISM: Artificial Sequence
<220> FEATURE:
<223> OTHER INFORMATION: dTor_6x35L repeat_num= 6 repeat_len= 35
      protein_len= 210

<400> SEQUENCE: 67

Val Ser Leu Glu Gln Ala Leu Lys Ile Leu Lys Val Ala Ala Glu Leu
 1               5                  10                  15

Gly Thr Thr Val Glu Glu Ala Val Lys Arg Ala Leu Lys Leu Lys Thr
                20                  25                  30

Lys Leu Gly Val Ser Leu Glu Gln Ala Leu Lys Ile Leu Glu Val Ala
            35                  40                  45

Ala Glu Leu Gly Thr Thr Val Glu Glu Ala Val Lys Arg Ala Leu Lys
 50                  55                  60

Leu Lys Thr Lys Leu Gly Val Ser Leu Glu Gln Ala Leu Lys Ile Leu
 65                  70                  75                  80

Glu Val Ala Ala Lys Leu Gly Thr Thr Val Glu Glu Ala Val Lys Arg
                85                  90                  95

Ala Leu Lys Leu Lys Thr Lys Leu Gly Val Ser Leu Glu Gln Ala Leu
                100                 105                 110

Lys Ile Leu Lys Val Ala Ala Glu Leu Gly Thr Thr Val Glu Glu Ala
        115                 120                 125

Val Lys Arg Ala Leu Lys Leu Lys Thr Lys Leu Gly Val Ser Leu Glu
        130                 135                 140

Gln Ala Leu Lys Ile Leu Glu Val Ala Ala Glu Leu Gly Thr Thr Val
145                 150                 155                 160

Glu Glu Ala Val Lys Arg Ala Leu Lys Leu Lys Thr Lys Leu Gly Val
                165                 170                 175

Ser Leu Glu Gln Ala Leu Lys Ile Leu Glu Val Ala Ala Lys Leu Gly
                180                 185                 190
```

Thr Thr Val Glu Glu Ala Val Lys Arg Ala Leu Lys Leu Lys Thr Lys
        195                 200                 205

Leu Gly
    210

<210> SEQ ID NO 68
<211> LENGTH: 210
<212> TYPE: PRT
<213> ORGANISM: Artificial Sequence
<220> FEATURE:
<223> OTHER INFORMATION: dTor_6x35L(SeMet) repeat_num= 6 repeat_len= 35
      protein_len= 210

<400> SEQUENCE: 68

Val Ser Leu Glu Gln Ala Leu Lys Ile Leu Lys Val Ala Ala Glu Leu
1               5                   10                  15

Gly Thr Thr Val Glu Glu Ala Val Lys Arg Ala Leu Lys Leu Lys Thr
                20                  25                  30

Lys Leu Gly Val Ser Leu Glu Gln Ala Leu Lys Ile Leu Glu Val Ala
            35                  40                  45

Ala Glu Leu Gly Thr Thr Val Glu Glu Ala Val Lys Arg Ala Leu Lys
        50                  55                  60

Leu Lys Thr Lys Leu Gly Val Ser Leu Glu Gln Ala Leu Lys Ile Leu
65                  70                  75                  80

Glu Val Ala Ala Lys Leu Gly Thr Thr Val Glu Glu Ala Val Lys Arg
                85                  90                  95

Ala Leu Lys Leu Lys Thr Lys Leu Gly Val Ser Leu Glu Gln Ala Leu
                100                 105                 110

Lys Ile Leu Lys Val Ala Ala Glu Leu Gly Thr Thr Val Glu Glu Ala
            115                 120                 125

Val Lys Arg Ala Leu Lys Leu Lys Thr Lys Leu Gly Val Ser Leu Glu
        130                 135                 140

Gln Ala Leu Lys Ile Leu Glu Val Ala Ala Glu Leu Gly Thr Thr Val
145                 150                 155                 160

Glu Glu Ala Val Lys Arg Ala Met Lys Leu Lys Thr Lys Leu Gly Val
                165                 170                 175

Ser Leu Glu Gln Ala Leu Lys Ile Leu Glu Val Ala Ala Lys Leu Gly
            180                 185                 190

Thr Thr Val Glu Glu Ala Val Lys Arg Ala Leu Lys Leu Lys Thr Lys
        195                 200                 205

Leu Gly
    210

<210> SEQ ID NO 69
<211> LENGTH: 279
<212> TYPE: PRT
<213> ORGANISM: Artificial Sequence
<220> FEATURE:
<223> OTHER INFORMATION: dTor_9x31L repeat_num= 9 repeat_len= 31
      protein_len= 279

<400> SEQUENCE: 69

Gly Ile Ser Val Glu Glu Leu Leu Lys Leu Ala Lys Ala Ala Tyr Tyr
1               5                   10                  15

Ser Gly Thr Thr Val Glu Glu Ala Tyr Lys Leu Ala Leu Lys Leu Gly
                20                  25                  30

Ile Ser Val Glu Glu Leu Leu Lys Leu Ala Glu Ala Ala Tyr Tyr Ser
            35                  40                  45

Gly Thr Thr Val Glu Glu Ala Tyr Lys Leu Ala Leu Lys Leu Gly Ile
            50                  55                  60

Ser Val Glu Glu Leu Leu Lys Leu Ala Lys Ala Ala Tyr Tyr Ser Gly
 65                  70                  75                  80

Thr Thr Val Glu Glu Ala Tyr Lys Leu Ala Leu Lys Leu Gly Ile Ser
                85                  90                  95

Val Glu Glu Leu Leu Lys Leu Ala Lys Ala Ala Tyr Tyr Ser Gly Thr
            100                 105                 110

Thr Val Glu Glu Ala Tyr Lys Leu Ala Leu Lys Leu Gly Ile Ser Val
        115                 120                 125

Glu Glu Leu Leu Lys Leu Ala Glu Ala Ala Tyr Tyr Ser Gly Thr Thr
    130                 135                 140

Val Glu Glu Ala Tyr Lys Leu Ala Leu Lys Leu Gly Ile Ser Val Glu
145                 150                 155                 160

Glu Leu Leu Lys Leu Ala Lys Ala Ala Tyr Tyr Ser Gly Thr Thr Val
                165                 170                 175

Glu Glu Ala Tyr Lys Leu Ala Leu Lys Leu Gly Ile Ser Val Glu Glu
            180                 185                 190

Leu Leu Lys Leu Ala Lys Ala Ala Tyr Tyr Ser Gly Thr Thr Val Glu
        195                 200                 205

Glu Ala Tyr Lys Leu Ala Leu Lys Leu Gly Ile Ser Val Glu Glu Leu
    210                 215                 220

Leu Lys Leu Ala Glu Ala Ala Tyr Tyr Ser Gly Thr Thr Val Glu Glu
225                 230                 235                 240

Ala Tyr Lys Leu Ala Leu Lys Leu Gly Ile Ser Val Glu Glu Leu Leu
                245                 250                 255

Lys Leu Ala Lys Ala Ala Tyr Tyr Ser Gly Thr Thr Val Glu Glu Ala
            260                 265                 270

Tyr Lys Leu Ala Leu Lys Leu
        275

<210> SEQ ID NO 70
<211> LENGTH: 372
<212> TYPE: PRT
<213> ORGANISM: Artificial Sequence
<220> FEATURE:
<223> OTHER INFORMATION: dTor_12x31L repeat_num= 12 repeat_len= 31
      protein_len= 372

<400> SEQUENCE: 70

Gly Ile Ser Val Glu Glu Leu Leu Lys Leu Ala Lys Ala Ala Tyr Tyr
 1               5                  10                  15

Ser Gly Thr Thr Val Glu Glu Ala Tyr Lys Leu Ala Leu Lys Leu Gly
            20                  25                  30

Ile Ser Val Glu Glu Leu Leu Lys Leu Ala Glu Ala Ala Tyr Tyr Ser
        35                  40                  45

Gly Thr Thr Val Glu Glu Ala Tyr Lys Leu Ala Leu Lys Leu Gly Ile
    50                  55                  60

Ser Val Glu Glu Leu Leu Lys Leu Ala Lys Ala Ala Tyr Tyr Ser Gly
 65                  70                  75                  80

Thr Thr Val Glu Glu Ala Tyr Lys Leu Ala Leu Lys Leu Gly Ile Ser
                85                  90                  95

Val Glu Glu Leu Leu Lys Leu Ala Lys Ala Ala Tyr Tyr Ser Gly Thr
            100                 105                 110

Thr Val Glu Glu Ala Tyr Lys Leu Ala Leu Lys Leu Gly Ile Ser Val

```
                  115                 120                 125
Glu Glu Leu Leu Lys Leu Ala Glu Ala Ala Tyr Tyr Ser Gly Thr Thr
            130                 135                 140

Val Glu Glu Ala Tyr Lys Leu Ala Leu Lys Leu Gly Ile Ser Val Glu
145                 150                 155                 160

Glu Leu Leu Lys Leu Ala Lys Ala Ala Tyr Tyr Ser Gly Thr Thr Val
                165                 170                 175

Glu Glu Ala Tyr Lys Leu Ala Leu Lys Leu Gly Ile Ser Val Glu Glu
            180                 185                 190

Leu Leu Lys Leu Ala Lys Ala Ala Tyr Tyr Ser Gly Thr Thr Val Glu
        195                 200                 205

Glu Ala Tyr Lys Leu Ala Leu Lys Leu Gly Ile Ser Val Glu Glu Leu
    210                 215                 220

Leu Lys Leu Ala Lys Ala Ala Tyr Tyr Ser Gly Thr Thr Val Glu Glu
225                 230                 235                 240

Ala Tyr Lys Leu Ala Leu Lys Leu Gly Ile Ser Val Glu Glu Leu Leu
                245                 250                 255

Lys Leu Ala Lys Ala Ala Tyr Tyr Ser Gly Thr Thr Val Glu Glu Ala
            260                 265                 270

Tyr Lys Leu Ala Leu Lys Leu Gly Ile Ser Val Glu Glu Leu Leu Lys
        275                 280                 285

Leu Ala Lys Ala Ala Tyr Tyr Ser Gly Thr Thr Val Glu Glu Ala Tyr
    290                 295                 300

Lys Leu Ala Leu Lys Leu Gly Ile Ser Val Glu Glu Leu Leu Lys Leu
305                 310                 315                 320

Ala Glu Ala Ala Tyr Tyr Ser Gly Thr Thr Val Glu Glu Ala Tyr Lys
                325                 330                 335

Leu Ala Leu Lys Leu Gly Ile Ser Val Glu Glu Leu Leu Lys Leu Ala
            340                 345                 350

Lys Ala Ala Tyr Tyr Ser Gly Thr Thr Val Glu Glu Ala Tyr Lys Leu
        355                 360                 365

Ala Leu Lys Leu
    370

<210> SEQ ID NO 71
<211> LENGTH: 477
<212> TYPE: PRT
<213> ORGANISM: Artificial Sequence
<220> FEATURE:
<223> OTHER INFORMATION: design_12x_insert_single

<400> SEQUENCE: 71

Gly Ile Ser Val Glu Glu Leu Leu Lys Leu Ala Lys Ala Ala Tyr Tyr
1               5                  10                  15

Ser Gly Thr Thr Val Glu Glu Ala Tyr Lys Leu Ala Leu Lys Leu Gly
            20                  25                  30

Ile Ser Val Glu Glu Leu Leu Lys Leu Ala Glu Ala Ala Tyr Tyr Ser
        35                  40                  45

Gly Thr Thr Val Glu Glu Ala Tyr Lys Leu Ala Leu Lys Leu Gly Ile
    50                  55                  60

Ser Val Glu Glu Leu Leu Lys Leu Ala Lys Ala Ala Tyr Tyr Ser Gly
65                  70                  75                  80

Thr Thr Val Glu Glu Ala Tyr Lys Leu Ala Leu Lys Leu Gly Ile Ser
                85                  90                  95

Val Glu Glu Leu Leu Lys Leu Ala Lys Ala Ala Tyr Tyr Ser Gly Thr
```

```
                    100                 105                 110
        Thr Val Glu Glu Ala Tyr Lys Leu Ala Leu Lys Leu Gly Ile Ser Val
                    115                 120                 125
        Glu Glu Leu Leu Lys Leu Ala Glu Ala Ala Tyr Tyr Ser Gly Thr Thr
                    130                 135                 140
        Val Glu Glu Ala Tyr Lys Leu Ala Leu Lys Leu Gly Ile Ser Val Glu
        145                 150                 155                 160
        Glu Leu Leu Lys Leu Ala Lys Ala Ala Tyr Tyr Ser Gly Ser Gly Gly
                            165                 170                 175
        Ser Glu Trp Tyr Tyr Gly Asn Val Thr Arg His Gln Ala Glu Cys Ala
                        180                 185                 190
        Leu Asn Glu Arg Gly Val Glu Gly Asp Phe Leu Ile Arg Asp Ser Glu
                        195                 200                 205
        Ser Ser Pro Ser Asp Phe Ser Val Ser Leu Lys Ala Ser Gly Lys Asn
                        210                 215                 220
        Lys His Phe Lys Val Gln Leu Val Asp Asn Val Tyr Cys Ile Gly Gln
        225                 230                 235                 240
        Arg Arg Phe His Thr Met Asp Glu Leu Val Glu His Tyr Lys Lys Ala
                        245                 250                 255
        Pro Ile Phe Thr Ser Glu His Gly Glu Lys Leu Tyr Leu Val Arg Ala
                        260                 265                 270
        Leu Gln Gly Ser Gly Gly Thr Val Glu Glu Ala Tyr Lys Leu Ala Leu
                        275                 280                 285
        Lys Leu Gly Ile Ser Val Glu Glu Leu Leu Lys Leu Ala Lys Ala Ala
                        290                 295                 300
        Tyr Tyr Ser Gly Thr Thr Val Glu Glu Ala Tyr Lys Leu Ala Leu Lys
        305                 310                 315                 320
        Leu Gly Ile Ser Val Glu Glu Leu Leu Lys Leu Ala Glu Ala Ala Tyr
                        325                 330                 335
        Tyr Ser Gly Thr Thr Val Glu Glu Ala Tyr Lys Leu Ala Leu Lys Leu
                        340                 345                 350
        Gly Ile Ser Val Glu Glu Leu Leu Lys Leu Ala Lys Ala Ala Tyr Tyr
                        355                 360                 365
        Ser Gly Thr Thr Val Glu Glu Ala Tyr Lys Leu Ala Leu Lys Leu Gly
                        370                 375                 380
        Ile Ser Val Glu Glu Leu Leu Lys Leu Ala Lys Ala Ala Tyr Tyr Ser
        385                 390                 395                 400
        Gly Thr Thr Val Glu Glu Ala Tyr Lys Leu Ala Leu Lys Leu Gly Ile
                        405                 410                 415
        Ser Val Glu Glu Leu Leu Lys Leu Ala Glu Ala Ala Tyr Tyr Ser Gly
                        420                 425                 430
        Thr Thr Val Glu Glu Ala Tyr Lys Leu Ala Leu Lys Leu Gly Ile Ser
                        435                 440                 445
        Val Glu Glu Leu Leu Lys Leu Ala Lys Ala Ala Tyr Tyr Ser Gly Thr
                        450                 455                 460
        Thr Val Glu Glu Ala Tyr Lys Leu Ala Leu Lys Leu Gly
        465                 470                 475

<210> SEQ ID NO 72
<211> LENGTH: 581
<212> TYPE: PRT
<213> ORGANISM: Artificial Sequence
<220> FEATURE:
<223> OTHER INFORMATION: design_12x_insert_double
```

<400> SEQUENCE: 72

```
Gly Ile Ser Val Glu Glu Leu Leu Lys Leu Ala Lys Ala Ala Tyr Tyr
1               5                   10                  15
Ser Gly Thr Thr Val Glu Glu Ala Tyr Lys Leu Ala Leu Lys Leu Gly
            20                  25                  30
Ile Ser Val Glu Glu Leu Leu Lys Leu Ala Glu Ala Ala Tyr Tyr Ser
        35                  40                  45
Gly Thr Thr Val Glu Glu Ala Tyr Lys Leu Ala Leu Lys Leu Gly Ile
    50                  55                  60
Ser Val Glu Glu Leu Leu Lys Leu Ala Lys Ala Ala Tyr Tyr Ser Gly
65                  70                  75                  80
Thr Thr Val Glu Glu Ala Tyr Lys Leu Ala Leu Lys Leu Gly Ile Ser
                85                  90                  95
Val Glu Glu Leu Leu Lys Leu Ala Lys Ala Ala Tyr Tyr Ser Gly Ser
            100                 105                 110
Gly Gly Ser Glu Trp Tyr Tyr Gly Asn Val Thr Arg His Gln Ala Glu
        115                 120                 125
Cys Ala Leu Asn Glu Arg Gly Val Glu Gly Asp Phe Leu Ile Arg Asp
    130                 135                 140
Ser Glu Ser Ser Pro Ser Asp Phe Ser Val Ser Leu Lys Ala Ser Gly
145                 150                 155                 160
Lys Asn Lys His Phe Lys Val Gln Leu Val Asp Asn Val Tyr Cys Ile
                165                 170                 175
Gly Gln Arg Arg Phe His Thr Met Asp Glu Leu Val Glu His Tyr Lys
            180                 185                 190
Lys Ala Pro Ile Phe Thr Ser Glu His Gly Glu Lys Leu Tyr Leu Val
        195                 200                 205
Arg Ala Leu Gln Gly Ser Gly Thr Val Glu Glu Ala Tyr Lys Leu Ala
    210                 215                 220
Leu Lys Leu Gly Ile Ser Val Glu Glu Leu Leu Lys Leu Ala Glu Ala
225                 230                 235                 240
Ala Ala Tyr Tyr Ser Gly Thr Thr Val Glu Glu Ala Tyr Lys Leu Ala
                245                 250                 255
Leu Lys Leu Gly Ile Ser Val Glu Glu Leu Leu Lys Leu Ala Lys Ala
            260                 265                 270
Ala Tyr Tyr Ser Gly Thr Thr Val Glu Glu Ala Tyr Lys Leu Ala Leu
        275                 280                 285
Lys Leu Gly Ile Ser Val Glu Glu Leu Leu Lys Leu Ala Lys Ala Ala
    290                 295                 300
Tyr Tyr Ser Gly Thr Thr Val Glu Glu Ala Tyr Lys Leu Ala Leu Lys
305                 310                 315                 320
Leu Gly Ile Ser Val Glu Glu Leu Leu Lys Leu Ala Glu Ala Ala Tyr
                325                 330                 335
Tyr Ser Gly Thr Thr Val Glu Glu Ala Tyr Lys Leu Ala Leu Lys Leu
            340                 345                 350
Gly Ile Ser Val Glu Glu Leu Leu Lys Leu Ala Lys Ala Ala Tyr Tyr
        355                 360                 365
Ser Gly Thr Thr Val Glu Glu Ala Tyr Lys Leu Ala Leu Lys Leu Gly
    370                 375                 380
Ile Ser Val Glu Glu Leu Leu Lys Leu Ala Lys Ala Ala Tyr Tyr Ser
385                 390                 395                 400
Gly Ser Gly Gly Ser Glu Trp Tyr Tyr Gly Asn Val Thr Arg His Gln
                405                 410                 415
```

```
Ala Glu Cys Ala Leu Asn Glu Arg Gly Val Glu Gly Asp Phe Leu Ile
            420                 425                 430

Arg Asp Ser Glu Ser Ser Pro Ser Asp Phe Ser Val Ser Leu Lys Ala
            435                 440                 445

Ser Gly Lys Asn Lys His Phe Lys Val Gln Leu Val Asp Asn Val Tyr
450                 455                 460

Cys Ile Gly Gln Arg Arg Phe His Thr Met Asp Glu Leu Val Glu His
465                 470                 475                 480

Tyr Lys Lys Ala Pro Ile Phe Thr Ser Glu His Gly Glu Lys Leu Tyr
                485                 490                 495

Leu Val Arg Ala Leu Gln Gly Ser Gly Gly Thr Val Glu Glu Ala Tyr
            500                 505                 510

Lys Leu Ala Leu Lys Leu Gly Ile Ser Val Glu Glu Leu Leu Lys Leu
            515                 520                 525

Ala Glu Ala Ala Tyr Tyr Ser Gly Thr Thr Val Glu Glu Ala Tyr Lys
            530                 535                 540

Leu Ala Leu Lys Leu Gly Ile Ser Val Glu Glu Leu Leu Lys Leu Ala
545                 550                 555                 560

Lys Ala Ala Tyr Tyr Ser Gly Thr Thr Val Glu Glu Ala Tyr Lys Leu
                565                 570                 575

Ala Leu Lys Leu Gly
            580

<210> SEQ ID NO 73
<211> LENGTH: 31
<212> TYPE: PRT
<213> ORGANISM: Artificial Sequence
<220> FEATURE:
<223> OTHER INFORMATION: alpha helical structure joined by linkers

<400> SEQUENCE: 73

Gly Ile Ser Val Glu Glu Leu Leu Lys Leu Ala Lys Ala Ala Tyr Tyr
1               5                   10                  15

Ser Gly Thr Thr Val Glu Glu Ala Tyr Lys Leu Ala Leu Lys Leu
            20                  25                  30

<210> SEQ ID NO 74
<211> LENGTH: 31
<212> TYPE: PRT
<213> ORGANISM: Artificial Sequence
<220> FEATURE:
<223> OTHER INFORMATION: alpha helical structure joined by linkers

<400> SEQUENCE: 74

Gly Ile Ser Val Glu Glu Leu Leu Lys Leu Ala Glu Ala Ala Tyr Tyr
1               5                   10                  15

Ser Gly Thr Thr Val Glu Glu Ala Tyr Lys Leu Ala Leu Lys Leu
            20                  25                  30

<210> SEQ ID NO 75
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 75

Gly Lys Ser Pro Thr Glu Ala Leu Leu Lys Leu Ile Ala Glu Ala Lys
1               5                   10                  15
```

Gly Ile Thr Glu Thr Glu Ala Lys Glu Ala Glu Lys Ala Leu Lys
            20                  25                  30

Glu

<210> SEQ ID NO 76
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 76

Gly Lys Ser Pro Thr Glu Ala Leu Leu Lys Leu Ile Ala Glu Ala Lys
1               5                   10                  15

Gly Ile Thr Ser Thr Glu Ala Lys Glu Glu Ala Ile Lys Ala Leu Lys
            20                  25                  30

Glu

<210> SEQ ID NO 77
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 77

Gly Lys Ser Pro Thr Glu Ala Leu Leu Lys Leu Ile Ala Glu Ala Lys
1               5                   10                  15

Gly Ile Thr Glu Leu Glu Ala Lys Val Leu Ala Glu Lys Ala Leu Lys
            20                  25                  30

Glu

<210> SEQ ID NO 78
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 78

Gly Lys Ser Pro Thr Glu Ala Leu Leu Lys Leu Ile Ala Glu Ala Lys
1               5                   10                  15

Gly Ile Thr Glu Thr Glu Ala Lys Leu Glu Ala Glu Lys Ala Leu Lys
            20                  25                  30

Glu

<210> SEQ ID NO 79
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 79

Gly Lys Ser Pro Thr Glu Val Leu Leu Glu Leu Ile Ala Glu Ala Ser
1               5                   10                  15

Gly Thr Thr Lys Glu Glu Val Lys Glu Lys Phe Leu Lys Glu Leu Ser
            20                  25                  30

Lys

<210> SEQ ID NO 80

<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 80

Gly Lys Ser Pro Thr Glu Val Leu Leu Glu Leu Ile Ala Glu Ala Ser
1               5                   10                  15
Gly Thr Thr Lys Glu Glu Val Lys Arg Lys Phe Leu Lys Glu Leu Ser
            20                  25                  30
Lys

<210> SEQ ID NO 81
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 81

Gly Lys Ser Pro Thr Glu Val Leu Leu Glu Leu Ile Ala Glu Ala Ser
1               5                   10                  15
Gly Thr Thr Lys Ala Glu Val Lys Arg Glu Phe Leu Trp Glu Leu Ser
            20                  25                  30
Leu

<210> SEQ ID NO 82
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 82

Gly Lys Ser Pro Thr Glu Val Leu Leu Glu Leu Ile Ala Glu Ala Ser
1               5                   10                  15
Gly Thr Thr Lys Glu Glu Val Lys Glu Lys Phe Leu Ala Glu Leu Glu
            20                  25                  30
Lys

<210> SEQ ID NO 83
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 83

Gly Lys Ser Pro Thr Glu Val Leu Leu Glu Leu Ile Ala Glu Ala Ser
1               5                   10                  15
Gly Thr Thr Arg Glu Glu Val Lys Glu Lys Phe Leu Lys Glu Leu Arg
            20                  25                  30
Lys

<210> SEQ ID NO 84
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 84

Gly Lys Ser Pro Thr Glu Val Leu Leu Glu Leu Ile Ala Glu Ala Ser
1               5                   10                  15

Gly Thr Thr Lys Glu Glu Val Lys Glu Lys Phe Leu Lys Glu Leu Ser
                20                  25                  30

Phe

<210> SEQ ID NO 85
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 85

Gly Lys Ser Pro Thr Glu Val Leu Leu Glu Leu Ile Ala Glu Ala Ser
1               5                   10                  15

Gly Thr Thr Lys Glu Glu Val Lys Lys Lys Phe Trp Lys Glu Leu Ser
                20                  25                  30

Leu

<210> SEQ ID NO 86
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 86

Gly Lys Ser Pro Thr Glu Val Leu Leu Glu Leu Ile Ala Glu Ala Ser
1               5                   10                  15

Gly Thr Thr Lys Arg Glu Val Lys Arg Trp Phe Leu Phe Glu Leu Arg
                20                  25                  30

Lys

<210> SEQ ID NO 87
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 87

Gly Lys Ser Pro Thr Glu Val Leu Leu Glu Leu Ile Ala Glu Ala Ser
1               5                   10                  15

Gly Thr Thr Lys Ala Glu Val Lys Leu Lys Phe Leu Phe Glu Leu Ser
                20                  25                  30

Phe

<210> SEQ ID NO 88
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 88

Gly Lys Ser Pro Thr Glu Val Leu Leu Glu Leu Ile Ala Glu Ala Ser
1               5                   10                  15

Gly Thr Thr Lys Glu Glu Val Lys Glu Lys Phe Leu Lys Glu Leu Phe
                20                  25                  30

Lys

<210> SEQ ID NO 89
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 89

```
Gly Tyr Ser Thr Thr Glu Ala Leu Leu Ile Leu Ile Ala Glu Ala Ser
1               5                   10                  15

Gly Thr Thr Val Glu Gln Gln Lys Gln Arg Phe Lys Glu Leu Val Lys
            20                  25                  30

Lys
```

<210> SEQ ID NO 90
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 90

```
Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Arg Tyr Ala Lys Lys
            20                  25                  30

Val
```

<210> SEQ ID NO 91
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 91

```
Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Arg Tyr Ala Val Lys
            20                  25                  30

Val
```

<210> SEQ ID NO 92
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 92

```
Gly Asp Lys Thr Ala Ile Ala Gln Ile Leu Ala Ile Lys Ala Ser Ala
1               5                   10                  15

Lys Gly Asp Glu Thr Glu Leu Glu Gln Ala Leu Arg Tyr Ala Lys Phe
            20                  25                  30

Val
```

<210> SEQ ID NO 93
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 93

Gly Asp Lys Thr Ala Ile Ala Gln Ile Leu Ala Ile Lys Ala Ser Ala
1               5                   10                  15

Lys Gly Asp Glu Leu Glu Leu Thr Arg Ala Leu Ala Tyr Ala Lys Lys
            20                  25                  30

Val

<210> SEQ ID NO 94
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 94

Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Arg Tyr Ala Lys Leu
            20                  25                  30

Val

<210> SEQ ID NO 95
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 95

Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Arg Tyr Ala Lys Tyr
            20                  25                  30

Val

<210> SEQ ID NO 96
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 96

Gly Asp Lys Thr Ala Ile Ala Gln Ile Leu Ala Ile Lys Ala Ser Ala
1               5                   10                  15

Lys Gly Asp Glu Pro Glu Leu Glu Tyr Ala Leu Ala Tyr Ala Lys Lys
            20                  25                  30

Val

<210> SEQ ID NO 97
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 97

Gly Asp Lys Thr Ala Ile Ala Gln Ile Leu Ala Ile Lys Ala Ser Ala
1               5                   10                  15

```
Lys Gly Asp Glu Thr Glu Leu Glu Arg Ala Leu Ile Phe Ala Glu Ala
            20                  25                  30

Val
```

<210> SEQ ID NO 98
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 98

```
Asn Asp Lys Thr Ala Ile Ala Gln Ile Leu Ala Ile Lys Ala Ser Ala
1               5                   10                  15

Lys Gly Asp Glu Thr Glu Leu Asp Arg Ala Leu Trp Tyr Ala Lys Lys
            20                  25                  30

Val
```

<210> SEQ ID NO 99
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 99

```
Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Leu Tyr Ala Lys Lys
            20                  25                  30

Val
```

<210> SEQ ID NO 100
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 100

```
Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Ala Tyr Ala Arg Leu
            20                  25                  30

Val
```

<210> SEQ ID NO 101
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 101

```
Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Arg Tyr Ala Glu Lys
            20                  25                  30

Val
```

```
<210> SEQ ID NO 102
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 102

Gly Asp Lys Thr Ala Ile Ala Gln Ile Leu Ala Ile Lys Ala Ser Ala
1               5                   10                  15

Lys Gly Asp Glu Gln Glu Leu Glu Ala Ala Leu Ile Tyr Ala Lys Lys
            20                  25                  30

Val

<210> SEQ ID NO 103
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 103

Gly Asp Lys Thr Ala Ile Ala Gln Ile Leu Ala Ile Lys Ala Ser Ala
1               5                   10                  15

Lys Gly Asp Glu Thr Glu Leu Glu Arg Ala Leu Trp Tyr Ala Lys Lys
            20                  25                  30

Val

<210> SEQ ID NO 104
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 104

Gly Asp Arg Ser Ala Ile Ala Thr Ala Tyr Ile Ala Leu Ala Glu Tyr
1               5                   10                  15

Leu Gly Asp Lys Glu Ala Leu Leu Lys Ala Ile Glu Ile Ala Ile Lys
            20                  25                  30

Leu

<210> SEQ ID NO 105
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 105

Gly Asp Arg Ser Ala Ile Ala Glu Ala Tyr Ile Ala Leu Ala Arg Tyr
1               5                   10                  15

Leu Gly Asp Lys Glu Ala Leu Leu Lys Ala Ile Glu Ile Ala Ile Lys
            20                  25                  30

Leu

<210> SEQ ID NO 106
<211> LENGTH: 33
<212> TYPE: PRT
<213> ORGANISM: Artificial Sequence
<220> FEATURE:
<223> OTHER INFORMATION: alpha helical structure joined by linkers
```

```
<400> SEQUENCE: 106

Gly Asp Lys Ser Ala Leu Ala Gln Ile Leu Ala Ile Tyr Ala Ser Ala
1               5                   10                  15

Tyr Gly Asp Thr Thr Leu Phe Leu Arg Ala Leu Lys Leu Ala Lys Glu
                20                  25                  30

Val

<210> SEQ ID NO 107
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 107

Gly Asp Leu Glu Leu Tyr Ile Arg Val Leu Ala Ile Val Ala Glu Ala
1               5                   10                  15

Glu Gly Asp Lys Thr Lys Leu Glu Leu Ala Leu Lys Leu Ala Leu Lys
                20                  25                  30

Lys

<210> SEQ ID NO 108
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 108

Gly Asp Leu Lys Leu Tyr Ile Glu Val Leu Ala Ile Val Ala Glu Ala
1               5                   10                  15

Glu Gly Asp Lys Thr Lys Leu Glu Leu Ala Leu Lys Leu Ala Leu Lys
                20                  25                  30

Lys

<210> SEQ ID NO 109
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 109

Gly Asp Leu Glu Leu Tyr Ile Arg Val Leu Ala Ile Val Ala Lys Ala
1               5                   10                  15

Glu Gly Asp Lys Thr Lys Leu Glu Leu Ala Leu Lys Leu Ala Leu Lys
                20                  25                  30

Lys

<210> SEQ ID NO 110
<211> LENGTH: 33
<212> TYPE: PRT
<213> ORGANISM: Artificial Sequence
<220> FEATURE:
<223> OTHER INFORMATION: alpha helical structure joined by linkers

<400> SEQUENCE: 110

Gly Asp Leu Lys Leu Tyr Ile Glu Val Leu Ala Ile Val Ala Lys Ala
1               5                   10                  15

Glu Gly Asp Lys Thr Lys Leu Glu Leu Ala Leu Lys Leu Ala Leu Lys
                20                  25                  30
```

Lys

```
<210> SEQ ID NO 111
<211> LENGTH: 35
<212> TYPE: PRT
<213> ORGANISM: Artificial Sequence
<220> FEATURE:
<223> OTHER INFORMATION: alpha helical structure joined by linkers

<400> SEQUENCE: 111

Gly Val Ser Leu Glu Gln Ala Leu Lys Ile Leu Lys Val Ala Ala Glu
1               5                   10                  15

Leu Gly Thr Thr Val Glu Glu Ala Val Lys Arg Ala Leu Lys Leu Lys
            20                  25                  30

Thr Lys Leu
        35

<210> SEQ ID NO 112
<211> LENGTH: 35
<212> TYPE: PRT
<213> ORGANISM: Artificial Sequence
<220> FEATURE:
<223> OTHER INFORMATION: alpha helical structure joined by linkers

<400> SEQUENCE: 112

Gly Val Ser Leu Glu Gln Ala Leu Lys Ile Leu Glu Val Ala Ala Glu
1               5                   10                  15

Leu Gly Thr Thr Val Glu Glu Ala Val Lys Arg Ala Leu Lys Leu Lys
            20                  25                  30

Thr Lys Leu
        35

<210> SEQ ID NO 113
<211> LENGTH: 35
<212> TYPE: PRT
<213> ORGANISM: Artificial Sequence
<220> FEATURE:
<223> OTHER INFORMATION: alpha helical structure joined by linkers

<400> SEQUENCE: 113

Gly Val Ser Leu Glu Gln Ala Leu Lys Ile Leu Glu Val Ala Ala Lys
1               5                   10                  15

Leu Gly Thr Thr Val Glu Glu Ala Val Lys Arg Ala Leu Lys Leu Lys
            20                  25                  30

Thr Lys Leu
        35

<210> SEQ ID NO 114
<211> LENGTH: 35
<212> TYPE: PRT
<213> ORGANISM: Artificial Sequence
<220> FEATURE:
<223> OTHER INFORMATION: alpha helical structure joined by linkers

<400> SEQUENCE: 114

Gly Val Ser Leu Glu Gln Ala Leu Lys Ile Leu Glu Val Ala Ala Glu
1               5                   10                  15

Leu Gly Thr Thr Val Glu Glu Ala Val Lys Arg Ala Met Lys Leu Lys
            20                  25                  30

Thr Lys Leu
        35
```

```
<210> SEQ ID NO 115
<211> LENGTH: 18
<212> TYPE: PRT
<213> ORGANISM: Artificial Sequence
<220> FEATURE:
<223> OTHER INFORMATION: peptide adjuvant from HMGB1

<400> SEQUENCE: 115

Asp Pro Asn Ala Pro Lys Arg Pro Pro Ser Ala Phe Phe Leu Phe Cys
1               5                   10                  15

Ser Glu

<210> SEQ ID NO 116
<211> LENGTH: 13
<212> TYPE: PRT
<213> ORGANISM: Artificial Sequence
<220> FEATURE:
<223> OTHER INFORMATION: immunogenic peptide from in-frame deletion in
      EGFR

<400> SEQUENCE: 116

Leu Glu Glu Lys Lys Gly Asn Tyr Trp Thr Asp His Cys
1               5                   10

<210> SEQ ID NO 117
<211> LENGTH: 100
<212> TYPE: PRT
<213> ORGANISM: Artificial Sequence
<220> FEATURE:
<223> OTHER INFORMATION: cTRP

<400> SEQUENCE: 117

Met Gly Lys Ser Pro Thr Glu Val Leu Leu Glu Leu Ile Ala Glu Ala
1               5                   10                  15

Ser Gly Thr Thr Arg Glu Glu Val Lys Glu Lys Phe Leu Lys Glu Leu
                20                  25                  30

Arg Lys Gly Lys Ser Pro Thr Glu Val Leu Leu Glu Leu Ile Ala Glu
            35                  40                  45

Ala Ser Gly Thr Thr Lys Glu Glu Val Lys Glu Lys Phe Leu Lys Glu
50                  55                  60

Leu Ser Phe Gly Lys Ser Pro Thr Glu Val Leu Leu Glu Leu Ile Ala
65                  70                  75                  80

Glu Ala Ser Gly Thr Thr Lys Glu Glu Val Lys Lys Lys Phe Trp Lys
                85                  90                  95

Glu Leu Ser Leu
            100

<210> SEQ ID NO 118
<211> LENGTH: 199
<212> TYPE: PRT
<213> ORGANISM: Artificial Sequence
<220> FEATURE:
<223> OTHER INFORMATION: cTRP

<400> SEQUENCE: 118

Met Gly Asp Lys Thr Ala Ile Ala Gln Ile Leu Ala Ile Lys Ala Ser
1               5                   10                  15

Ala Lys Gly Asp Glu Thr Glu Leu Glu Arg Ala Leu Arg Tyr Ala Val
                20                  25                  30

Lys Val Gly Asp Lys Thr Ala Ile Ala Gln Ile Leu Ala Ile Lys Ala
            35                  40                  45
```

```
Ser Ala Lys Gly Asp Glu Thr Glu Leu Glu Gln Ala Leu Arg Tyr Ala
    50              55                  60

Lys Phe Val Gly Asp Lys Thr Ala Ile Ala Gln Ile Leu Ala Ile Lys
65              70                  75                      80

Ala Ser Ala Lys Gly Asp Glu Leu Glu Leu Thr Arg Ala Leu Ala Tyr
                85                  90                  95

Ala Lys Lys Val Gly Asp Lys Thr Ala Ile Ala Gln Ile Leu Ala Ile
                100                 105                 110

Lys Ala Ser Ala Lys Gly Asp Glu Thr Glu Leu Glu Arg Ala Leu Arg
        115                 120                 125

Tyr Ala Lys Leu Val Gly Asp Lys Thr Ala Ile Ala Gln Ile Leu Ala
    130                 135                 140

Ile Lys Ala Ser Ala Lys Gly Asp Glu Thr Glu Leu Glu Arg Ala Leu
145                 150                 155                 160

Arg Tyr Ala Lys Tyr Val Gly Asp Lys Thr Ala Ile Ala Gln Ile Leu
                165                 170                 175

Ala Ile Lys Ala Ser Ala Lys Gly Asp Glu Pro Glu Leu Glu Tyr Ala
                180                 185                 190

Leu Ala Tyr Ala Lys Lys Val
            195
```

<210> SEQ ID NO 119
<211> LENGTH: 221
<212> TYPE: PRT
<213> ORGANISM: Artificial Sequence
<220> FEATURE:
<223> OTHER INFORMATION: cTRP

<400> SEQUENCE: 119

```
Leu Val Ser Leu Glu Gln Ala Leu Lys Ile Leu Lys Val Ala Ala Glu
1               5                   10                  15

Leu Gly Thr Thr Val Glu Glu Ala Val Lys Arg Ala Leu Lys Leu Lys
                20                  25                  30

Thr Lys Leu Gly Val Ser Leu Glu Gln Ala Leu Lys Ile Leu Glu Val
            35                  40                  45

Ala Ala Glu Leu Gly Thr Thr Val Glu Glu Ala Val Lys Arg Ala Leu
    50                  55                  60

Lys Leu Lys Thr Lys Leu Gly Val Ser Leu Glu Gln Ala Leu Lys Ile
65              70                  75                      80

Leu Glu Val Ala Ala Lys Leu Gly Thr Thr Val Glu Glu Ala Val Lys
                85                  90                  95

Arg Ala Leu Lys Leu Lys Thr Lys Leu Gly Val Ser Leu Glu Gln Ala
                100                 105                 110

Leu Lys Ile Leu Lys Val Ala Ala Glu Leu Gly Thr Thr Val Glu Glu
            115                 120                 125

Ala Val Lys Arg Ala Leu Lys Leu Lys Thr Lys Leu Gly Val Ser Leu
    130                 135                 140

Glu Gln Ala Leu Lys Ile Leu Glu Val Ala Ala Glu Leu Gly Thr Thr
145                 150                 155                 160

Val Glu Glu Ala Val Lys Arg Ala Met Lys Leu Lys Thr Lys Leu Gly
                165                 170                 175

Val Ser Leu Glu Gln Ala Leu Lys Ile Leu Glu Val Ala Ala Lys Leu
                180                 185                 190

Gly Thr Thr Val Glu Glu Ala Val Lys Arg Ala Leu Lys Leu Lys Thr
            195                 200                 205
```

```
Lys Leu Gly Gly Trp Leu Glu His His His His His
    210             215                 220

<210> SEQ ID NO 120
<211> LENGTH: 286
<212> TYPE: PRT
<213> ORGANISM: Artificial Sequence
<220> FEATURE:
<223> OTHER INFORMATION: cTRP

<400> SEQUENCE: 120

Gly Ser Ser Met Ala Ser Gly Ile Ser Val Glu Glu Leu Leu Lys Leu
1               5                   10                  15

Ala Lys Ala Ala Tyr Tyr Ser Gly Thr Thr Val Glu Glu Ala Tyr Lys
            20                  25                  30

Leu Ala Leu Lys Leu Gly Ile Ser Val Glu Glu Leu Leu Lys Leu Ala
        35                  40                  45

Glu Ala Ala Tyr Tyr Ser Gly Thr Thr Val Glu Glu Ala Tyr Lys Leu
    50                  55                  60

Ala Leu Lys Leu Gly Ile Ser Val Glu Glu Leu Leu Lys Leu Ala Lys
65                  70                  75                  80

Ala Ala Tyr Tyr Ser Gly Thr Thr Val Glu Glu Ala Tyr Lys Leu Ala
                85                  90                  95

Leu Lys Leu Gly Ile Ser Val Glu Glu Leu Leu Lys Leu Ala Lys Ala
            100                 105                 110

Ala Tyr Tyr Ser Gly Thr Thr Val Glu Glu Ala Tyr Lys Leu Ala Leu
        115                 120                 125

Lys Leu Gly Ile Ser Val Glu Glu Leu Leu Lys Leu Ala Glu Ala Ala
    130                 135                 140

Tyr Tyr Ser Gly Thr Thr Val Glu Glu Ala Tyr Lys Leu Ala Leu Lys
145                 150                 155                 160

Leu Gly Ile Ser Val Glu Glu Leu Leu Lys Leu Ala Lys Ala Ala Tyr
                165                 170                 175

Tyr Ser Gly Thr Thr Val Glu Glu Ala Tyr Lys Leu Ala Leu Lys Leu
            180                 185                 190

Gly Ile Ser Val Glu Glu Leu Leu Lys Leu Ala Lys Ala Ala Tyr Tyr
        195                 200                 205

Ser Gly Thr Thr Val Glu Glu Ala Tyr Lys Leu Ala Leu Lys Leu Gly
    210                 215                 220

Ile Ser Val Glu Glu Leu Leu Lys Leu Ala Glu Ala Ala Tyr Tyr Ser
225                 230                 235                 240

Gly Thr Thr Val Glu Glu Ala Tyr Lys Leu Ala Leu Lys Leu Gly Ile
                245                 250                 255

Ser Val Glu Glu Leu Leu Lys Leu Ala Lys Ala Ala Tyr Tyr Ser Gly
            260                 265                 270

Thr Thr Val Glu Glu Ala Tyr Lys Leu Ala Leu Lys Leu Gly
        275                 280                 285

<210> SEQ ID NO 121
<211> LENGTH: 379
<212> TYPE: PRT
<213> ORGANISM: Artificial Sequence
<220> FEATURE:
<223> OTHER INFORMATION: cTRP

<400> SEQUENCE: 121

Gly Ser Ser Met Ala Ser Gly Ile Ser Val Glu Glu Leu Leu Lys Leu
1               5                   10                  15
```

Ala Lys Ala Ala Tyr Tyr Ser Gly Thr Thr Val Glu Glu Ala Tyr Lys
            20                  25                  30

Leu Ala Leu Lys Leu Gly Ile Ser Val Glu Glu Leu Leu Lys Leu Ala
        35                  40                  45

Glu Ala Ala Tyr Tyr Ser Gly Thr Thr Val Glu Glu Ala Tyr Lys Leu
    50                  55                  60

Ala Leu Lys Leu Gly Ile Ser Val Glu Glu Leu Leu Lys Leu Ala Lys
65                  70                  75                  80

Ala Ala Tyr Tyr Ser Gly Thr Thr Val Glu Glu Ala Tyr Lys Leu Ala
                85                  90                  95

Leu Lys Leu Gly Ile Ser Val Glu Glu Leu Leu Lys Leu Ala Lys Ala
            100                 105                 110

Ala Tyr Tyr Ser Gly Thr Thr Val Glu Glu Ala Tyr Lys Leu Ala Leu
        115                 120                 125

Lys Leu Gly Ile Ser Val Glu Glu Leu Leu Lys Leu Ala Glu Ala Ala
    130                 135                 140

Tyr Tyr Ser Gly Thr Thr Val Glu Glu Ala Tyr Lys Leu Ala Leu Lys
145                 150                 155                 160

Leu Gly Ile Ser Val Glu Glu Leu Leu Lys Leu Ala Lys Ala Ala Tyr
                165                 170                 175

Tyr Ser Gly Thr Thr Val Glu Glu Ala Tyr Lys Leu Ala Leu Lys Leu
            180                 185                 190

Gly Ile Ser Val Glu Glu Leu Leu Lys Leu Ala Lys Ala Ala Tyr Tyr
        195                 200                 205

Ser Gly Thr Thr Val Glu Glu Ala Tyr Lys Leu Ala Leu Lys Leu Gly
    210                 215                 220

Ile Ser Val Glu Glu Leu Leu Lys Leu Ala Glu Ala Ala Tyr Tyr Ser
225                 230                 235                 240

Gly Thr Thr Val Glu Glu Ala Tyr Lys Leu Ala Leu Lys Leu Gly Ile
                245                 250                 255

Ser Val Glu Glu Leu Leu Lys Leu Ala Lys Ala Ala Tyr Tyr Ser Gly
            260                 265                 270

Thr Thr Val Glu Glu Ala Tyr Lys Leu Ala Leu Lys Leu Gly Ile Ser
        275                 280                 285

Val Glu Glu Leu Leu Lys Leu Ala Lys Ala Ala Tyr Tyr Ser Gly Thr
    290                 295                 300

Thr Val Glu Glu Ala Tyr Lys Leu Ala Leu Lys Leu Gly Ile Ser Val
305                 310                 315                 320

Glu Glu Leu Leu Lys Leu Ala Glu Ala Ala Tyr Tyr Ser Gly Thr Thr
                325                 330                 335

Val Glu Glu Ala Tyr Lys Leu Ala Leu Lys Leu Gly Ile Ser Val Glu
            340                 345                 350

Glu Leu Leu Lys Leu Ala Lys Ala Ala Tyr Tyr Ser Gly Thr Thr Val
        355                 360                 365

Glu Glu Ala Tyr Lys Leu Ala Leu Lys Leu Gly
    370                 375

<210> SEQ ID NO 122
<211> LENGTH: 100
<212> TYPE: PRT
<213> ORGANISM: Artificial Sequence
<220> FEATURE:
<223> OTHER INFORMATION: cTRP

<400> SEQUENCE: 122

```
Gly Ser Ser Met Ala Ser Gly Ile Ser Val Glu Glu Leu Leu Lys Leu
1               5                   10                  15

Ala Lys Ala Ala Tyr Tyr Ser Gly Thr Thr Val Glu Glu Ala Tyr Lys
            20                  25                  30

Leu Ala Leu Lys Leu Gly Ile Ser Val Glu Glu Leu Leu Lys Leu Ala
        35                  40                  45

Glu Ala Ala Tyr Tyr Ser Gly Thr Thr Val Glu Glu Ala Tyr Lys Leu
    50                  55                  60

Ala Leu Lys Leu Gly Ile Ser Val Glu Glu Leu Leu Lys Leu Ala Lys
65                  70                  75                  80

Ala Ala Tyr Tyr Ser Gly Thr Thr Val Glu Glu Ala Tyr Lys Leu Ala
                85                  90                  95

Leu Lys Leu Gly
            100
```

<210> SEQ ID NO 123
<211> LENGTH: 795
<212> TYPE: PRT
<213> ORGANISM: Artificial Sequence
<220> FEATURE:
<223> OTHER INFORMATION: cTRP

<400> SEQUENCE: 123

```
Gly Leu Gly Leu Asn Pro Glu Ala Ile Lys Ala Ala Glu Leu Gly
1               5                   10                  15

Lys Ala Gly Ile Ser Ser Glu Glu Ile Leu Glu Leu Leu Arg Ala Ala
            20                  25                  30

His Glu Leu Gly Leu Asn Pro Glu Ala Ile Lys Ala Ala Ala Glu Leu
        35                  40                  45

Gly Lys Ala Gly Ile Ser Ser Glu Glu Ile Leu Glu Leu Leu Arg Ala
    50                  55                  60

Ala His Glu Leu Gly Leu Asn Pro Glu Ala Ile Lys Ala Ala Ala Glu
65                  70                  75                  80

Leu Gly Lys Ala Gly Ile Ser Ser Glu Glu Ile Leu Glu Leu Leu Arg
                85                  90                  95

Ala Ala His Ala Leu Gly Leu Asn Pro Glu Ala Ile Lys Ala Ala Ala
            100                 105                 110

Glu Leu Gly Lys Ala Gly Ile Ser Ser Ala Glu Ile Leu Glu Leu Leu
        115                 120                 125

Met Ala Ala His Glu Leu Gly Leu Asn Pro Glu Ala Ile Lys Ala Ala
    130                 135                 140

Ala Glu Leu Gly Lys Ala Gly Ile Ser Ser Glu Glu Ile Leu Glu Leu
145                 150                 155                 160

Leu Arg Ala Ala His Glu Leu Gly Leu Asn Pro Glu Ala Ile Lys Ala
                165                 170                 175

Ala Ala Glu Leu Gly Lys Ala Gly Ile Ser Ser Glu Glu Ile Leu Glu
            180                 185                 190

Leu Leu Arg Ala Ala His Gly Leu Gly Leu Asn Pro Glu Ala Ile Lys
        195                 200                 205

Ala Ala Ala Glu Leu Gly Lys Ala Gly Ile Ser Glu Glu Ile Leu
    210                 215                 220

Glu Leu Leu Arg Ala Ala His Glu Leu Gly Leu Asn Pro Glu Ala Ile
225                 230                 235                 240

Lys Ala Ala Ala Glu Leu Gly Lys Ala Gly Ile Ser Ser Glu Glu Ile
                245                 250                 255
```

-continued

```
Leu Glu Leu Leu Arg Ala Ala His Glu Leu Gly Leu Asn Pro Glu Ala
            260                 265                 270
Ile Lys Ala Ala Ala Glu Leu Gly Lys Ala Gly Ile Ser Ser Glu Glu
            275                 280                 285
Ile Leu Glu Leu Leu Arg Ala Ala His Ala Leu Gly Leu Asn Pro Glu
            290                 295                 300
Ala Ile Lys Ala Ala Ala Glu Leu Gly Lys Ala Gly Ile Ser Ser Ala
305                 310                 315                 320
Glu Ile Leu Glu Leu Leu Met Ala Ala His Glu Leu Gly Leu Asn Pro
            325                 330                 335
Glu Ala Ile Lys Ala Ala Ala Glu Leu Gly Lys Ala Gly Ile Ser Ser
            340                 345                 350
Glu Glu Ile Leu Glu Leu Leu Arg Ala Ala His Glu Leu Gly Leu Asn
            355                 360                 365
Pro Glu Ala Ile Lys Ala Ala Ala Glu Leu Gly Lys Ala Gly Ile Ser
            370                 375                 380
Ser Glu Glu Ile Leu Glu Leu Leu Arg Ala Ala His Gly Leu Gly Leu
385                 390                 395                 400
Asn Pro Glu Ala Ile Lys Ala Ala Ala Glu Leu Gly Lys Ala Gly Ile
            405                 410                 415
Ser Ser Glu Glu Ile Leu Glu Leu Leu Arg Ala Ala His Glu Leu Gly
            420                 425                 430
Leu Asn Pro Glu Ala Ile Lys Ala Ala Ala Glu Leu Gly Lys Ala Gly
            435                 440                 445
Ile Ser Ser Glu Glu Ile Leu Glu Leu Leu Arg Ala Ala His Glu Leu
            450                 455                 460
Gly Leu Asn Pro Glu Ala Ile Lys Ala Ala Ala Glu Leu Gly Lys Ala
465                 470                 475                 480
Gly Ile Ser Ser Glu Glu Ile Leu Glu Leu Leu Arg Ala Ala His Ala
            485                 490                 495
Leu Gly Leu Asn Pro Glu Ala Ile Lys Ala Ala Ala Glu Leu Gly Lys
            500                 505                 510
Ala Gly Ile Ser Ser Ala Glu Ile Leu Glu Leu Leu Met Ala Ala His
            515                 520                 525
Glu Leu Gly Leu Asn Pro Glu Ala Ile Lys Ala Ala Ala Glu Leu Gly
            530                 535                 540
Lys Ala Gly Ile Ser Ser Glu Glu Ile Leu Glu Leu Leu Arg Ala Ala
545                 550                 555                 560
His Glu Leu Gly Leu Asn Pro Glu Ala Ile Lys Ala Ala Ala Glu Leu
            565                 570                 575
Gly Lys Ala Gly Ile Ser Ser Glu Glu Ile Leu Glu Leu Leu Arg Ala
            580                 585                 590
Ala His Gly Leu Gly Leu Asn Pro Glu Ala Ile Lys Ala Ala Ala Glu
            595                 600                 605
Leu Gly Lys Ala Gly Ile Ser Ser Glu Glu Ile Leu Glu Leu Leu Arg
            610                 615                 620
Ala Ala His Glu Leu Gly Leu Asn Pro Glu Ala Ile Lys Ala Ala Ala
625                 630                 635                 640
Glu Leu Gly Lys Ala Gly Ile Ser Ser Glu Glu Ile Leu Glu Leu Leu
            645                 650                 655
Arg Ala Ala His Glu Leu Gly Leu Asn Pro Glu Ala Ile Lys Ala Ala
            660                 665                 670
```

```
Ala Glu Leu Gly Lys Ala Gly Ile Ser Ser Glu Ile Leu Glu Leu
            675                 680                 685

Leu Arg Ala Ala His Ala Leu Gly Leu Asn Pro Glu Ala Ile Lys Ala
        690                 695                 700

Ala Ala Glu Leu Gly Lys Ala Gly Ile Ser Ser Ala Glu Ile Leu Glu
705                 710                 715                 720

Leu Leu Met Ala Ala His Glu Leu Gly Leu Asn Pro Glu Ala Ile Lys
                725                 730                 735

Ala Ala Ala Glu Leu Gly Lys Ala Gly Ile Ser Ser Glu Glu Ile Leu
            740                 745                 750

Glu Leu Leu Arg Ala Ala His Glu Leu Gly Leu Asn Pro Glu Ala Ile
                755                 760                 765

Lys Ala Ala Ala Glu Leu Gly Lys Ala Gly Ile Ser Ser Glu Glu Ile
        770                 775                 780

Leu Glu Leu Leu Arg Ala Ala His Gly Gly Trp
785                 790                 795

<210> SEQ ID NO 124
<211> LENGTH: 13
<212> TYPE: PRT
<213> ORGANISM: Artificial Sequence
<220> FEATURE:
<223> OTHER INFORMATION: repetitive sequences forming alpha helical
      structures

<400> SEQUENCE: 124

Pro Glu Ala Ile Lys Ala Ala Ala Glu Leu Gly Lys Ala
1               5                   10

<210> SEQ ID NO 125
<211> LENGTH: 14
<212> TYPE: PRT
<213> ORGANISM: Artificial Sequence
<220> FEATURE:
<223> OTHER INFORMATION: repetitive sequences forming alpha helical
      structures

<400> SEQUENCE: 125

Ser Glu Glu Ile Leu Glu Leu Leu Arg Ala Ala His Glu Leu
1               5                   10

<210> SEQ ID NO 126
<211> LENGTH: 14
<212> TYPE: PRT
<213> ORGANISM: Artificial Sequence
<220> FEATURE:
<223> OTHER INFORMATION: repetitive sequences forming alpha helical
      structures

<400> SEQUENCE: 126

Ser Glu Glu Ile Leu Glu Leu Leu Arg Ala Ala His Ala Leu
1               5                   10

<210> SEQ ID NO 127
<211> LENGTH: 14
<212> TYPE: PRT
<213> ORGANISM: Artificial Sequence
<220> FEATURE:
<223> OTHER INFORMATION: repetitive sequences forming alpha helical
      structures

<400> SEQUENCE: 127

Ser Ala Glu Ile Leu Glu Leu Leu Met Ala Ala His Glu Leu
1               5                   10
```

-continued

<210> SEQ ID NO 128
<211> LENGTH: 14
<212> TYPE: PRT
<213> ORGANISM: Artificial Sequence
<220> FEATURE:
<223> OTHER INFORMATION: repetitive sequences forming alpha helical
      structures

<400> SEQUENCE: 128

Ser Glu Glu Ile Leu Glu Leu Leu Arg Ala Ala His Gly Leu
1               5                   10

<210> SEQ ID NO 129
<211> LENGTH: 14
<212> TYPE: PRT
<213> ORGANISM: Artificial Sequence
<220> FEATURE:
<223> OTHER INFORMATION: repetitive sequences forming alpha helical
      structures

<400> SEQUENCE: 129

Ser Glu Glu Ile Leu Glu Leu Leu Arg Ala Ala His Gly Gly
1               5                   10

<210> SEQ ID NO 130
<211> LENGTH: 33
<212> TYPE: PRT
<213> ORGANISM: Artificial Sequence
<220> FEATURE:
<223> OTHER INFORMATION: repetitive sequences forming alpha helical
      structures joined by linkers

<400> SEQUENCE: 130

Gly Leu Asn Pro Glu Ala Ile Lys Ala Ala Ala Glu Leu Gly Lys Ala
1               5                   10                  15

Gly Ile Ser Ser Glu Glu Ile Leu Glu Leu Leu Arg Ala Ala His Glu
            20                  25                  30

Leu

<210> SEQ ID NO 131
<211> LENGTH: 33
<212> TYPE: PRT
<213> ORGANISM: Artificial Sequence
<220> FEATURE:
<223> OTHER INFORMATION: repetitive sequences forming alpha helical
      structures joined by linkers

<400> SEQUENCE: 131

Gly Leu Asn Pro Glu Ala Ile Lys Ala Ala Ala Glu Leu Gly Lys Ala
1               5                   10                  15

Gly Ile Ser Ser Glu Glu Ile Leu Glu Leu Leu Arg Ala Ala His Ala
            20                  25                  30

Leu

<210> SEQ ID NO 132
<211> LENGTH: 33
<212> TYPE: PRT
<213> ORGANISM: Artificial Sequence
<220> FEATURE:
<223> OTHER INFORMATION: repetitive sequences forming alpha helical
      structures joined by linkers

<400> SEQUENCE: 132

Gly Leu Asn Pro Glu Ala Ile Lys Ala Ala Ala Glu Leu Gly Lys Ala

```
                1               5                  10                 15
Gly Ile Ser Ser Ala Glu Ile Leu Glu Leu Leu Met Ala Ala His Glu
                20                 25                 30
Leu
```

<210> SEQ ID NO 133
<211> LENGTH: 33
<212> TYPE: PRT
<213> ORGANISM: Artificial Sequence
<220> FEATURE:
<223> OTHER INFORMATION: repetitive sequences forming alpha helical
      structures joined by linkers

<400> SEQUENCE: 133

```
Gly Leu Asn Pro Glu Ala Ile Lys Ala Ala Glu Leu Gly Lys Ala
1               5                  10                 15
Gly Ile Ser Ser Glu Glu Ile Leu Glu Leu Leu Arg Ala Ala His Gly
                20                 25                 30
Leu
```

<210> SEQ ID NO 134
<211> LENGTH: 33
<212> TYPE: PRT
<213> ORGANISM: Artificial Sequence
<220> FEATURE:
<223> OTHER INFORMATION: repetitive sequences forming alpha helical
      structures joined by linkers

<400> SEQUENCE: 134

```
Gly Leu Asn Pro Glu Ala Ile Lys Ala Ala Ala Glu Leu Gly Lys Ala
1               5                  10                 15
Gly Ile Ser Ser Glu Glu Ile Leu Glu Leu Leu Arg Ala Ala His Gly
                20                 25                 30
Gly
```

<210> SEQ ID NO 135
<211> LENGTH: 271
<212> TYPE: PRT
<213> ORGANISM: Artificial Sequence
<220> FEATURE:
<223> OTHER INFORMATION: design_24x_sub8_Protein

<400> SEQUENCE: 135

```
Gly Ser Ser Met Gly Leu Asp Pro Glu Ala Ile Lys Ala Ala Glu
1               5                  10                 15
Leu Gly Lys Ala Gly Ile Ser Ser Glu Glu Ile Leu Glu Leu Leu Arg
                20                 25                 30
Ala Ala His Glu Leu Gly Leu Asp Pro Glu Ala Ile Lys Ala Ala
        35                 40                 45
Glu Leu Gly Lys Ala Gly Ile Ser Ser Glu Glu Ile Leu Glu Leu Leu
    50                 55                 60
Arg Ala Ala His Glu Leu Gly Leu Asp Pro Glu Ala Ile Lys Ala Ala
65                 70                 75                 80
Ala Glu Leu Gly Lys Ala Gly Ile Ser Ser Glu Glu Ile Leu Glu Leu
                85                 90                 95
Leu Arg Ala Ala His Val Leu Gly Leu Asp Pro Glu Ala Ile Lys Ala
            100                105                110
Ala Ala Glu Leu Gly Lys Ala Gly Ile Ser Ser Glu Glu Ile Leu Glu
            115                120                125
```

Leu Leu Val Ala Ala His Leu Gly Leu Asp Pro Glu Ala Ile Lys
130                 135                 140

Ala Ala Ala Glu Leu Gly Lys Ala Gly Ile Ser Ser Glu Glu Ile Leu
145                 150                 155                 160

Glu Leu Leu Arg Ala Ala His Glu Leu Gly Leu Asp Pro Glu Ala Ile
                165                 170                 175

Lys Ala Ala Ala Glu Leu Gly Lys Ala Gly Ile Ser Ser Glu Glu Ile
                180                 185                 190

Leu Glu Leu Leu Arg Ala Ala His Glu Leu Gly Leu Asp Pro Glu Ala
                195                 200                 205

Ile Lys Ala Ala Ala Glu Leu Gly Lys Ala Gly Ile Ser Ser Glu Glu
210                 215                 220

Ile Leu Glu Leu Leu Arg Ala Ala His Glu Leu Gly Leu Asp Pro Glu
225                 230                 235                 240

Ala Ile Lys Ala Ala Ala Glu Leu Gly Lys Ala Gly Ile Ser Ser Ile
                245                 250                 255

Glu Ile Leu Glu Leu Leu Arg Ala Ala His Glu Leu Gly Gly Trp
                260                 265                 270

<210> SEQ ID NO 136
<211> LENGTH: 203
<212> TYPE: PRT
<213> ORGANISM: Artificial Sequence
<220> FEATURE:
<223> OTHER INFORMATION: design_24x_sub6_Protein

<400> SEQUENCE: 136

Gly Ser Ser Met Gly Leu Asp Pro Glu Ala Ile Lys Ala Ala Ala Glu
1               5                   10                  15

Leu Gly Lys Ala Gly Ile Ser Ser Glu Glu Ile Leu Glu Leu Leu Arg
                20                  25                  30

Ala Ala His Glu Leu Gly Leu Asp Pro Glu Ala Ile Lys Ala Ala Ala
                35                  40                  45

Glu Leu Gly Lys Ala Gly Ile Ser Ser Glu Glu Ile Leu Glu Leu Leu
50                  55                  60

Arg Ala Ala His Glu Leu Gly Leu Asp Pro Glu Ala Ile Lys Ala Ala
65                  70                  75                  80

Ala Glu Leu Gly Lys Ala Gly Ile Ser Ser Glu Glu Ile Leu Glu Leu
                85                  90                  95

Leu Arg Ala Ala His Glu Leu Gly Leu Asp Pro Glu Ala Ile Lys Ala
                100                 105                 110

Ala Ala Glu Leu Gly Lys Ala Gly Ile Ser Ser Glu Glu Ile Leu Glu
                115                 120                 125

Leu Leu Arg Ala Ala His Glu Leu Gly Leu Asp Pro Glu Ala Ile Lys
                130                 135                 140

Ala Ala Ala Glu Leu Gly Lys Ala Gly Ile Ser Ser Glu Glu Ile Leu
145                 150                 155                 160

Glu Leu Leu Arg Ala Ala His Glu Leu Gly Leu Asp Pro Glu Ala Ile
                165                 170                 175

Lys Ala Ala Ala Glu Leu Gly Lys Ala Gly Ile Ser Ser Glu Glu Ile
                180                 185                 190

Leu Glu Leu Leu Arg Ala Ala His Glu Leu Gly
                195                 200

<210> SEQ ID NO 137
<211> LENGTH: 137

```
<212> TYPE: PRT
<213> ORGANISM: Artificial Sequence
<220> FEATURE:
<223> OTHER INFORMATION: design_24x_sub4_Protein

<400> SEQUENCE: 137

Gly Ser Ser Met Gly Leu Asp Pro Glu Ala Ile Lys Ala Ala Ala Glu
1               5                   10                  15

Leu Gly Lys Ala Gly Ile Ser Ser Glu Glu Ile Leu Glu Leu Leu Arg
            20                  25                  30

Ala Ala His Glu Leu Gly Leu Asp Pro Glu Ala Ile Lys Ala Ala Ala
        35                  40                  45

Glu Leu Gly Lys Ala Gly Ile Ser Ser Glu Glu Ile Leu Glu Leu Leu
50                  55                  60

Arg Ala Ala His Glu Leu Gly Leu Asp Pro Glu Ala Ile Lys Ala Ala
65                  70                  75                  80

Ala Glu Leu Gly Lys Ala Gly Ile Ser Ser Glu Glu Ile Leu Glu Leu
                85                  90                  95

Leu Arg Ala Ala His Glu Leu Gly Leu Asp Pro Glu Ala Ile Lys Ala
            100                 105                 110

Ala Ala Glu Leu Gly Lys Ala Gly Ile Ser Ser Glu Glu Ile Leu Glu
        115                 120                 125

Leu Leu Arg Ala Ala His Glu Leu Gly
    130                 135

<210> SEQ ID NO 138
<211> LENGTH: 104
<212> TYPE: PRT
<213> ORGANISM: Artificial Sequence
<220> FEATURE:
<223> OTHER INFORMATION: design_24x_sub3_Protein

<400> SEQUENCE: 138

Gly Ser Ser Met Gly Leu Asp Pro Glu Ala Ile Lys Ala Ala Ala Glu
1               5                   10                  15

Leu Gly Lys Ala Gly Ile Ser Ser Glu Glu Ile Leu Glu Leu Leu Arg
            20                  25                  30

Ala Ala His Glu Leu Gly Leu Asp Pro Glu Ala Ile Lys Ala Ala Ala
        35                  40                  45

Glu Leu Gly Lys Ala Gly Ile Ser Ser Glu Glu Ile Leu Glu Leu Leu
50                  55                  60

Arg Ala Ala His Glu Leu Gly Leu Asp Pro Glu Ala Ile Lys Ala Ala
65                  70                  75                  80

Ala Glu Leu Gly Lys Ala Gly Ile Ser Ser Glu Glu Ile Leu Glu Leu
                85                  90                  95

Leu Arg Ala Ala His Glu Leu Gly
            100

<210> SEQ ID NO 139
<211> LENGTH: 14
<212> TYPE: PRT
<213> ORGANISM: Artificial Sequence
<220> FEATURE:
<223> OTHER INFORMATION: repetitive sequences forming alpha helical
      structures

<400> SEQUENCE: 139

Ser Glu Glu Ile Leu Glu Leu Leu Arg Ala Ala His Val Leu
1               5                   10
```

<210> SEQ ID NO 140
<211> LENGTH: 14
<212> TYPE: PRT
<213> ORGANISM: Artificial Sequence
<220> FEATURE:
<223> OTHER INFORMATION: repetitive sequences forming alpha helical
      structures

<400> SEQUENCE: 140

Ser Ile Glu Ile Leu Glu Leu Leu Arg Ala Ala His Glu Leu
1               5                   10

<210> SEQ ID NO 141
<211> LENGTH: 33
<212> TYPE: PRT
<213> ORGANISM: Artificial Sequence
<220> FEATURE:
<223> OTHER INFORMATION: repetitive sequences forming alpha helical
      structures

<400> SEQUENCE: 141

Gly Leu Asp Pro Glu Ala Ile Lys Ala Ala Ala Glu Leu Gly Lys Ala
1               5                   10                  15

Gly Ile Ser Ser Glu Glu Ile Leu Glu Leu Leu Arg Ala Ala His Glu
                20                  25                  30

Leu

<210> SEQ ID NO 142
<211> LENGTH: 33
<212> TYPE: PRT
<213> ORGANISM: Artificial Sequence
<220> FEATURE:
<223> OTHER INFORMATION: repetitive sequences forming alpha helical
      structures

<400> SEQUENCE: 142

Gly Leu Asp Pro Glu Ala Ile Lys Ala Ala Ala Glu Leu Gly Lys Ala
1               5                   10                  15

Gly Ile Ser Ser Glu Glu Ile Leu Glu Leu Leu Arg Ala Ala His Val
                20                  25                  30

Leu

<210> SEQ ID NO 143
<211> LENGTH: 33
<212> TYPE: PRT
<213> ORGANISM: Artificial Sequence
<220> FEATURE:
<223> OTHER INFORMATION: repetitive sequences forming alpha helical
      structures

<400> SEQUENCE: 143

Gly Leu Asp Pro Glu Ala Ile Lys Ala Ala Ala Glu Leu Gly Lys Ala
1               5                   10                  15

Gly Ile Ser Ser Glu Glu Ile Leu Glu Leu Leu Val Ala Ala His Leu
                20                  25                  30

Leu

<210> SEQ ID NO 144
<211> LENGTH: 33
<212> TYPE: PRT
<213> ORGANISM: Artificial Sequence
<220> FEATURE:
<223> OTHER INFORMATION: repetitive sequences forming alpha helical
      structures

<400> SEQUENCE: 144

Gly Leu Asp Pro Glu Ala Ile Lys Ala Ala Glu Leu Gly Lys Ala
1               5                   10                  15

Gly Ile Ser Ser Ile Glu Ile Leu Glu Leu Leu Arg Ala Ala His Glu
            20                  25                  30

Leu

<210> SEQ ID NO 145
<211> LENGTH: 514
<212> TYPE: PRT
<213> ORGANISM: Artificial Sequence
<220> FEATURE:
<223> OTHER INFORMATION: cTRP

<400> SEQUENCE: 145

Gly Asn Leu Glu Leu Ala Leu Lys Ala Leu Gln Ile Leu Val Asn Ala
1               5                   10                  15

Ala Tyr Val Leu Ala Glu Ile Ala Arg Asp Arg Gly Asn Glu Glu Leu
            20                  25                  30

Leu Glu Lys Ala Ala Arg Leu Ala Glu Ala Ala Arg Gln Ala Glu
        35                  40                  45

Glu Ile Ala Arg Gln Ala Arg Lys Glu Gly Asn Leu Glu Leu Ala Leu
 50                  55                  60

Lys Ala Leu Gln Ile Leu Val Asn Ala Ala Tyr Val Leu Ala Glu Ile
 65                  70                  75                  80

Ala Arg Asp Arg Gly Asn Glu Glu Leu Leu Glu Lys Ala Ala Arg Leu
                85                  90                  95

Ala Glu Glu Ala Ala Arg Gln Ala Glu Glu Ile Ala Arg Gln Ala Arg
            100                 105                 110

Lys Glu Gly Asn Leu Glu Leu Ala Leu Lys Ala Leu Gln Ile Leu Val
        115                 120                 125

Asn Ala Ala Tyr Val Leu Ala Glu Ile Ala Arg Asp Arg Gly Asn Glu
130                 135                 140

Glu Leu Leu Glu Lys Ala Ala Arg Leu Ala Glu Glu Ala Ala Arg Gln
145                 150                 155                 160

Ala Glu Glu Ile Ala Arg Gln Ala Arg Lys Glu Gly Asn Leu Glu Leu
                165                 170                 175

Ala Leu Lys Ala Leu Gln Ile Leu Val Asn Ala Ala Tyr Val Leu Ala
            180                 185                 190

Glu Ile Ala Arg Asp Arg Gly Asn Glu Glu Leu Leu Glu Lys Ala Ala
        195                 200                 205

Arg Leu Ala Glu Glu Ala Ala Arg Gln Ala Glu Glu Ile Ala Arg Gln
210                 215                 220

Ala Arg Lys Glu Gly Asn Leu Glu Leu Ala Leu Lys Ala Leu Gln Ile
225                 230                 235                 240

Leu Val Asn Ala Ala Tyr Val Leu Ala Glu Ile Ala Arg Asp Arg Gly
                245                 250                 255

Asn Glu Glu Leu Leu Glu Lys Ala Ala Arg Leu Ala Glu Glu Ala Ala
            260                 265                 270

Arg Gln Ala Glu Glu Ile Ala Arg Gln Ala Arg Lys Glu Gly Asn Leu
        275                 280                 285

Glu Leu Ala Leu Lys Ala Leu Gln Ile Leu Val Asn Ala Ala Tyr Val
290                 295                 300

Leu Ala Glu Ile Ala Arg Asp Arg Gly Asn Glu Glu Leu Leu Glu Lys

```
                305                 310                 315                 320
Ala Ala Arg Leu Ala Glu Glu Ala Ala Arg Gln Ala Glu Glu Ile Ala
                325                 330                 335
Arg Gln Ala Arg Lys Glu Gly Asn Leu Glu Leu Ala Leu Lys Ala Leu
                340                 345                 350
Gln Ile Leu Val Asn Ala Ala Tyr Val Leu Ala Glu Ile Ala Arg Asp
                355                 360                 365
Arg Gly Asn Glu Glu Leu Leu Glu Lys Ala Ala Arg Leu Ala Glu Glu
                370                 375                 380
Ala Ala Arg Gln Ala Glu Glu Ile Ala Arg Gln Ala Arg Lys Glu Gly
385                 390                 395                 400
Asn Leu Glu Leu Ala Leu Lys Ala Leu Gln Ile Leu Val Asn Ala Ala
                405                 410                 415
Tyr Val Leu Ala Glu Ile Ala Arg Asp Arg Gly Asn Glu Glu Leu Leu
                420                 425                 430
Glu Lys Ala Ala Arg Leu Ala Glu Glu Ala Ala Arg Gln Ala Glu Glu
                435                 440                 445
Ile Ala Arg Gln Ala Arg Lys Glu Gly Asn Leu Glu Leu Ala Leu Lys
                450                 455                 460
Ala Leu Gln Ile Leu Val Asn Ala Ala Tyr Val Leu Ala Glu Ile Ala
465                 470                 475                 480
Arg Asp Arg Gly Asn Glu Glu Leu Leu Glu Lys Ala Ala Arg Leu Ala
                485                 490                 495
Glu Glu Ala Ala Arg Gln Ala Glu Glu Ile Ala Arg Gln Ala Arg Lys
                500                 505                 510
Glu Gly

<210> SEQ ID NO 146
<211> LENGTH: 24
<212> TYPE: PRT
<213> ORGANISM: Artificial Sequence
<220> FEATURE:
<223> OTHER INFORMATION: repetitive sequences forming alpha helical
      structures

<400> SEQUENCE: 146

Glu Leu Ala Leu Lys Ala Leu Gln Ile Leu Val Asn Ala Ala Tyr Val
1               5                   10                  15

Leu Ala Glu Ile Ala Arg Asp Arg
            20

<210> SEQ ID NO 147
<211> LENGTH: 27
<212> TYPE: PRT
<213> ORGANISM: Artificial Sequence
<220> FEATURE:
<223> OTHER INFORMATION: repetitive sequences forming alpha helical
      structures

<400> SEQUENCE: 147

Glu Leu Leu Glu Lys Ala Ala Arg Leu Ala Glu Glu Ala Ala Arg Gln
1               5                   10                  15

Ala Glu Glu Ile Ala Arg Gln Ala Arg Lys Glu
            20                  25

<210> SEQ ID NO 148
<211> LENGTH: 57
<212> TYPE: PRT
<213> ORGANISM: Artificial Sequence
```

```
<220> FEATURE:
<223> OTHER INFORMATION: repetitive sequences forming alpha helical
      structures joined by linkers

<400> SEQUENCE: 148

Gly Asn Leu Glu Leu Ala Leu Lys Ala Leu Gln Ile Leu Val Asn Ala
1               5                   10                  15

Ala Tyr Val Leu Ala Glu Ile Ala Arg Asp Arg Gly Asn Glu Glu Leu
            20                  25                  30

Leu Glu Lys Ala Ala Arg Leu Ala Glu Glu Ala Ala Arg Gln Ala Glu
        35                  40                  45

Glu Ile Ala Arg Gln Ala Arg Lys Glu
    50                  55

<210> SEQ ID NO 149
<211> LENGTH: 511
<212> TYPE: PRT
<213> ORGANISM: Artificial Sequence
<220> FEATURE:
<223> OTHER INFORMATION: cTRP

<400> SEQUENCE: 149

Met Ala Ser Ser His His His His His His Ser Ser Gly Leu Val Pro
1               5                   10                  15

Arg Gly Ser Ser Met Gly Ile Ser Val Glu Glu Leu Leu Lys Leu Ala
            20                  25                  30

Lys Ala Ala Tyr Tyr Ser Gly Thr Thr Val Glu Glu Ala Tyr Lys Leu
        35                  40                  45

Ala Leu Lys Leu Gly Ile Ser Val Glu Glu Leu Leu Lys Leu Ala Glu
    50                  55                  60

Ala Ala Tyr Tyr Ser Gly Thr Thr Val Glu Glu Ala Tyr Lys Leu Ala
65                  70                  75                  80

Leu Lys Leu Gly Ile Ser Val Glu Glu Leu Leu Lys Leu Ala Lys Ala
                85                  90                  95

Ala Tyr Tyr Ser Gly Thr Thr Val Glu Glu Ala Tyr Lys Leu Ala Leu
            100                 105                 110

Lys Leu Gly Ile Ser Val Glu Glu Leu Leu Lys Leu Ala Lys Ala Ala
        115                 120                 125

Tyr Tyr Ser Gly Thr Thr Val Glu Glu Ala Tyr Lys Leu Ala Leu Lys
    130                 135                 140

Leu Gly Ile Ser Val Glu Glu Leu Leu Lys Leu Ala Glu Ala Ala Tyr
145                 150                 155                 160

Tyr Ser Gly Thr Thr Val Glu Glu Ala Tyr Lys Leu Ala Leu Lys Leu
                165                 170                 175

Gly Ile Ser Val Glu Glu Leu Leu Lys Leu Ala Lys Ala Ala Tyr Tyr
            180                 185                 190

Ser Gly Gly Ser Gly Gly Gly Ser Gly Ser Gly Ser Glu Trp Tyr
        195                 200                 205

Tyr Gly Asn Val Thr Arg His Gln Ala Glu Cys Ala Leu Asn Glu Arg
    210                 215                 220

Gly Val Glu Gly Asp Phe Leu Ile Arg Asp Ser Glu Ser Ser Pro Ser
225                 230                 235                 240

Asp Phe Ser Val Ser Leu Lys Ala Ser Gly Lys Asn Lys His Phe Lys
                245                 250                 255

Val Gln Leu Val Asp Asn Val Tyr Cys Ile Gly Gln Arg Arg Phe His
            260                 265                 270
```

Thr Met Asp Glu Leu Val Glu His Tyr Lys Lys Ala Pro Ile Phe Thr
    275                 280                 285

Ser Glu His Gly Glu Lys Leu Tyr Leu Val Arg Ala Leu Gln Gly Gly
    290                 295                 300

Ser Gly Gly Gly Ser Gly Ser Gly Thr Val Glu Glu Ala Tyr Lys Leu
305                 310                 315                 320

Ala Leu Lys Leu Gly Ile Ser Val Glu Glu Leu Leu Lys Leu Ala Lys
                325                 330                 335

Ala Ala Tyr Tyr Ser Gly Thr Thr Val Glu Glu Ala Tyr Lys Leu Ala
            340                 345                 350

Leu Lys Leu Gly Ile Ser Val Glu Glu Leu Leu Lys Leu Ala Glu Ala
        355                 360                 365

Ala Tyr Tyr Ser Gly Thr Thr Val Glu Glu Ala Tyr Lys Leu Ala Leu
    370                 375                 380

Lys Leu Gly Ile Ser Val Glu Glu Leu Leu Lys Leu Ala Lys Ala Ala
385                 390                 395                 400

Tyr Tyr Ser Gly Thr Thr Val Glu Glu Ala Tyr Lys Leu Ala Leu Lys
                405                 410                 415

Leu Gly Ile Ser Val Glu Glu Leu Leu Lys Leu Ala Lys Ala Ala Tyr
            420                 425                 430

Tyr Ser Gly Thr Thr Val Glu Glu Ala Tyr Lys Leu Ala Leu Lys Leu
        435                 440                 445

Gly Ile Ser Val Glu Glu Leu Leu Lys Leu Ala Lys Ala Ala Tyr Tyr
    450                 455                 460

Ser Gly Thr Thr Val Glu Glu Ala Tyr Lys Leu Ala Leu Lys Leu Gly
465                 470                 475                 480

Ile Ser Val Glu Glu Leu Leu Lys Leu Ala Lys Ala Ala Tyr Tyr Ser
                485                 490                 495

Gly Thr Thr Val Glu Glu Ala Tyr Lys Leu Ala Leu Lys Leu Gly
            500                 505                 510

<210> SEQ ID NO 150
<211> LENGTH: 628
<212> TYPE: PRT
<213> ORGANISM: Artificial Sequence
<220> FEATURE:
<223> OTHER INFORMATION: cTRP

<400> SEQUENCE: 150

Met Ala Ser Ser His His His His His His Ser Ser Gly Leu Val Pro
1               5                   10                  15

Arg Gly Ser Ser Met Gly Ile Ser Val Glu Glu Leu Leu Lys Leu Ala
                20                  25                  30

Lys Ala Ala Tyr Tyr Ser Gly Thr Thr Val Glu Glu Ala Tyr Lys Leu
            35                  40                  45

Ala Leu Lys Leu Gly Ile Ser Val Glu Glu Leu Leu Lys Leu Ala Glu
        50                  55                  60

Ala Ala Tyr Tyr Ser Gly Thr Thr Val Glu Glu Ala Tyr Lys Leu Ala
65                  70                  75                  80

Leu Lys Leu Gly Ile Ser Val Glu Glu Leu Leu Lys Leu Ala Lys Ala
                85                  90                  95

Ala Tyr Tyr Ser Gly Thr Thr Val Glu Glu Ala Tyr Lys Leu Ala Leu
            100                 105                 110

Lys Leu Gly Ile Ser Val Glu Glu Leu Leu Lys Leu Ala Lys Ala Ala
        115                 120                 125

-continued

```
Tyr Tyr Ser Gly Gly Ser Gly Gly Ser Gly Gly Ser Gly Ser Glu
    130                 135                 140

Trp Tyr Tyr Gly Asn Val Thr Arg His Gln Ala Glu Cys Ala Leu Asn
145                 150                 155                 160

Glu Arg Gly Val Glu Gly Asp Phe Leu Ile Arg Asp Ser Glu Ser Ser
                165                 170                 175

Pro Ser Asp Phe Ser Val Ser Leu Lys Ala Ser Gly Lys Asn Lys His
            180                 185                 190

Phe Lys Val Gln Leu Val Asp Asn Val Tyr Cys Ile Gly Gln Arg Arg
        195                 200                 205

Phe His Thr Met Asp Glu Leu Val Glu His Tyr Lys Lys Ala Pro Ile
    210                 215                 220

Phe Thr Ser Glu His Gly Glu Lys Leu Tyr Leu Val Arg Ala Leu Gln
225                 230                 235                 240

Gly Gly Ser Gly Gly Gly Ser Gly Ser Gly Thr Val Glu Glu Ala Tyr
                245                 250                 255

Lys Leu Ala Leu Lys Leu Gly Ile Ser Val Glu Glu Leu Leu Lys Leu
            260                 265                 270

Ala Glu Ala Ala Tyr Tyr Ser Gly Thr Thr Val Glu Glu Ala Tyr Lys
        275                 280                 285

Leu Ala Leu Lys Leu Gly Ile Ser Val Glu Glu Leu Leu Lys Leu Ala
290                 295                 300

Lys Ala Ala Tyr Tyr Ser Gly Thr Thr Val Glu Glu Ala Tyr Lys Leu
305                 310                 315                 320

Ala Leu Lys Leu Gly Ile Ser Val Glu Glu Leu Leu Lys Leu Ala Lys
                325                 330                 335

Ala Ala Tyr Tyr Ser Gly Thr Thr Val Glu Glu Ala Tyr Lys Leu Ala
            340                 345                 350

Leu Lys Leu Gly Ile Ser Val Glu Glu Leu Leu Lys Leu Ala Glu Ala
        355                 360                 365

Ala Tyr Tyr Ser Gly Thr Thr Val Glu Glu Ala Tyr Lys Leu Ala Leu
    370                 375                 380

Lys Leu Gly Ile Ser Val Glu Glu Leu Leu Lys Leu Ala Lys Ala Ala
385                 390                 395                 400

Tyr Tyr Ser Gly Thr Thr Val Glu Glu Ala Tyr Lys Leu Ala Leu Lys
                405                 410                 415

Leu Gly Ile Ser Val Glu Glu Leu Leu Lys Leu Ala Lys Ala Ala Tyr
            420                 425                 430

Tyr Ser Gly Gly Ser Gly Gly Ser Gly Gly Ser Gly Ser Glu Trp
        435                 440                 445

Tyr Tyr Gly Asn Val Thr Arg His Gln Ala Glu Cys Ala Leu Asn Glu
    450                 455                 460

Arg Gly Val Glu Gly Asp Phe Leu Ile Arg Asp Ser Glu Ser Ser Pro
465                 470                 475                 480

Ser Asp Phe Ser Val Ser Leu Lys Ala Ser Gly Lys Asn Lys His Phe
                485                 490                 495

Lys Val Gln Leu Val Asp Asn Val Tyr Cys Ile Gly Gln Arg Arg Phe
            500                 505                 510

His Thr Met Asp Glu Leu Val Glu His Tyr Lys Lys Ala Pro Ile Phe
        515                 520                 525

Thr Ser Glu His Gly Lys Leu Tyr Leu Val Arg Ala Leu Gln Gly
    530                 535                 540

Gly Ser Gly Gly Gly Ser Gly Ser Gly Thr Val Glu Glu Ala Tyr Lys
```

| | | | |
|---|---|---|---|
| 545 | 550 | 555 | 560 |

Leu Ala Leu Lys Leu Gly Ile Ser Val Glu Glu Leu Lys Leu Ala
              565                 570                 575

Glu Ala Ala Tyr Tyr Ser Gly Thr Thr Val Glu Glu Ala Tyr Lys Leu
            580                 585                 590

Ala Leu Lys Leu Gly Ile Ser Val Glu Glu Leu Leu Lys Leu Ala Lys
        595                 600                 605

Ala Ala Tyr Tyr Ser Gly Thr Thr Val Glu Glu Ala Tyr Lys Leu Ala
        610                 615                 620

Leu Lys Leu Gly
625

<210> SEQ ID NO 151
<211> LENGTH: 373
<212> TYPE: PRT
<213> ORGANISM: Artificial Sequence
<220> FEATURE:
<223> OTHER INFORMATION: cTRP

<400> SEQUENCE: 151

Met Ala Ser Ser His His His His His His Ser Ser Gly Leu Val Pro
1               5                   10                  15

Arg Gly Ser Ser Met Gly Leu Asp Pro Glu Ala Ile Lys Ala Ala Ala
            20                  25                  30

Glu Leu Gly Lys Ala Gly Ile Ser Glu Glu Ile Leu Glu Leu Leu
        35                  40                  45

Arg Ala Ala His Glu Leu Gly Leu Asp Pro Glu Ala Ile Lys Ala Ala
    50                  55                  60

Ala Glu Leu Gly Lys Ala Gly Ile Ser Glu Glu Ile Leu Glu Leu
65                  70                  75                  80

Leu Arg Ala Ala His Glu Leu Gly Leu Asp Pro Glu Ala Ile Lys Ala
                85                  90                  95

Ala Ala Glu Leu Gly Lys Ala Gly Ile Ser Ser Glu Glu Ile Leu Glu
            100                 105                 110

Leu Leu Arg Ala Ala His Glu Leu Gly Ser Gly Gly Gly Ser Gly Gly
        115                 120                 125

Ser Gly Ala Pro Thr Ser Ser Ser Thr Lys Lys Thr Gln Leu Gln Leu
    130                 135                 140

Glu His Leu Leu Leu Asp Leu Gln Met Ile Leu Asn Gly Ile Asn Asn
145                 150                 155                 160

Tyr Lys Asn Pro Lys Leu Thr Arg Met Leu Thr Phe Lys Phe Tyr Met
                165                 170                 175

Pro Lys Lys Ala Thr Glu Leu Lys His Leu Gln Cys Leu Glu Glu Glu
            180                 185                 190

Leu Lys Pro Leu Glu Glu Val Leu Asn Leu Ala Gln Ser Lys Asn Phe
        195                 200                 205

His Leu Arg Pro Arg Asp Leu Ile Ser Asn Ile Asn Val Ile Val Leu
    210                 215                 220

Glu Leu Lys Gly Ser Glu Thr Thr Phe Met Cys Glu Tyr Ala Asp Glu
225                 230                 235                 240

Thr Ala Thr Ile Val Glu Phe Leu Asn Arg Trp Ile Thr Phe Cys Gln
                245                 250                 255

Ser Ile Ile Ser Thr Leu Thr Gly Gly Ser Gly Gly Gly Ser Gly Ser
            260                 265                 270

Gly Gly Leu Asp Pro Glu Ala Ile Lys Ala Ala Ala Glu Leu Gly Lys

```
                275                 280                 285
Ala Gly Ile Ser Ser Glu Glu Ile Leu Glu Leu Leu Arg Ala Ala His
        290                 295                 300
Glu Leu Gly Leu Asp Pro Ala Ile Lys Ala Ala Glu Leu Gly
305                 310                 315                 320
Lys Ala Gly Ile Ser Ser Glu Glu Ile Leu Glu Leu Leu Arg Ala Ala
                325                 330                 335
His Glu Leu Gly Leu Asp Pro Glu Ala Ile Lys Ala Ala Glu Leu
            340                 345                 350
Gly Lys Ala Gly Ile Ser Ser Glu Glu Ile Leu Glu Leu Leu Arg Ala
                355                 360                 365
Ala His Glu Leu Gly
        370

<210> SEQ ID NO 152
<211> LENGTH: 11
<212> TYPE: PRT
<213> ORGANISM: Artificial Sequence
<220> FEATURE:
<223> OTHER INFORMATION: linker

<400> SEQUENCE: 152

Gly Gly Ser Gly Gly Gly Ser Gly Gly Ser Gly
1               5                   10

<210> SEQ ID NO 153
<211> LENGTH: 10
<212> TYPE: PRT
<213> ORGANISM: Artificial Sequence
<220> FEATURE:
<223> OTHER INFORMATION: linker

<400> SEQUENCE: 153

Gly Gly Ser Gly Gly Gly Ser Gly Ser Gly
1               5                   10

<210> SEQ ID NO 154
<211> LENGTH: 98
<212> TYPE: PRT
<213> ORGANISM: Artificial Sequence
<220> FEATURE:
<223> OTHER INFORMATION: functional domain

<400> SEQUENCE: 154

Ser Glu Trp Tyr Tyr Gly Asn Val Thr Arg His Gln Ala Glu Cys Ala
1               5                   10                  15
Leu Asn Glu Arg Gly Val Glu Gly Asp Phe Leu Ile Arg Asp Ser Glu
            20                  25                  30
Ser Ser Pro Ser Asp Phe Ser Val Ser Leu Lys Ala Ser Gly Lys Asn
        35                  40                  45
Lys His Phe Lys Val Gln Leu Val Asp Asn Val Tyr Cys Ile Gly Gln
    50                  55                  60
Arg Arg Phe His Thr Met Asp Glu Leu Val Glu His Tyr Lys Lys Ala
65                  70                  75                  80
Pro Ile Phe Thr Ser Glu His Gly Glu Lys Leu Tyr Leu Val Arg Ala
                85                  90                  95
Leu Gln

<210> SEQ ID NO 155
<211> LENGTH: 133
```

<212> TYPE: PRT
<213> ORGANISM: Artificial Sequence
<220> FEATURE:
<223> OTHER INFORMATION: functional domain

<400> SEQUENCE: 155

Ala Pro Thr Ser Ser Thr Lys Lys Thr Gln Leu Gln Leu Glu His
1               5                   10                  15

Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 156
<211> LENGTH: 6
<212> TYPE: PRT
<213> ORGANISM: Artificial Sequence
<220> FEATURE:
<223> OTHER INFORMATION: symmetry breaking motif

<400> SEQUENCE: 156

Lys Lys Lys Lys Lys Lys
1               5

<210> SEQ ID NO 157
<211> LENGTH: 6
<212> TYPE: PRT
<213> ORGANISM: Artificial Sequence
<220> FEATURE:
<223> OTHER INFORMATION: symmetry breaking motif

<400> SEQUENCE: 157

Glu Glu Glu Glu Glu Glu
1               5

<210> SEQ ID NO 158
<211> LENGTH: 6
<212> TYPE: PRT
<213> ORGANISM: Artificial Sequence
<220> FEATURE:
<223> OTHER INFORMATION: symmetry breaking motif

<400> SEQUENCE: 158

Lys Glu Lys Glu Lys Glu
1               5

<210> SEQ ID NO 159
<211> LENGTH: 10
<212> TYPE: PRT
<213> ORGANISM: Artificial Sequence
<220> FEATURE:

<223> OTHER INFORMATION: peptide recognized by SH2 domain

<400> SEQUENCE: 159

Glu His Ile Tyr Asp Glu Val Ala Ala Asp
1               5                   10

<210> SEQ ID NO 160
<211> LENGTH: 8
<212> TYPE: PRT
<213> ORGANISM: Artificial Sequence
<220> FEATURE:
<223> OTHER INFORMATION: linker

<400> SEQUENCE: 160

Gly Gly Ser Gly Gly Gly Ser Gly
1               5

<210> SEQ ID NO 161
<211> LENGTH: 10
<212> TYPE: PRT
<213> ORGANISM: Artificial Sequence
<220> FEATURE:
<223> OTHER INFORMATION: linker

<400> SEQUENCE: 161

Gly Gly Gly Gly Ser Gly Gly Gly Gly Ser
1               5                   10

<210> SEQ ID NO 162
<211> LENGTH: 8
<212> TYPE: PRT
<213> ORGANISM: Artificial Sequence
<220> FEATURE:
<223> OTHER INFORMATION: linker

<400> SEQUENCE: 162

Gly Gly Gly Ser Gly Gly Gly Ser
1               5

<210> SEQ ID NO 163
<211> LENGTH: 6
<212> TYPE: PRT
<213> ORGANISM: Artificial Sequence
<220> FEATURE:
<223> OTHER INFORMATION: linker

<400> SEQUENCE: 163

Gly Gly Ser Gly Gly Ser
1               5

<210> SEQ ID NO 164
<211> LENGTH: 276
<212> TYPE: PRT
<213> ORGANISM: Homo sapiens

<400> SEQUENCE: 164

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

```
Arg Lys Val Lys Ala His Ser Gln Thr His Arg Val Asp Leu Gly Thr
 65                  70                  75                  80

Leu Arg Gly Tyr Tyr Asn Gln Ser Glu Ala Gly Ser His Thr Val Gln
             85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Thr Thr Lys
130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
            195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
            275

<210> SEQ ID NO 165
<211> LENGTH: 99
<212> TYPE: PRT
<213> ORGANISM: Homo sapiens

<400> SEQUENCE: 165

Ile Gln Lys Thr Pro Gln Ile Gln Val Tyr Ser Arg His Pro Pro Glu
1               5                   10                  15

Asn Gly Lys Pro Asn Ile Leu Asn Cys Tyr Val Thr Gln Phe His Pro
            20                  25                  30

Pro His Ile Glu Ile Gln Met Leu Lys Asn Gly Lys Lys Ile Pro Lys
        35                  40                  45

Val Glu Met Ser Asp Met Ser Phe Ser Lys Asp Trp Ser Phe Tyr Ile
 50                 55                  60

Leu Ala His Thr Glu Phe Thr Pro Thr Glu Thr Asp Thr Tyr Ala Cys
 65                 70                  75                  80

Arg Val Lys His Ala Ser Met Ala Glu Pro Lys Thr Val Tyr Trp Asp
                85                  90                  95

Arg Asp Met

<210> SEQ ID NO 166
<211> LENGTH: 9
<212> TYPE: PRT
<213> ORGANISM: Artificial Sequence
<220> FEATURE:
<223> OTHER INFORMATION: immunogenic CMV peptide

<400> SEQUENCE: 166
```

Asn Leu Val Pro Met Val Ala Thr Val
1               5

<210> SEQ ID NO 167
<211> LENGTH: 641
<212> TYPE: PRT
<213> ORGANISM: Artificial Sequence
<220> FEATURE:
<223> OTHER INFORMATION: scMHC cTRP construct

<400> SEQUENCE: 167

Asn Leu Val Pro Met Val Ala Thr Val Gly Cys Gly Ala Ser Gly Gly
1               5                   10                  15

Gly Gly Ser Gly Gly Gly Ser Ile Gln Arg Thr Pro Lys Ile Gln
            20                  25                  30

Val Tyr Ser Arg His Pro Ala Glu Asn Gly Lys Ser Asn Phe Leu Asn
            35                  40                  45

Cys Tyr Val Ser Gly Phe His Pro Ser Asp Ile Glu Val Asp Leu Leu
        50                  55                  60

Lys Asn Gly Glu Arg Ile Glu Lys Val Glu His Ser Asp Leu Ser Phe
65                  70                  75                  80

Ser Lys Asp Trp Ser Phe Tyr Leu Leu Tyr Tyr Thr Glu Phe Thr Pro
                85                  90                  95

Thr Glu Lys Asp Glu Tyr Ala Cys Arg Val Asn His Val Thr Leu Ser
            100                 105                 110

Gln Pro Lys Ile Val Lys Trp Asp Arg Asp Met Gly Gly Gly Gly Ser
        115                 120                 125

Gly Gly Gly Gly Ser Gly Gly Gly Ser Gly Gly Gly Gly Ser Gly
    130                 135                 140

Ser His Ser Met Arg Tyr Phe Phe Thr Ser Val Ser Arg Pro Gly Arg
145                 150                 155                 160

Gly Glu Pro Arg Phe Ile Ala Val Gly Tyr Val Asp Asp Thr Gln Phe
                165                 170                 175

Val Arg Phe Asp Ser Asp Ala Ala Ser Gln Arg Met Glu Pro Arg Ala
            180                 185                 190

Pro Trp Ile Glu Gln Glu Gly Pro Glu Tyr Trp Asp Gly Glu Thr Arg
        195                 200                 205

Lys Val Lys Ala His Ser Gln Thr His Arg Val Asp Leu Gly Thr Leu
    210                 215                 220

Arg Gly Cys Tyr Asn Gln Ser Glu Ala Gly Ser His Thr Val Gln Arg
225                 230                 235                 240

Met Tyr Gly Cys Asp Val Gly Ser Asp Trp Arg Phe Leu Arg Gly Tyr
                245                 250                 255

His Gln Tyr Ala Tyr Asp Gly Lys Asp Tyr Ile Ala Leu Lys Glu Asp
            260                 265                 270

Leu Arg Ser Trp Thr Ala Ala Asp Met Ala Ala Gln Thr Thr Lys His
        275                 280                 285

Lys Trp Glu Ala Ala His Val Ala Glu Gln Leu Arg Ala Tyr Leu Glu
    290                 295                 300

Gly Thr Cys Val Glu Trp Leu Arg Arg Tyr Leu Glu Asn Gly Lys Glu
305                 310                 315                 320

Thr Leu Gln Arg Thr Asp Ala Pro Lys Thr His Met Thr His His Ala
                325                 330                 335

Val Ser Asp His Glu Ala Thr Leu Arg Cys Trp Ala Leu Ser Phe Tyr
            340                 345                 350

```
Pro Ala Glu Ile Thr Leu Thr Trp Gln Arg Asp Gly Glu Asp Gln Thr
        355                 360                 365
Gln Asp Thr Glu Leu Val Glu Thr Arg Pro Ala Gly Asp Gly Thr Phe
    370                 375                 380
Gln Lys Trp Ala Ala Val Val Pro Ser Gly Gln Glu Gln Arg Tyr
385                 390                 395                 400
Thr Cys His Val Gln His Glu Gly Leu Pro Lys Pro Leu Thr Leu Arg
                405                 410                 415
Trp Glu Pro Gly Gly Gly Ser Gly Gly Gly Ser Pro Glu Ala
            420                 425                 430
Ile Lys Ala Ala Ala Glu Leu Gly Lys Ala Gly Ile Ser Ser Glu Glu
        435                 440                 445
Ile Leu Glu Leu Leu Arg Ala Ala His Glu Leu Gly Leu Asp Pro Glu
    450                 455                 460
Ala Ile Lys Ala Ala Ala Glu Leu Gly Lys Ala Gly Ile Ser Ser Glu
465                 470                 475                 480
Glu Ile Leu Glu Leu Leu Arg Ala Ala His Glu Leu Gly Leu Asp Pro
                485                 490                 495
Glu Ala Ile Lys Ala Ala Ala Glu Leu Gly Lys Ala Gly Ile Ser Ser
            500                 505                 510
Glu Glu Ile Leu Glu Leu Leu Arg Ala Ala His Glu Leu Gly Leu Asp
        515                 520                 525
Pro Glu Ala Ile Lys Ala Ala Ala Glu Leu Gly Lys Ala Gly Ile Ser
    530                 535                 540
Ser Glu Glu Ile Leu Glu Leu Leu Arg Ala Ala His Glu Leu Gly Leu
545                 550                 555                 560
Asp Pro Glu Ala Ile Lys Ala Ala Ala Glu Leu Gly Lys Ala Gly Ile
                565                 570                 575
Ser Ser Glu Glu Ile Leu Glu Leu Leu Arg Ala Ala His Glu Leu Gly
            580                 585                 590
Leu Asp Pro Glu Ala Ile Lys Ala Ala Ala Glu Leu Gly Lys Ala Gly
        595                 600                 605
Ile Ser Ser Glu Glu Ile Leu Glu Leu Leu Arg Ala Ala His Glu Leu
    610                 615                 620
Gly Leu Asp Glu Asn Leu Tyr Phe Gln Gly Ser His His His His
625                 630                 635                 640
His

<210> SEQ ID NO 168
<211> LENGTH: 15
<212> TYPE: PRT
<213> ORGANISM: Artificial Sequence
<220> FEATURE:
<223> OTHER INFORMATION: linker

<400> SEQUENCE: 168

Gly Cys Gly Ala Ser Gly Gly Gly Ser Gly Gly Gly Gly Ser
1               5                   10                  15

<210> SEQ ID NO 169
<211> LENGTH: 20
<212> TYPE: PRT
<213> ORGANISM: Artificial Sequence
<220> FEATURE:
<223> OTHER INFORMATION: linker

<400> SEQUENCE: 169
```

Gly Gly Gly Gly Ser Gly Gly Gly Ser Gly Gly Gly Ser Gly
1               5               10              15

Gly Gly Gly Ser
            20

<210> SEQ ID NO 170
<211> LENGTH: 198
<212> TYPE: PRT
<213> ORGANISM: Artificial Sequence
<220> FEATURE:
<223> OTHER INFORMATION: toroid repeat

<400> SEQUENCE: 170

Pro Glu Ala Ile Lys Ala Ala Ala Glu Leu Gly Lys Ala Gly Ile Ser
1               5                   10                  15

Ser Glu Glu Ile Leu Glu Leu Leu Arg Ala Ala His Glu Leu Gly Leu
            20                  25                  30

Asp Pro Glu Ala Ile Lys Ala Ala Ala Glu Leu Gly Lys Ala Gly Ile
        35                  40                  45

Ser Ser Glu Glu Ile Leu Glu Leu Leu Arg Ala Ala His Glu Leu Gly
    50                  55                  60

Leu Asp Pro Glu Ala Ile Lys Ala Ala Ala Glu Leu Gly Lys Ala Gly
65                  70                  75                  80

Ile Ser Ser Glu Glu Ile Leu Glu Leu Leu Arg Ala Ala His Glu Leu
                85                  90                  95

Gly Leu Asp Pro Glu Ala Ile Lys Ala Ala Ala Glu Leu Gly Lys Ala
            100                 105                 110

Gly Ile Ser Ser Glu Glu Ile Leu Glu Leu Leu Arg Ala Ala His Glu
        115                 120                 125

Leu Gly Leu Asp Pro Glu Ala Ile Lys Ala Ala Ala Glu Leu Gly Lys
    130                 135                 140

Ala Gly Ile Ser Ser Glu Glu Ile Leu Glu Leu Leu Arg Ala Ala His
145                 150                 155                 160

Glu Leu Gly Leu Asp Pro Glu Ala Ile Lys Ala Ala Ala Glu Leu Gly
                165                 170                 175

Lys Ala Gly Ile Ser Ser Glu Glu Ile Leu Glu Leu Leu Arg Ala Ala
            180                 185                 190

His Glu Leu Gly Leu Asp
        195

<210> SEQ ID NO 171
<211> LENGTH: 14
<212> TYPE: PRT
<213> ORGANISM: Artificial Sequence
<220> FEATURE:
<223> OTHER INFORMATION: TEV cleavage site and His tag

<400> SEQUENCE: 171

Glu Asn Leu Tyr Phe Gln Gly Ser His His His His His His
1               5                   10

<210> SEQ ID NO 172
<211> LENGTH: 35
<212> TYPE: PRT
<213> ORGANISM: Artificial Sequence
<220> FEATURE:
<223> OTHER INFORMATION: alpha helical repeat

<400> SEQUENCE: 172

```
Leu Val Ser Leu Glu Gln Ala Leu Lys Ile Leu Lys Val Ala Ala Glu
1               5                   10                  15

Leu Gly Thr Thr Val Glu Glu Ala Val Lys Arg Ala Leu Lys Leu Lys
                20                  25                  30

Thr Lys Leu
        35

<210> SEQ ID NO 173
<211> LENGTH: 152
<212> TYPE: PRT
<213> ORGANISM: Homo sapiens

<400> SEQUENCE: 173

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
                20                  25                  30

Val Asn Cys Ser Asn Met Ile Asp Glu Ile Ile Thr His Leu Lys Gln
                35                  40                  45

Pro Pro Leu Pro Leu Leu Asp Phe Asn Asn Leu Asn Gly Glu Asp Gln
        50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
                100                 105                 110

Arg His Pro Ile His Ile Lys Asp Gly Asp Trp Asn Glu Phe Arg Arg
            115                 120                 125

Lys Leu Thr Phe Tyr Leu Lys Thr Leu Glu Asn Ala Gln Ala Gln Gln
        130                 135                 140

Thr Thr Leu Ser Leu Ala Ile Phe
145                 150

<210> SEQ ID NO 174
<211> LENGTH: 723
<212> TYPE: PRT
<213> ORGANISM: Homo sapiens

<400> SEQUENCE: 174

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
                20                  25                  30

Val Asn Lys Lys Gly Leu Leu Gly Asn Arg Asn Cys Cys Arg Gly Gly
                35                  40                  45

Ala Gly Pro Pro Pro Cys Ala Cys Arg Thr Phe Phe Arg Val Cys Leu
        50                  55                  60

Lys His Tyr Gln Ala Ser Val Ser Pro Glu Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
                100                 105                 110

Gly Phe Thr Trp Pro Gly Thr Phe Ser Leu Ile Ile Glu Ala Leu His
            115                 120                 125
```

-continued

```
Thr Asp Ser Pro Asp Asp Leu Ala Thr Glu Asn Pro Glu Arg Leu Ile
    130                 135                 140
Ser Arg Leu Ala Thr Gln Arg His Leu Thr Val Gly Glu Glu Trp Ser
145                 150                 155                 160
Gln Asp Leu His Ser Ser Gly Arg Thr Asp Leu Lys Tyr Ser Tyr Arg
                165                 170                 175
Phe Val Cys Asp Glu His Tyr Tyr Gly Glu Gly Cys Ser Val Phe Cys
            180                 185                 190
Arg Pro Arg Asp Asp Ala Phe Gly His Phe Thr Cys Gly Glu Arg Gly
        195                 200                 205
Glu Lys Val Cys Asn Pro Gly Trp Lys Gly Pro Tyr Cys Thr Glu Pro
    210                 215                 220
Ile Cys Leu Pro Gly Cys Asp Glu Gln His Gly Phe Cys Asp Lys Pro
225                 230                 235                 240
Gly Glu Cys Lys Cys Arg Val Gly Trp Gln Gly Arg Tyr Cys Asp Glu
                245                 250                 255
Cys Ile Arg Tyr Pro Gly Cys Leu His Gly Thr Cys Gln Gln Pro Trp
            260                 265                 270
Gln Cys Asn Cys Gln Glu Gly Trp Gly Gly Leu Phe Cys Asn Gln Asp
        275                 280                 285
Leu Asn Tyr Cys Thr His His Lys Pro Cys Lys Asn Gly Ala Thr Cys
    290                 295                 300
Thr Asn Thr Gly Gln Gly Ser Tyr Thr Cys Ser Cys Arg Pro Gly Tyr
305                 310                 315                 320
Thr Gly Ala Thr Cys Glu Leu Gly Ile Asp Glu Cys Asp Pro Ser Pro
                325                 330                 335
Cys Lys Asn Gly Gly Ser Cys Thr Asp Leu Glu Asn Ser Tyr Ser Cys
            340                 345                 350
Thr Cys Pro Pro Gly Phe Tyr Gly Lys Ile Cys Glu Leu Ser Ala Met
        355                 360                 365
Thr Cys Ala Asp Gly Pro Cys Phe Asn Gly Gly Arg Cys Ser Asp Ser
    370                 375                 380
Pro Asp Gly Gly Tyr Ser Cys Arg Cys Pro Val Gly Tyr Ser Gly Phe
385                 390                 395                 400
Asn Cys Glu Lys Lys Ile Asp Tyr Cys Ser Ser Ser Pro Cys Ser Asn
                405                 410                 415
Gly Ala Lys Cys Val Asp Leu Gly Asp Ala Tyr Leu Cys Arg Cys Gln
            420                 425                 430
Ala Gly Phe Ser Gly Arg His Cys Asp Asp Asn Val Asp Asp Cys Ala
        435                 440                 445
Ser Ser Pro Cys Ala Asn Gly Gly Thr Cys Arg Asp Gly Val Asn Asp
    450                 455                 460
Phe Ser Cys Thr Cys Pro Pro Gly Tyr Thr Gly Arg Asn Cys Ser Ala
465                 470                 475                 480
Pro Val Ser Arg Cys Glu His Ala Pro Cys His Asn Gly Ala Thr Cys
                485                 490                 495
His Glu Arg Gly His Arg Tyr Val Cys Glu Cys Ala Arg Gly Tyr Gly
            500                 505                 510
Gly Pro Asn Cys Gln Phe Leu Leu Pro Glu Leu Pro Pro Gly Pro Ala
        515                 520                 525
Val Val Asp Leu Thr Glu Lys Leu Glu Gly Gln Gly Gly Pro Phe Pro
    530                 535                 540
Trp Val Ala Val Cys Ala Gly Val Ile Leu Val Leu Met Leu Leu Leu
```

```
                545                 550                 555                 560
Gly Cys Ala Ala Val Val Cys Val Arg Leu Arg Leu Gln Lys His
                565                 570                 575
Arg Pro Pro Ala Asp Pro Cys Arg Gly Glu Thr Glu Thr Met Asn Asn
                580                 585                 590
Leu Ala Asn Cys Gln Arg Glu Lys Asp Ile Ser Val Ser Ile Ile Gly
                595                 600                 605
Ala Thr Gln Ile Lys Asn Thr Asn Lys Lys Ala Asp Phe His Gly Asp
                610                 615                 620
His Ser Ala Asp Lys Asn Gly Phe Lys Ala Arg Tyr Pro Ala Val Asp
625                 630                 635                 640
Tyr Asn Leu Val Gln Asp Leu Lys Gly Asp Asp Thr Ala Val Arg Asp
                    645                 650                 655
Ala His Ser Lys Arg Asp Thr Lys Cys Gln Pro Gln Gly Ser Ser Gly
                660                 665                 670
Glu Glu Lys Gly Thr Pro Thr Thr Leu Arg Gly Gly Glu Ala Ser Glu
                675                 680                 685
Arg Lys Arg Pro Asp Ser Gly Cys Ser Thr Ser Lys Asp Thr Lys Tyr
                690                 695                 700
Gln Ser Val Tyr Val Ile Ser Glu Glu Lys Asp Glu Cys Val Ile Ala
705                 710                 715                 720
Thr Glu Val

<210> SEQ ID NO 175
<211> LENGTH: 1218
<212> TYPE: PRT
<213> ORGANISM: Homo sapiens

<400> SEQUENCE: 175

Met Arg Ser Pro Arg Thr Arg Gly Arg Ser Gly Arg Pro Leu Ser Leu
1                   5                   10                  15
Leu Leu Ala Leu Leu Cys Ala Leu Arg Ala Lys Val Cys Gly Ala Ser
                20                  25                  30
Gly Gln Phe Glu Leu Glu Ile Leu Ser Met Gln Asn Val Asn Gly Glu
                35                  40                  45
Leu Gln Asn Gly Asn Cys Cys Gly Gly Ala Arg Asn Pro Gly Asp Arg
            50                  55                  60
Lys Cys Thr Arg Asp Glu Cys Asp Thr Tyr Phe Lys Val Cys Leu Lys
65                  70                  75                  80
Glu Tyr Gln Ser Arg Val Thr Ala Gly Gly Pro Cys Ser Phe Gly Ser
                85                  90                  95
Gly Ser Thr Pro Val Ile Gly Gly Asn Thr Phe Asn Leu Lys Ala Ser
                100                 105                 110
Arg Gly Asn Asp Arg Asn Arg Ile Val Leu Pro Phe Ser Phe Ala Trp
                115                 120                 125
Pro Arg Ser Tyr Thr Leu Leu Val Glu Ala Trp Asp Ser Ser Asn Asp
            130                 135                 140
Thr Val Gln Pro Asp Ser Ile Ile Glu Lys Ala Ser His Ser Gly Met
145                 150                 155                 160
Ile Asn Pro Ser Arg Gln Trp Gln Thr Leu Lys Gln Asn Thr Gly Val
                165                 170                 175
Ala His Phe Glu Tyr Gln Ile Arg Val Thr Cys Asp Asp Tyr Tyr Tyr
                180                 185                 190
Gly Phe Gly Cys Asn Lys Phe Cys Arg Pro Arg Asp Asp Phe Phe Gly
```

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

```
Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
            645                 650                 655

Asp Gly Trp Glu Gly Ala Tyr Cys Glu Thr Asn Ile Asn Asp Cys Ser
                660                 665                 670

Gln Asn Pro Cys His Asn Gly Gly Thr Cys Arg Asp Leu Val Asn Asp
            675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
            885                 890                 895

Cys Gly Pro Arg Pro Cys Leu Leu His Lys Gly His Ser Glu Cys Pro
        900                 905                 910

Ser Gly Gln Ser Cys Ile Pro Ile Leu Asp Asp Gln Cys Phe Val His
    915                 920                 925

Pro Cys Thr Gly Val Gly Glu Cys Arg Ser Ser Ser Leu Gln Pro Val
930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser Pro Ser Ala
        995                 1000                1005

Asn Asn Glu Ile His Val Ala Ile Ser Ala Glu Asp Ile Arg Asp
        1010                1015                1020

Asp Gly Asn Pro Ile Lys Glu Ile Thr Asp Lys Ile Ile Asp Leu
        1025                1030                1035
```

-continued

```
Val Ser Lys Arg Asp Gly Asn Ser Ser Leu Ile Ala Ala Val Ala
    1040            1045                1050

Glu Val Arg Val Gln Arg Arg Pro Leu Lys Asn Arg Thr Asp Phe
    1055            1060                1065

Leu Val Pro Leu Leu Ser Ser Val Leu Thr Val Ala Trp Ile Cys
    1070            1075                1080

Cys Leu Val Thr Ala Phe Tyr Trp Cys Leu Arg Lys Arg Arg Lys
    1085            1090                1095

Pro Gly Ser His Thr His Ser Ala Ser Glu Asp Asn Thr Thr Asn
    1100            1105                1110

Asn Val Arg Glu Gln Leu Asn Gln Ile Lys Asn Pro Ile Glu Lys
    1115            1120                1125

His Gly Ala Asn Thr Val Pro Ile Lys Asp Tyr Glu Asn Lys Asn
    1130            1135                1140

Ser Lys Met Ser Lys Ile Arg Thr His Asn Ser Glu Val Glu Glu
    1145            1150                1155

Asp Asp Met Asp Lys His Gln Gln Lys Ala Arg Phe Ala Lys Gln
    1160            1165                1170

Pro Ala Tyr Thr Leu Val Asp Arg Glu Glu Lys Pro Pro Asn Gly
    1175            1180                1185

Thr Pro Thr Lys His Pro Asn Trp Thr Asn Lys Gln Asp Asn Arg
    1190            1195                1200

Asp Leu Glu Ser Ala Gln Ser Leu Asn Arg Met Glu Tyr Ile Val
    1205            1210                1215
```